(12) United States Patent
Dubald

(10) Patent No.: US 12,331,306 B2
(45) Date of Patent: Jun. 17, 2025

(54) HERBICIDE TOLERANT PLANTS EXPRESSING A CYANOBACTERIAL PLASTOQUINONE BIOSYNTHETIC PATHWAY

(71) Applicant: BASF Agricultural Solutions Seed US LLC, Florham Park, NJ (US)

(72) Inventor: Manuel Dubald, Raleigh, NC (US)

(73) Assignee: BASF Agricultural Solutions US LLC, Research Triangle Park, NC (US)

( * ) Notice: Subject to any disclaimer, the term of this patent is extended or adjusted under 35 U.S.C. 154(b) by 1073 days.

(21) Appl. No.: 17/251,550

(22) PCT Filed: Jun. 14, 2019

(86) PCT No.: PCT/US2019/037295
§ 371 (c)(1),
(2) Date: Dec. 11, 2020

(87) PCT Pub. No.: WO2020/005588
PCT Pub. Date: Jan. 2, 2020

(65) Prior Publication Data
US 2021/0254091 A1 Aug. 19, 2021

Related U.S. Application Data

(60) Provisional application No. 62/691,629, filed on Jun. 29, 2018.

(51) Int. Cl.
*C12N 15/82* (2006.01)
*C12N 9/02* (2006.01)
*C12N 9/10* (2006.01)
*C12N 9/88* (2006.01)

(52) U.S. Cl.
CPC ....... *C12N 15/8274* (2013.01); *C12N 9/0073* (2013.01); *C12N 9/1007* (2013.01); *C12N 9/1085* (2013.01); *C12N 9/88* (2013.01); *C12Y 114/13001* (2013.01); *C12Y 201/01* (2013.01); *C12Y 205/01* (2013.01); *C12Y 205/01042* (2013.01); *C12Y 401/01* (2013.01); *C12Y 401/0304* (2013.01)

(58) Field of Classification Search
CPC .... C12N 15/8274; C12N 9/1007; C12N 9/88; C12N 9/0073; C12Y 401/0304
See application file for complete search history.

(56) References Cited

PUBLICATIONS

Nowicka and Kruk (2016) Acta Physiol Plant 38:49 pp. 1-12. (Year: 2016).*

* cited by examiner

*Primary Examiner* — Russell Kallis
(74) *Attorney, Agent, or Firm* — Richa Dhindsa; BASF Global Intellectual Property

(57) ABSTRACT

A method for conferring tolerance to a 4-hydroxyphenylpyruvate dioxygenase (HPPD) inhibitor herbicide in a plant by expressing one or more polypeptide components of an exogenous plastoquinone-9 pathway in the plant. Nucleic acids, vectors, transgenic cells and transgenic plants useful in such a method are also disclosed.

20 Claims, 4 Drawing Sheets

Specification includes a Sequence Listing.

A.

B.

```
                         SEQUENCE LISTING

<160> NUMBER OF SEQ ID NOS: 23

<210> SEQ ID NO 1
<211> LENGTH: 139
<212> TYPE: PRT
<213> ORGANISM: Synechocystis PCC6803

<400> SEQUENCE: 1

Met Asp Val Ile Asp Met Ala Pro Val Ser Pro Arg Asp Asp Gly Ala
1               5                   10                  15

Pro Pro Gln Ile Asn Thr Val Pro Gly Pro His Leu Arg Arg Gln Val
            20                  25                  30

Trp Leu Arg Thr Lys Ser Gly Gln Arg Leu Ala Tyr Ala Val Ser Trp
        35                  40                  45

Trp Asp Ala Ser His Val Asp Glu Tyr Leu Gln Asn Arg Ser Leu Pro
    50                  55                  60

Ile Trp Asp Ser Leu Ser Arg Leu His Thr Glu Leu Tyr Arg Asp Ile
65                  70                  75                  80

Gln Ala Ile Tyr Cys Gly His Asn Arg Thr Leu Ala Lys Ala Phe Gly
                85                  90                  95

Gln Glu Gly Pro Phe Trp Gly Arg His Tyr Leu Phe Trp His Asp Arg
            100                 105                 110

Lys Pro Leu Thr Leu Ile Tyr Glu Ile Phe Ser Pro Tyr Leu Ser Arg
        115                 120                 125

Tyr Leu Gly Glu Leu Pro Arg Pro Lys Phe Glu
    130                 135

<210> SEQ ID NO 2
<211> LENGTH: 292
<212> TYPE: PRT
<213> ORGANISM: Synechocystis PCC6803

<400> SEQUENCE: 2

Met Val Ala Gln Thr Pro Ser Ser Pro Pro Leu Trp Leu Thr Ile Ile
1               5                   10                  15

Tyr Leu Leu Arg Trp His Lys Pro Ala Gly Arg Leu Ile Leu Met Ile
            20                  25                  30

Pro Ala Leu Trp Ala Val Cys Leu Ala Ala Gln Gly Leu Pro Pro Leu
        35                  40                  45

Pro Leu Leu Gly Thr Ile Ala Leu Gly Thr Leu Ala Thr Ser Gly Leu
    50                  55                  60

Gly Cys Val Val Asn Asp Leu Trp Asp Arg Asp Ile Asp Pro Gln Val
```

```
                65                  70                  75                  80
        Glu Arg Thr Lys Gln Arg Pro Leu Ala Ala Arg Ala Leu Ser Val Gln
                            85                  90                  95

Val Gly Ile Gly Val Ala Leu Val Ala Leu Leu Cys Ala Ala Gly Leu
                            100                 105                 110

Ala Phe Tyr Leu Thr Pro Leu Ser Phe Trp Leu Cys Val Ala Ala Val
                            115                 120                 125

Pro Val Ile Val Ala Tyr Pro Gly Ala Lys Arg Val Phe Pro Val Pro
                    130                 135                 140

Gln Leu Val Leu Ser Ile Ala Trp Gly Phe Ala Val Leu Ile Ser Trp
        145                 150                 155                 160

Ser Ala Val Thr Gly Asp Leu Thr Asp Ala Thr Trp Val Leu Trp Gly
                            165                 170                 175

Ala Thr Val Phe Trp Thr Leu Gly Phe Asp Thr Val Tyr Ala Met Ala
                        180                 185                 190

Asp Arg Glu Asp Asp Arg Arg Ile Gly Val Asn Ser Ser Ala Leu Phe
                        195                 200                 205

Phe Gly Gln Tyr Val Gly Glu Ala Val Gly Ile Phe Phe Ala Leu Thr
                        210                 215                 220

Ile Gly Cys Leu Phe Tyr Leu Gly Met Ile Leu Met Leu Asn Pro Leu
        225                 230                 235                 240

Tyr Trp Leu Ser Leu Ala Ile Ala Ile Val Gly Trp Val Ile Gln Tyr
                        245                 250                 255

Ile Gln Leu Ser Ala Pro Thr Pro Glu Pro Lys Leu Tyr Gly Gln Ile
                        260                 265                 270

Phe Gly Gln Asn Val Ile Ile Gly Phe Val Leu Leu Ala Gly Met Leu
                        275                 280                 285

Leu Gly Trp Leu
            290

<210> SEQ ID NO 3
<211> LENGTH: 206
<212> TYPE: PRT
<213> ORGANISM: Synechocystis PCC6803

<400> SEQUENCE: 3

Met Ala Gln Pro Leu Ile Leu Gly Val Ser Gly Ala Ser Gly Leu Ile
        1               5                   10                  15

Tyr Ala Val Arg Ala Ile Lys His Leu Leu Ala Ala Asp Tyr Thr Ile
                        20                  25                  30

Glu Leu Val Ala Ser Arg Ala Ser Tyr Gln Val Trp Gln Ala Glu Gln
                        35                  40                  45

Asn Ile Gln Met Pro Gly Glu Pro Ser Ala Gln Ala Glu Phe Trp Arg
                50                  55                  60

Ser Gln Ala Gly Val Glu Lys Gly Gly Lys Leu Ile Cys His Arg Trp
        65                  70                  75                  80

Gly Asp Val Gly Ala Thr Ile Ala Ser Gly Ser Tyr Arg Cys Ala Gly
                            85                  90                  95

Met Val Val Leu Pro Cys Ser Met Ser Thr Val Ala Lys Leu Ala Val
                            100                 105                 110

Gly Met Ser Ser Asp Leu Leu Glu Arg Ala Ala Asp Val Gln Ile Lys
                        115                 120                 125

Glu Gly Lys Pro Leu Val Val Pro Arg Glu Thr Pro Leu Ser Leu
                    130                 135                 140
```

```
Ile His Leu Arg Asn Leu Thr Ser Leu Ala Glu Ala Gly Val Arg Ile
145                 150                 155                 160

Val Pro Ala Ile Pro Ala Trp Tyr His Gln Pro Gln Ser Val Glu Asp
                165                 170                 175

Leu Val Asp Phe Val Val Ala Arg Ala Leu Asp Gln Leu Ala Ile Asp
            180                 185                 190

Cys Val Pro Leu Gln Arg Trp Gln Gly Gly Met Glu Gly Glu
        195                 200                 205

<210> SEQ ID NO 4
<211> LENGTH: 501
<212> TYPE: PRT
<213> ORGANISM: Synechocystis PCC6803

<400> SEQUENCE: 4

Met Ala Arg Asp Leu Arg Gly Phe Ile Gln Leu Leu Glu Thr Arg Gly
1               5                   10                  15

Gln Leu Arg Arg Ile Thr Ala Glu Val Asp Pro Asp Leu Glu Val Ala
                20                  25                  30

Glu Ile Ser Asn Arg Met Leu Gln Ala Gly Gly Pro Gly Leu Leu Phe
            35                  40                  45

Glu Asn Val Lys Gly Ser Pro Phe Pro Val Ala Val Asn Leu Met Gly
        50                  55                  60

Thr Val Glu Arg Ile Cys Trp Ala Met Asn Met Asp His Pro Leu Glu
65                  70                  75                  80

Leu Glu Asp Leu Gly Lys Lys Leu Ala Leu Leu Gln Gln Pro Lys Pro
                85                  90                  95

Pro Lys Lys Ile Ser Gln Ala Ile Asp Phe Gly Lys Val Leu Phe Asp
                100                 105                 110

Val Leu Lys Ala Lys Pro Gly Arg Asn Phe Phe Pro Pro Cys Gln Glu
            115                 120                 125

Val Val Ile Asp Gly Glu Asn Leu Asp Leu Asn Gln Ile Pro Leu Ile
        130                 135                 140

Arg Pro Tyr Pro Gly Asp Ala Gly Lys Ile Ile Thr Leu Gly Leu Val
145                 150                 155                 160

Ile Thr Lys Asp Cys Glu Thr Gly Thr Pro Asn Val Gly Val Tyr Arg
                165                 170                 175

Leu Gln Leu Gln Ser Lys Thr Thr Met Thr Val His Trp Leu Ser Val
            180                 185                 190

Arg Gly Gly Ala Arg His Leu Arg Lys Ala Ala Glu Gln Gly Lys Lys
        195                 200                 205

Leu Glu Val Ala Ile Ala Leu Gly Val Asp Pro Leu Ile Ile Met Ala
    210                 215                 220

Ala Ala Thr Pro Ile Pro Val Asp Leu Ser Glu Trp Leu Phe Ala Gly
225                 230                 235                 240

Leu Tyr Gly Gly Ser Gly Val Ala Leu Ala Lys Cys Lys Thr Val Asp
                245                 250                 255

Leu Glu Val Pro Ala Asp Ser Glu Phe Val Leu Glu Gly Thr Ile Thr
            260                 265                 270

Pro Gly Glu Met Leu Pro Asp Gly Pro Phe Gly Asp His Met Gly Tyr
        275                 280                 285

Tyr Gly Gly Val Glu Asp Ser Pro Leu Val Arg Phe Gln Cys Leu Thr
    290                 295                 300

His Arg Lys Asn Pro Val Tyr Leu Thr Thr Phe Ser Gly Arg Pro Pro
305                 310                 315                 320
```

```
Lys Glu Glu Ala Met Met Ala Ile Ala Leu Asn Arg Ile Tyr Thr Pro
                325                 330                 335

Ile Leu Arg Gln Gln Val Ser Glu Ile Thr Asp Phe Phe Leu Pro Met
            340                 345                 350

Glu Ala Leu Ser Tyr Lys Ala Ala Ile Ile Ser Ile Asp Lys Ala Tyr
                355                 360                 365

Pro Gly Gln Ala Lys Arg Ala Ala Leu Ala Phe Trp Ser Ala Leu Pro
            370                 375                 380

Gln Phe Thr Tyr Thr Lys Phe Val Ile Val Val Asp Lys Ser Ile Asn
385                 390                 395                 400

Ile Arg Asp Pro Arg Gln Val Val Trp Ala Ile Ser Ser Lys Val Asp
                405                 410                 415

Pro Val Arg Asp Val Phe Ile Leu Pro Glu Thr Pro Phe Asp Ser Leu
                420                 425                 430

Asp Phe Ala Ser Glu Lys Ile Gly Leu Gly Gly Arg Met Gly Ile Asp
                435                 440                 445

Ala Thr Thr Lys Ile Pro Pro Glu Thr Asp His Glu Trp Gly Glu Val
            450                 455                 460

Leu Glu Ser Asp Pro Ala Met Ala Glu Gln Val Ser Gln Arg Trp Ala
465                 470                 475                 480

Glu Tyr Gly Leu Gly Asp Ile Asn Leu Thr Glu Val Asn Pro Asn Leu
                485                 490                 495

Phe Gly Tyr Asp Val
            500

<210> SEQ ID NO 5
<211> LENGTH: 414
<212> TYPE: PRT
<213> ORGANISM: Synechocystis PCC6803

<400> SEQUENCE: 5

Met Thr Phe Val Ala Ala Ser Ile Thr Asp Asn Gln Phe Asp Val Ala
1               5                   10                  15

Ile Ala Gly Gly Gly Val Val Gly Leu Val Leu Ala Ala Gly Leu Arg
            20                  25                  30

His Thr Gly Leu Lys Ile Ala Ile Ile Glu Ala Leu Pro Lys Glu Gln
        35                  40                  45

Ala Leu Thr Lys Pro Gln Ala Tyr Ala Ile Ser Leu Leu Ser Gly Lys
    50                  55                  60

Ile Leu Ala Gly Leu Gly Val Trp Glu Asn Ile Lys Asp Ser Ile Gly
65                  70                  75                  80

His Phe Glu Arg Ile Gln Ile Ser Asp Asn Asp Tyr Arg Gly Thr Val
                85                  90                  95

Pro Phe Ala Lys Glu Asp Val Asp Glu Leu Ala Leu Gly His Val Ala
            100                 105                 110

Glu His Pro Val Ile Leu Gln Ala Leu Glu Asn Cys Val Glu Gln Cys
        115                 120                 125

Pro Arg Ile Ala Trp Phe Arg Pro Ala Glu Leu Ile Ser Phe Thr Ala
    130                 135                 140

Gly Glu Asn His Lys Gln Val Thr Leu Gln Gln Gly Arg Glu Ile
145                 150                 155                 160

Thr Leu Gln Thr Lys Leu Leu Val Ala Ala Asp Gly Ala Arg Ser His
                165                 170                 175

Thr Arg Ser Leu Ala Gly Ile Gln Thr Lys Gly Trp Lys Tyr Trp Gln
```

```
                180              185              190
Ser Cys Val Ala Phe Thr Ile Gln His Gln Ala Pro Asp Asn Thr Thr
            195              200              205

Ala Phe Glu Arg Phe Cys Asp Thr Gly Pro Met Gly Ile Leu Pro Leu
        210              215              220

Pro Gly Asp Arg Ala Gln Ile Val Trp Thr Met Pro His His Lys Ala
225              230              235              240

His Thr Leu Val Asn Leu Pro Glu Ala Asp Phe Ile Thr Glu Leu Arg
            245              250              255

Gln Arg Ile Gly Asp Arg Leu Gly Glu Phe His Leu Ile Asn Ala Arg
        260              265              270

Arg Leu Phe Pro Val Gln Leu Met Gln Ser Asp Cys Tyr Val Gln Pro
    275              280              285

Arg Leu Ala Leu Val Gly Asp Ala Ala His Cys Cys His Pro Val Gly
        290              295              300

Gly Gln Gly Leu Asn Leu Gly Ile Arg Asp Gly Ala Ala Leu Ala Gln
305              310              315              320

Val Ile Ala Thr Ala His Ser Gln Gly Glu Asp Trp Gly Ser Leu Ala
                325              330              335

Val Leu Lys Arg Tyr Glu His Trp Arg Lys Pro Glu Asn Trp Leu Ile
            340              345              350

Leu Gly Phe Thr Asp Leu Leu Asp Arg Phe Phe Ser Ser His Trp Leu
        355              360              365

Pro Ala Ile Ala Leu Arg Arg Phe Gly Leu Glu Val Leu Arg Leu Val
    370              375              380

Pro Pro Ala Lys Lys Leu Ala Leu Arg Leu Met Thr Gly Leu Leu Gly
385              390              395              400

Arg Lys Pro Gln Leu Ala Thr Gly Gln Ser Leu Val Ser Gln
                405              410
```

<210> SEQ ID NO 6
<211> LENGTH: 318
<212> TYPE: PRT
<213> ORGANISM: Synechocystis PCC6803

<400> SEQUENCE: 6

```
Met Pro Glu Tyr Leu Leu Pro Ala Gly Leu Ile Ser Leu Ser Leu
1               5                10               15

Ala Ile Ala Ala Gly Leu Tyr Leu Leu Thr Ala Arg Gly Tyr Gln Ser
            20              25               30

Ser Asp Ser Val Ala Asn Ala Tyr Asp Gln Trp Thr Glu Asp Gly Ile
        35              40              45

Leu Glu Tyr Tyr Trp Gly Asp His Ile His Leu Gly His Tyr Gly Asp
    50              55              60

Pro Pro Val Ala Lys Asp Phe Ile Gln Ser Lys Ile Asp Phe Val His
65              70              75              80

Ala Met Ala Gln Trp Gly Gly Leu Asp Thr Leu Pro Pro Gly Thr Thr
                85              90              95

Val Leu Asp Val Gly Cys Gly Ile Gly Gly Ser Ser Arg Ile Leu Ala
            100             105             110

Lys Asp Tyr Gly Phe Asn Val Thr Gly Ile Thr Ile Ser Pro Gln Gln
        115             120             125

Val Lys Arg Ala Thr Glu Leu Thr Pro Pro Asp Val Thr Ala Lys Phe
    130             135             140
```

Ala Val Asp Asp Ala Met Ala Leu Ser Phe Pro Asp Gly Ser Phe Asp
145                 150                 155                 160

Val Val Trp Ser Val Glu Ala Gly Pro His Met Pro Asp Lys Ala Val
                165                 170                 175

Phe Ala Lys Glu Leu Leu Arg Val Val Lys Pro Gly Gly Ile Leu Val
            180                 185                 190

Val Ala Asp Trp Asn Gln Arg Asp Arg Gln Val Pro Leu Asn Phe
        195                 200                 205

Trp Glu Lys Pro Val Met Arg Gln Leu Leu Asp Gln Trp Ser His Pro
    210                 215                 220

Ala Phe Ala Ser Ile Glu Gly Phe Ala Glu Asn Leu Glu Ala Thr Gly
225                 230                 235                 240

Leu Val Glu Gly Gln Val Thr Thr Ala Asp Trp Thr Val Pro Thr Leu
                245                 250                 255

Pro Ala Trp Leu Asp Thr Ile Trp Gln Gly Ile Ile Arg Pro Gln Gly
            260                 265                 270

Trp Leu Gln Tyr Gly Ile Arg Gly Phe Ile Lys Ser Val Arg Glu Val
        275                 280                 285

Pro Thr Ile Leu Leu Met Arg Leu Ala Phe Gly Val Gly Leu Cys Arg
    290                 295                 300

Phe Gly Met Phe Lys Ala Val Arg Lys Asn Ala Thr Gln Ala
305                 310                 315

<210> SEQ ID NO 7
<211> LENGTH: 317
<212> TYPE: PRT
<213> ORGANISM: Synechocystis PCC6803

<400> SEQUENCE: 7

Met Val Tyr His Val Arg Pro Lys His Ala Leu Phe Leu Ala Phe Tyr
1               5                   10                  15

Cys Tyr Phe Ser Leu Leu Thr Met Ala Ser Ala Thr Ile Ala Ser Ala
            20                  25                  30

Asp Leu Tyr Glu Lys Ile Lys Asn Phe Tyr Asp Asp Ser Ser Gly Leu
        35                  40                  45

Trp Glu Asp Val Trp Gly Glu His Met His His Gly Tyr Tyr Gly Pro
    50                  55                  60

His Gly Thr Tyr Arg Ile Asp Arg Arg Gln Ala Gln Ile Asp Leu Ile
65                  70                  75                  80

Lys Glu Leu Leu Ala Trp Ala Val Pro Gln Asn Ser Ala Lys Pro Arg
            85                  90                  95

Lys Ile Leu Asp Leu Gly Cys Gly Ile Gly Gly Ser Ser Leu Tyr Leu
        100                 105                 110

Ala Gln Gln His Gln Ala Glu Val Met Gly Ala Ser Leu Ser Pro Val
    115                 120                 125

Gln Val Glu Arg Ala Gly Glu Arg Ala Arg Ala Leu Gly Leu Gly Ser
130                 135                 140

Thr Cys Gln Phe Gln Val Ala Asn Ala Leu Asp Leu Pro Phe Ala Ser
145                 150                 155                 160

Asp Ser Phe Asp Trp Val Trp Ser Leu Glu Ser Gly Glu His Met Pro
                165                 170                 175

Asn Lys Ala Gln Phe Leu Gln Glu Ala Trp Arg Val Leu Lys Pro Gly
            180                 185                 190

Gly Arg Leu Ile Leu Ala Thr Trp Cys His Arg Pro Ile Asp Pro Gly
        195                 200                 205

```
Asn Gly Pro Leu Thr Ala Asp Glu Arg Arg His Leu Gln Ala Ile Tyr
            210                 215                 220

Asp Val Tyr Cys Leu Pro Tyr Val Val Ser Leu Pro Asp Tyr Glu Ala
225                 230                 235                 240

Ile Ala Arg Glu Cys Gly Phe Gly Glu Ile Lys Thr Ala Asp Trp Ser
                245                 250                 255

Val Ala Val Ala Pro Phe Trp Asp Arg Val Ile Glu Ser Ala Phe Asp
                260                 265                 270

Pro Arg Val Leu Trp Ala Leu Gly Gln Ala Gly Pro Lys Ile Ile Asn
                275                 280                 285

Ala Ala Leu Cys Leu Arg Leu Met Lys Trp Gly Tyr Glu Arg Gly Leu
290                 295                 300

Val Arg Phe Gly Leu Leu Thr Gly Ile Lys Pro Leu Val
305                 310                 315

<210> SEQ ID NO 8
<211> LENGTH: 265
<212> TYPE: PRT
<213> ORGANISM: Synechocystis PCC6803

<400> SEQUENCE: 8

Met Lys Lys Asn Val Tyr Tyr Ser Lys Ile Ala Asp Ile Tyr Asp Gln
1               5                   10                  15

Thr Arg Trp Met Thr Glu Pro Ile Ala Glu Val Ala Asp Phe Ile
                20                  25                  30

Leu Ala Leu Val Lys Ala Thr Arg Glu Thr Thr Phe Leu Glu Pro Gly
                35                  40                  45

Val Gly Thr Gly Leu Asn Val Ile Pro Leu Val Arg Arg Gly Tyr Ser
            50                  55                  60

Val Thr Gly Val Asp Ile Ser Gln Glu Met Leu Ser Gln Phe Ser Gln
65                  70                  75                  80

Lys Leu Pro Arg Ile Pro Pro Asn Leu Arg Leu Ile His Glu Asp Ala
                85                  90                  95

Ser Gln Leu Ser Phe Pro Asp Ser Ser Phe Asp Val Val Leu Thr Val
                100                 105                 110

His Met Leu His Ser Val Ser Asn Leu Gly Met Phe Leu Asp Glu Ile
                115                 120                 125

Asp Arg Val Leu Lys Pro Asn Gly Phe Tyr Leu Asn Ala Gln Trp Val
                130                 135                 140

Thr Pro Pro Ala His Leu Glu Phe Glu Asn His Phe Lys Thr Ile Leu
145                 150                 155                 160

Leu Lys Tyr Gln Glu Pro Lys Pro Ser Gln Gln Ser Leu Glu Val Thr
                165                 170                 175

Asn Lys Ile Asn Ile Asp Glu Tyr Leu Leu Asn Lys Gly Tyr Gln Cys
                180                 185                 190

Asn Tyr Leu Thr Ala Lys Glu Trp Thr Val Ser Asn Gln Val Gln Glu
                195                 200                 205

Leu Leu His Phe Tyr Arg Ser His Ala Tyr Gly Leu Cys Trp Leu Leu
                210                 215                 220

Pro Asp Glu Ala Phe Asn Leu Ala Ile Lys Glu Phe Glu Val Phe Cys
225                 230                 235                 240

Tyr Glu Tyr Tyr Asp Ser Leu Lys Val Glu Leu Ser Ser Gln Ala Gln
                245                 250                 255

Phe Glu Ile Trp Ala Tyr Thr Val Lys
```

<210> SEQ ID NO 9
<211> LENGTH: 270
<212> TYPE: PRT
<213> ORGANISM: Synechocystis PCC6803

<400> SEQUENCE: 9

```
Met Thr Tyr Phe Ala Ser Asp Phe Gln Asp Leu Asp Asn Ser Gly Asn
1               5                   10                  15

Ile Glu Asn Phe Ile Arg Cys Leu Glu Leu Gln Gln Ser Leu Asp Leu
            20                  25                  30

Tyr Lys Tyr Tyr Lys Gln Lys Thr Phe Glu Lys Met Gln Leu Lys Pro
        35                  40                  45

Gly Asp Ser Val Leu Glu Val Gly Cys Gly Thr Gly Asn Asp Ala Leu
    50                  55                  60

Leu Leu Ala Asn Tyr Val Gly Glu Thr Gly Lys Val Thr Ala Val Asp
65                  70                  75                  80

Arg Ser Gln Phe Met Leu Asp Gln Ala Arg Glu Ala Lys Asn Ser
            85                  90                  95

Thr Thr Lys Phe Glu Phe Val Leu Ala Asp Ala Glu Gln Leu Pro Phe
            100                 105                 110

Pro Gly Ala Asn Phe Thr Ala Ala Arg Val Asp Arg Thr Leu Gln His
        115                 120                 125

Ile Ala Gln Pro Gln Lys Ala Ile Ala Glu Met Ala Arg Val Val Gln
130                 135                 140

Ser Asn Gly Trp Val Val Ala Phe Glu Pro Asp Trp Glu Thr Leu Val
145                 150                 155                 160

Ile Asp Ser Asp Gln Arg Gly Val Thr Arg Ala Ile Thr Asn Phe Trp
                165                 170                 175

Cys Asp Asn Phe Pro Ser Gly Trp Val Gly Arg Tyr Leu Phe Lys Tyr
            180                 185                 190

Phe Arg Gln Ala Gly Leu Thr Asp Ile Ala Val Asp Pro Ile Thr Ile
        195                 200                 205

Cys Leu Thr Glu Phe Glu Leu Ala Asp Lys Ile Leu Asp Leu Ser Arg
    210                 215                 220

Thr Val Glu Lys Ile Ser Glu Gln Gly Thr Ile Ser Gln Asn Asp Leu
225                 230                 235                 240

Thr Leu Trp Phe Lys Ala Ile Asp Gln Asn Asp Gln Ala Gly Glu Phe
                245                 250                 255

Phe Cys Ala Phe Thr Ala Phe Leu Val Arg Gly Arg Lys Pro
            260                 265                 270
```

<210> SEQ ID NO 10
<211> LENGTH: 212
<212> TYPE: PRT
<213> ORGANISM: Synechocystis PCC6803

<400> SEQUENCE: 10

```
Met Ala Thr Ile Phe Arg Thr Trp Ser Tyr Gln Tyr Pro Trp Val Tyr
1               5                   10                  15

Ala Leu Val Ser Arg Leu Ala Thr Leu Asn Val Gly Gly Glu Glu Arg
            20                  25                  30

Phe His Gln Leu Pro Leu Glu Asn Leu Ala Ile Ser Pro Gly Gln Lys
        35                  40                  45

Val Leu Asp Leu Cys Cys Gly Gly Gly Gln Ala Thr Val Tyr Leu Ala
```

```
                50                  55                  60
Gln Ser Gly Ala Thr Val Val Gly Leu Asp Ala Ser Pro Lys Ala Leu
 65                  70                  75                  80

Gly Arg Ala Lys Ile Asn Val Pro Gln Ala Thr Tyr Val Gln Gly Leu
                 85                  90                  95

Ala Glu Asp Leu Pro Phe Gly Glu Gly Phe Asp Leu Val His Thr
            100                 105                 110

Ser Val Ala Leu His Glu Met Thr Pro Ala Gln Leu Gln Ser Ile Ile
        115                 120                 125

Ser Gly Val His Arg Val Leu Lys Pro Gly Gly Ile Phe Ala Leu Val
    130                 135                 140

Asp Leu His Arg Pro Ser Asn Trp Leu Phe Trp Pro Pro Leu Ala Ile
145                 150                 155                 160

Phe Met Gly Leu Phe Glu Thr Glu Thr Ala Trp Gln Leu Ile Asn Thr
                165                 170                 175

Asp Leu Gly Ser Leu Leu Asp Gln Ala Gly Phe Thr Val Val Arg Lys
            180                 185                 190

His Leu Tyr Ala Gly Gly Ser Leu Gln Val Ile Gln Ala Arg Ala Asn
        195                 200                 205

Lys Thr Val Asn
    210

<210> SEQ ID NO 11
<211> LENGTH: 606
<212> TYPE: DNA
<213> ORGANISM: Synechocystis PCC6803

<400> SEQUENCE: 11
atgaagctct ctcccgctgt ttctcctagt cttgcttggc attctttgga tttgctgtgg      60
caaggagatc aacatgatgt gaggcatggg cttcctcatt ctgttcttcc tcctccatgg     120
cagatcctca ttcttggaga tggctcccca acaaggcatt gcagcttct cactggagag      180 aagacagaag tggatgtgat tgacatggct cctgtttcac caagagatga tggtgctcct     240
cctcaaatta acactgttcc tggccctcac ttgagaaggc aagtttggct gaggaccaag     300
agtggccaaa ggcttgctta tgctgtttct tggtgggatg cttctcatgt tgatgaatat     360
ttgcaaaaca gaagtttgcc aatttgggat tctctctcaa ggcttcacac agagctttac     420
agagacattc aagctatcta ttgtggccac aacagaactc tagcaaaggc ttttggccaa     480 gaaggacccct tctggggaag gcattacctc ttttggcatg acaggaagcc attgacattg     540
atctatgaga tcttctctcc atatctctca agatatcttg gagagcttcc aaggccaaaa     600
tttgaa                                                                606

<210> SEQ ID NO 12
<211> LENGTH: 879
<212> TYPE: DNA
<213> ORGANISM: Synechocystis PCC6803

<400> SEQUENCE: 12
atggtggctc aaactccttc ttctcctcct ctttggttga caatcatcta tttgctgaga      60
tggcataaac ctgctggaag gttgatcttg atgattcctg ctcttttggg ctgtttgcttg    120 gctgctcaag gcttcctcc tcttcctctt cttggaacca ttgctcttgg aactttggca     180
acaagtggct tgggatgtgt ggtgaatgat ctatgggaca gagacattga tcctcaagtg     240
gaaagaacaa agcaaaggcc tcttgctgct agagctttgt cagttcaagt tggaattgga     300
```

```
gttgctttgg tggctcttct ttgtgctgct ggcttggctt tctatttgac accattgagc     360
ttctggcttt gtgttgctgc tgttccagtg attgttgctt atcctggagc taagagggtg     420
tttcctgttc ctcaattggt gctctcaatt gcttggggat tgctgtgct gatttcttgg      480 agtgctgtca ctggagattt gacagatgca acatgggtgc tttggggagc aacagtgttc     540
tggactcttg gctttgacac tgtttatgca atggctgaca gaagatga cagaaggatt       600 ggggtgaact cttcagctct cttctttggc caatatgttg gagaagctgt ggaatcttc      660 tttgctctca ccattggatg cttgttctat tggggatga tcttgatgct taatcctcta      720
tattggctct ctccttgccat tgccattgtt ggatgggtga tccaatacat tcaattgagt   780
gctccaacac cagagccaaa gctctatggc caaattttg dacaaaatgt gatcattgga      840
tttgttcttc ttgctgggat gctgcttgga tggctgtga                            879

<210> SEQ ID NO 13
<211> LENGTH: 618
<212> TYPE: DNA
<213> ORGANISM: Synechocystis PCC6803

<400> SEQUENCE: 13
atggctcaac cattgattct tggagtttct ggagcttctg gcttgattta tgctgtgaga     60
gcaatcaagc atttgttggc tgctgattac accatagagt tggtggcttc aagagcaagc    120
tatcaagttt ggcaagcaga gcaaaacatc cagatgcctg agaaccttc tgctcaagca     180 gaattttgga gaagccaagc tggtgttgag aaaggaggga agctcatttg ccacagatgg    240
ggagatgttg gagcaacaat tgcttctgga agctacagat gtgctggaat ggtggtgctt    300
ccttgctcaa tgagcactgt ggcaaagctg gctgttggaa tgtcttcaga tttgctggag    360
agagctgctg atgttcaaat caaggaagga aagccattgg tggtggttcc aagagaaact    420
cctctctctt tgatccattt gaggaatctc acttcattgg cagaagctgg agtgagaatt    480
gttcctgcaa ttcctgcttg gtatcatcaa cctcaaagtg tggaagattt ggtggatttt    540
gttgttgcaa gagcttttgga tcagctggcc attgattgtg ttcctcttca agatggcaa    600 ggaggaatgg aaggagag                                                   618

<210> SEQ ID NO 14
<211> LENGTH: 1506
<212> TYPE: DNA
<213> ORGANISM: Synechocystis PCC6803

<400> SEQUENCE: 14
atggcaagag atttgagagg cttcattcag ctgttggaaa caagaggcca attgagaagg     60
atcactgctg aagttgatcc agatttggag gttgctgaga tttcaaacag gatgctgcaa    120
gctggtggac ctggcttgct gtttgagaat gtcaagggaa gcccttttcc tgttgctgtg    180
aacttgatgg gaactgtgga aaggatttgc tgggcaatga acatggatca tccattggag    240
ttggaagatt tggggaagaa gctggctctt cttcagcaac caaagccacc aagaagatt    300 tcacaagcta ttgattttgg aaaggttctc tttgatgtgc tgaaggcaaa gcctggaagg    360
aacttcttcc ctccttgcca agaagtggtg attgatgga gaacttggga tctaaaccaa    420
attcctctca tcaggccata tcctggagat gctgggaaga tcatcaccct tggcttggtg    480
atcaccaagg attgtgaaac tggaactcca aatgttggag tttacaggtt gcagctgcaa    540
tcaaagacaa caatgacagt gcattggctc tctgtgagag gaggagcaag gcatttgagg    600
```

| | |
|---|---|
| aaagctgctg agcaagggaa gaagctggag gtggccattg ctcttggagt tgatccatta | 660 |
| atcatcatgg ctgctgcaac accaattcca gtggatctct cagaatggct gtttgctggc | 720 |
| ctctatggag gaagtggagt tgctctagca aaatgcaaaa cagtggattt ggaggttcct | 780 |
| gctgattcag aatttgtgtt ggaaggaacc atcactcctg agagatgct tcctgatggc | 840 |
| cccttggag atcacatggg atattatgga ggagtggaag attcaccatt ggtgaggttc | 900 |
| caatgcttga cccacaggaa gaatccagtt tatttgacaa ctttctctgg aaggccacca | 960 |
| aaggaagaag caatgatggc cattgctctc aacaggatct acactccaat cttgaggcag | 1020 |
| caagtttcag agatcactga tttcttcctc ccaatggaag ctctctccta caaggctgcc | 1080 |
| atcatctcaa ttgacaaggc ttatcctggc caagcaaaga gagctgcttt ggctttctgg | 1140 |
| agtgctcttc ctcaattcac ctacaccaag tttgtgattg tggtggacaa gagcatcaac | 1200 |
| atcagagatc caaggcaagt ggtttgggcc atttcttcca aggttgatcc agtgagagat | 1260 |
| gtcttcattc ttccagaaac accatttgat tctttggatt ttgcttcaga gaagattggc | 1320 |
| ttgggaggaa ggatgggaat tgatgcaaca acaaagattc ctccagaaac agatcatgaa | 1380 |
| tggggagaag tgttggagag tgatccagca atggcagagc aagtttctca agatgggca | 1440 |
| gaatatggct tgggagatat taatttgaca gaggtgaatc caaacctctt tggatatgat | 1500 |
| gtgtaa | 1506 |

<210> SEQ ID NO 15
<211> LENGTH: 1245
<212> TYPE: DNA
<213> ORGANISM: Synechocystis PCC6803

<400> SEQUENCE: 15

| | |
|---|---|
| atgacatttg ttgctgcttc aatcactgac aaccaatttg atgttgccat tgctggtgga | 60 |
| ggagtggttg gcttggtgct tgctgctggc ttgaggcaca ctggcttgaa gattgccatc | 120 |
| attgaagctc ttccaaagga gcaagcattg acaaagcctc aagcatatgc aatttctctt | 180 |
| ctctctggga agattcttgc tggcttggga gtttgggaaa atatcaagga ttcaattggc | 240 |
| cattttgaga ggattcaaat ttcagataat gattacagag gaactgttcc atttgccaag | 300 |
| gaagatgttg atgagctggc tcttggccat gttgctgagc atccagtgat tcttcaagca | 360 |
| ttggagaatt gtgtggagca atgcccaagg attgcttggt tcagaccagc agagttgatt | 420 |
| tcattcactg ctggagagaa ccacaagcaa gtgacattgc agcaagaagg aagagaaatc | 480 |
| actcttcaaa ccaagctgct ggtggctgct gatggagcaa gaagccacac aagatcattg | 540 |
| gctggaatcc aaaccaaagg atggaaatat tggcaaagct gtgtagcttt caccattcag | 600 |
| caccaagctc cagacaacac cactgctttt gaaagatttt gtgacactgg accaatggga | 660 |
| atcttacctc ttcctggaga cagagcacaa attgtttgga caatgcctca ccacaaggct | 720 |
| cacaccttgg tgaatcttcc agaagctgat ttcatcacag agttaaggca aaggattgga | 780 |
| gacaggcttg gagaatttca tctaattaat gcaagaaggt tgtttcctgt tcagttgatg | 840 |
| caaagtgatt gctatgttca accaaggctt gctttggttg gagatgctgc tcattgctgc | 900 |
| caccctgttg gtggccaagg attgaacttg ggaatcagag atggagctgc tttggctcaa | 960 |
| gtgattgcaa ctgctcattc acaaggagaa gattgggaa gtttggctgt gctgaagaga | 1020 |
| tatgagcatt ggaggaagcc agagaattgg ttgattcttg gcttcactga tttgctggac | 1080 |
| agattcttct catctcattg gcttcctgca attgctttga aagatttggc ttggaggtg | 1140 |
| ctgaggttgg tgccaccagc aaagaagctg gctttgaggt tgatgactgg cttgcttgga | 1200 |

| | |
|---|---|
| aggaagcctc agcttgcaac tggccaaagt ttggtttctc agtag | 1245 |

<210> SEQ ID NO 16
<211> LENGTH: 903
<212> TYPE: DNA
<213> ORGANISM: Synechocystis PCC6803

<400> SEQUENCE: 16

| | |
|---|---|
| atggctggct tgtatttgct gacagcaaga ggatatcaaa gctcagattc tgttgcaaat | 60 |
| gcttatgatc aatggacaga gatggaatc ttggaatatt attggggaga tcacattcat | 120 |
| cttggccatt atggagatcc tcctgttgcc aaggatttca tccaaagcaa gatagatttt | 180 |
| gttcatgcaa tggctcaatg gggaggattg gacactcttc ctcctggaac aacagtgctt | 240 |
| gatgttggat gtgaattgg aggaagctca aggatcttgg ccaaggatta tggcttcaat | 300 |
| gtcactggaa tcaccatttc tcctcaacaa gtgaagagag caacagaatt aacaccacca | 360 |
| gatgtcactg caaagtttgc tgttgatgat gcaatggctc tctcatttcc tgatggaagt | 420 |
| tttgatgtgg tttggagtgt ggaagctggt cctcacatgc cagacaaggc tgttttttgcc | 480 |
| aaggagttgc tgagggtggt gaagcctgga ggaatcttgg tggttgctga ttggaatcaa | 540 |
| agagatgaca ggcaagttcc tctcaacttc tgggagaagc cagtgatgag caattgctg | 600 |
| gatcaatgga ccacccctgc ttttgcttca attgaaggat tgctgagaa cttggaagca | 660 |
| actggcttgg tggaaggcca agtgacaact gctgattgga ctgttccaac tcttcctgct | 720 |
| tggttggaca ccatttggca aggaatcatc aggcctcaag gatggctgca atatggaatc | 780 |
| agaggcttca tcaaatcagt gagagaagtt ccaaccatct gctgatgag gcttgctttt | 840 |
| ggagttgggc tttgcaggtt tggaatgttc aaggctgtga gaaaaaatgc aacacaagcc | 900 |
| taa | 903 |

<210> SEQ ID NO 17
<211> LENGTH: 951
<212> TYPE: DNA
<213> ORGANISM: Synechocystis PCC6803

<400> SEQUENCE: 17

| | |
|---|---|
| atggtttacc atgtgaggcc aaagcatgct ctcttcttgg ctttctattg ctacttctct | 60 |
| ctgctgacaa tggcttcagc aaccattgct tctgctgatc tctatgaaaa aattaaaaac | 120 |
| ttctatgatg attcttctgg cttgtgggaa gatgtttggg agagcacat gcaccatgga | 180 |
| tattatggcc ctcatggaac ctacaggatt gacagaaggc aagctcaaat tgatttgatc | 240 |
| aaagagctat ggcttgggc tgttcctcaa aatagcgcaa agccaaggaa gatcttggat | 300 |
| cttggatgtg gaattggagg aagctctctc tatttggctc agcagcatca agcagaggtg | 360 |
| atgggagctt ctctctcacc agtgcaagtt gaaagagctg agaaagagc aagagctttg | 420 |
| gggcttggtt ctacttgcca attccaagtg gcaaatgctt tggatcttcc atttgcttca | 480 |
| gattcctttg attgggtttg gagcttggag agtggagagc acatgccaaa caaggctcaa | 540 |
| tttcttcaag aagcatggag ggtgctgaag cctggaggaa ggttgatctt ggcaacttgg | 600 |
| tgccacaggc caattgatcc tggaaatggc cctctcactg ctgatgaaag aaggcatctt | 660 |
| caagcaatct atgatgttta ttgcttgcca tatgtggttt cattgccaga ttatgaagcc | 720 |
| attgcaagag aatgtggctt tggagaaatt aagactgctg attggagtgt tgctgttgct | 780 |
| ccatttgggg acagggtgat tgaatcagct tttgatccaa gggtgctttg ggctcttggt | 840 |

| caagctgggc caaagatcat caatgctgct ctctgcttga gattaatgaa atggggatat | 900 |
| gaaagaggct tggtgaggtt tggcttgctc actggaatca agccactggt g | 951 |

<210> SEQ ID NO 18
<211> LENGTH: 795
<212> TYPE: DNA
<213> ORGANISM: Synechocystis PCC6803

<400> SEQUENCE: 18

| atgaagaaga atgtttacta ttccaagatt gctgacatct atgatcaaac aaggtggatg | 60 |
| acagaaccaa ttgctgaaga agttgctgat tcatcctgg ctttggtgaa ggcaacaagg | 120 |
| gaaacaacct tcctggagcc tggtgttgga actggcttga atgtgatccc tctggtgagg | 180 |
| agaggatatt cagtcactgg agtggacatc tctcaagaga tgctctctca attttctcaa | 240 |
| aagctgccaa ggattcctcc aaacttgagg ctgatccatg aagatgcaag ccagctgagc | 300 |
| ttcccagatt cttcctttga tgtggtgctc actgtgcaca tgctgcattc tgtttcaaac | 360 |
| ttggggatgt tcctggatga gattgacagg gtgctgaagc aaatggcttc tacttgaat | 420 |
| gctcaatggg tgacaccacc agctcacctg gagtttgaga accacttcaa gaccatcttg | 480 |
| ctgaagtacc aagagccaaa gccctcacag caaagtttgg aggtcaccaa caagatcaac | 540 |
| attgatgaat atctgctgaa caaaggctac caatgcaact acttgacagc caaggaatgg | 600 |
| acagtttcaa accaagtgca agagctgctg catttctaca gaagccatgc ttatggcttg | 660 |
| tgctggctgc ttcctgatga agccttcaac ttggccatca aggagtttga ggtgttctgc | 720 |
| tatgaatatt atgattccct caaggtggag ctttcaagcc aagctcagtt tgagatttgg | 780 |
| gcctacactg tgaag | 795 |

<210> SEQ ID NO 19
<211> LENGTH: 810
<212> TYPE: DNA
<213> ORGANISM: Synechocystis PCC6803

<400> SEQUENCE: 19

| atgacatatt tgcttcaga tttccaagat ttggacaaca gtggcaacat tgagaacttc | 60 |
| atcagatgct tggagctgca acaaagtttg gatctctaca aatactacaa gcagaagacc | 120 |
| tttgagaaga tgcagctgaa gcctggagat tcagtgctgg aggttggatg tggaactgga | 180 |
| aatgatgctc ttcttctggc caactatgtt ggagaaactg ggaaggtgac tgctgtggac | 240 |
| agaagccaat tcatgctgga tcaagcaaga gaaagagcca agaactcaac aaccaagttt | 300 |
| gagtttgtgc tagctgatgc tgagcagctt cccttccctg agcaaacctt cactgctgca | 360 |
| agggtggaca gaaccctcca gcacattgct cagcctcaga aggccattgc tgagatggca | 420 |
| agggtggtgc aaagcaatgg atgggtggtg gcttttgagc cagattggga aaccttggtg | 480 |
| attgattcag atcaaagagg agtgacaaga gccatcacca acttctggtg tgacaacttc | 540 |
| ccttctggat gggtgggaag atatctcttc aaatacttca gacaagctgg cttgacagac | 600 |
| attgctgttg atccaatcac catttgcttg acagagtttg agcttgctga taaaatttg | 660 |
| gatctctcaa ggacagtgga aaaaattttct gagcaaggaa ccatctctca gaatgatttg | 720 |
| acccttggt tcaaggccat tgatcagaat gatcaagctg gagagttctt ctgtgccttc | 780 |
| actgccttct tggtgagagg aaggaagcca | 810 |

<210> SEQ ID NO 20
<211> LENGTH: 639

<212> TYPE: DNA
<213> ORGANISM: Synechocystis PCC6803

<400> SEQUENCE: 20

```
atggcaacaa tcttcagaac ttggagctac caatatccat gggtttatgc tttggtttca      60
aggttggcaa cattgaatgt tggaggagaa gaaaggttcc accagcttcc tttggagaac     120
ttggctatct ctcctggcca gaaggtgctt gatctttgct gtggaggagg ccaagcaaca     180
gtttacttgg ctcaaagtgg agcaacagtg gttggcttgg atgcttcacc aaaggctctt     240
ggaagagcaa aaattaatgt tcctcaagca acatatgttc aaggattagc agaagatctt     300
ccatttggag aaggagaatt tgatttggtg cacacttctg ttgctcttca tgagatgaca     360
ccagctcagc tgcaaagcat catcagtgga gttcacaggg tgctgaagcc tggaggaatc     420
tttgctttgg tggatcttca caggccttca aattggctct tctggccacc cttggcaatt     480
ttcatgggat tgtttgaaac agaaactgct tggcagctaa ttaacacaga tttgggaagt     540
ttgctggatc aagctggctt cactgtggtg agaaagcatt tgtatgctgg aggaagtttg     600
caagtgatcc aagcaagagc caacaagaca gtgaactaa                            639
```

<210> SEQ ID NO 21
<211> LENGTH: 12
<212> TYPE: PRT
<213> ORGANISM: Artificial Sequence
<220> FEATURE:
<223> OTHER INFORMATION: Linker peptide

<400> SEQUENCE: 21

Gly Ser Ala Gly Ser Ala Ala Gly Ser Gly Glu Phe
1               5                   10

<210> SEQ ID NO 22
<211> LENGTH: 192
<212> TYPE: PRT
<213> ORGANISM: Synechocystis PCC6803

<400> SEQUENCE: 22

Met Leu Val Lys Ile Leu Lys Phe Arg Arg Phe Ile Met Thr Gln Ile
1               5                   10                  15

Ser Gly Ser Pro Asp Val Pro Asp Leu Gly Arg Arg Gln Phe Met Asn
                20                  25                  30

Leu Leu Thr Phe Gly Thr Ile Thr Gly Val Ala Ala Gly Ala Leu Tyr
            35                  40                  45

Pro Ala Val Lys Tyr Leu Ile Pro Ser Ser Gly Gly Ser Gly Gly Gly
        50                  55                  60

Gly Val Thr Ala Lys Asp Ala Leu Gly Asn Asp Val Lys Val Thr Glu
65                  70                  75                  80

Phe Leu Ala Ser His Asn Ala Gly Asp Arg Val Leu Ala Gln Gly Leu
                85                  90                  95

Lys Gly Asp Pro Thr Tyr Ile Val Val Gln Gly Asp Asp Thr Ile Ala
                100                 105                 110

Asn Tyr Gly Ile Asn Ala Val Cys Thr His Leu Gly Cys Val Val Pro
            115                 120                 125

Trp Asn Ala Ser Glu Asn Lys Phe Met Cys Pro Cys His Gly Ser Gln
        130                 135                 140

Tyr Asn Ala Glu Gly Lys Val Val Arg Gly Pro Ala Pro Leu Ser Leu
145                 150                 155                 160

Ala Leu Ala His Ala Thr Val Thr Asp Asp Asp Lys Leu Val Leu Ser

```
                    165                 170                 175
Thr Trp Thr Glu Thr Asp Phe Arg Thr Asp Glu Asp Pro Trp Trp Ala
                180                 185                 190

<210> SEQ ID NO 23
<211> LENGTH: 579
<212> TYPE: DNA
<213> ORGANISM: Synechocystis PCC6803

<400> SEQUENCE: 23
atgttagtaa aaatccttaa atttagacgg ttcattatga cacagatttc tggctcccct       60
gatgtcccng atttgggtcg gcgtcagttt atgaacttat tgaccttcgg tacgatcact      120
ggggtggcgg ccggggccct ctatccagca gtaaaatatt tgatcccccc ctccagtggt      180
ggttcgggcg gtggtgtaac ggccaaagat gcccttggta atgatgttaa ggtgacggaa      240
tttttggctt cccataacgc tggcgatcgg gtgttggccc aggggttgaa gggcgacccg      300
acctatattg tagtccaggg ggatgacacg atcgccaact atggtattaa tgcggtgtgt      360
acccatttgg gctgtgtagt gccctggaat gccagcgaaa acaaatttat gtgcccttgt      420
cacggctccc agtacaacgc tgaaggtaaa gtggtccgtg gcccggctcc cctctctttg      480
gctttggccc acgctaccgt taccgacgac gacaaattag tgctcagcac ctggaccgaa      540
accgatttcc gcaccgacga agatccctgg tgggcttag                             579
```

HERBICIDE TOLERANT PLANTS EXPRESSING A CYANOBACTERIAL PLASTOQUINONE BIOSYNTHETIC PATHWAY

CROSS REFERENCE TO RELATED APPLICATIONS

This application is a national stage application under 35 U.S.C. § 371 of PCT/US2019/037295, filed Jun. 14, 2019, which claims the benefit of U.S. Provisional Application Ser. No. 62/691,629 filed Jun. 29, 2018, the contents of which are herein incorporated by reference in their entirety.

REFERENCE TO SEQUENCE LISTING SUBMITTED ELECTRONICALLY

The official copy of the sequence listing is submitted electronically via EFS-Web as an ASCII formatted sequence listing with a file named "PF181434PCT_Sequence_Listing.txt", created on Jun. 14, 2019, and having a size of 41 kilobytes and is filed concurrently with the specification. The sequence listing contained in this ASCII formatted document is part of the specification and is herein incorporated by reference in its entirety.

FIELD OF THE INVENTION

This invention relates to plant molecular biology, particularly generation of recombinant soybean plants demonstrating improved tolerance to herbicides.

BACKGROUND OF THE INVENTION

The 4-hydroxyphenylpyruvate dioxygenases (HPPDs) are enzymes which catalyze the reaction in which para-hydroxyphenylpyruvate (abbreviated herein as HPP), a tyrosine degradation product, is transformed into homogentisate (abbreviated herein as HG), the precursor in plants of tocopherol and plastoquinone (Crouch N. P. et al. (1997), Tetrahedron, 53, 20, 6993-7010, Fritze et al. (2004), Plant Physiology 134:1388-1400). Tocopherol acts as a membrane-associated antioxidant. Plastoquinone, firstly acts as an electron carrier between PSII and the cytochrome b6/f complex and secondly, is a redox cofactor for phytoene desaturase, which is involved in the biosynthesis of carotenoids.

Up to now, more than 1000 nucleic acid sequences from various organisms present in the NCBI database were annotated as coding for a putative protein having an HPPD domain. But for most of those, it has not been proven that the protein would have an HPPD enzymatic activity either in an in vitro assay or in an in planta approach, nor that such HPPD protein can confer herbicide tolerance to HPPD inhibitor herbicides when expressed in a plant. Several HPPD proteins and their primary sequences have been described in the state of the art, in particular the HPPD proteins of bacteria such as *Pseudomonas* (Rüetschi et al., Eur. J. Biochem., 205, 459-466, 1992, WO96/38567), Kordia (WO2011/076889) *Synechococcus* (WO2011/076877), and *Rhodococcus* (WO2011/076892), of protists such as *Blepharisma* (WO2011/076882), of euryarchaeota such as *Picrophilus* (WO2011/076885) of plants such as *Arabidopsis* (WO96/38567, GENBANK® AF047834), carrot (WO 96/38567, GENBANK® 87257), *Avena sativa* (WO2002/ 046387, WO2011/068567), wheat (WO2002/046387), *Brachiaria platyphylla* (WO2002/046387), *Cenchrus echinatus* (WO2002/046387), *Lolium rigidum* (WO2002/046387), *Festuca arundinacea* (WO2002/046387), *Setaria faberi* (WO 2002/046387), *Eleusine indica* (WO2002/046387), *Sorghum* (WO2002/046387, WO2012/021785), corn (WO2012/021785), Coccicoides (GENBANK® COITRP), of *Coptis japonica* (WO2006/132270), *Chlamydomonas reinhardtii* (ES 2275365; WO2011/145015), or of mammals such as mouse or pig.

Inhibition of HPPD leads to uncoupling of photosynthesis, deficiency in accessory light-harvesting pigments and, most importantly, to destruction of chlorophyll by UV-radiation and reactive oxygen species (bleaching) due to the lack of photo protection normally provided by carotenoids (Norris et al. (1995), Plant Cell 7: 2139-2149). Bleaching of photosynthetically active tissues leads to growth inhibition and plant death.

Some molecules which inhibit HPPD, and which inhibit transformation of the HPP into homogentisate while binding specifically to the enzyme, have proven to be very effective herbicides.

At present, most commercially available HPPD inhibitor herbicides belong to one of these chemical families:

1) the triketones, e.g. sulcotrione [i.e. 2-[2-chloro-4-(methylsulfonyl)benzoyl]-1,3-cyclohexanedione], mesotrione [i.e. 2-[4-(methylsulfonyl)-2-nitrobenzoyl]-1,3-cyclohexanedione]; tembotrione [i.e. 2-[2-chloro-4-(methylsulfonyl)-3-[(2,2,2,-tri-fluoroethoxy)methyl]benzoyl]-1,3-cyclo-hexanedione]; tefuryltrione [i.e. 2-[2-chloro-4-(methylsulfonyl)-3-[[(tetrahydro-2-furanyl)methoxy]methyl]benzoyl]-1,3-cyclohexanedione]]; bicyclopyrone [i.e. 4-hydroxy-3-[[2-[(2-methoxyethoxy)methyl]-6-(trifluoromethyl)-3-pyridinyl]carbonyl]bicyclo[3.2.1]oct-3-en-2-one]; Benzobicyclon [i.e. 3-(2-chloro-4-mesylbenzoyl)-2-phenylthiobicyclo[3.2.1]oct-2-en-4-one];
2) the diketonitriles, e.g. 2-cyano-3-cyclopropyl-1-(2-methylsulphonyl-4-trifluoromethylphenyl)-propane-1,3-dione and 2-cyano-1-[4-(methylsulphonyl)-2-trifluoromethylphenyl]-3-(1-methylcyclopropyl)propane-1,3-dione;
3) the isoxazoles, e.g. isoxaflutole [i.e. (5-cyclopropyl-4-isoxazolyl)[2-(methylsulfonyl)-4-(trifluoromethyl)phenyl]methanone]. In plants, isoxaflutole is rapidly metabolized in DKN, a diketonitrile compound which exhibits the HPPD inhibitor property;
4) the pyrazolinates, e.g. topramezone [i.e. [3-(4,5-dihydro-3-isoxazolyl)-2-methyl-4-(methylsulfonyl) phenyl](5-hydroxy-1-methyl-1H-pyrazol-4-yl)methanone], and pyrasulfotole [i.e. (5-hydroxy-1,3-dimethylpyrazol-4-yl(2-mesyl-4-trifluaromethylphenyl)methanone]; pyrazofen [i.e. 2-[4-(2,4-dichlorobenzoyl)-1,3-dimethylpyrazol-5-yloxy]acetophenone];
5) N (1,2,5-oxadiazol-3-yl)benzamides (WO2011/035874) and N-(1,3,4-oxadiazol-2-yl)benzamides (WO2012/126932), e.g. 2-methyl-N-(5-methyl-1,3,4-oxadiazol-2-yl)-3-(methylsulfonyl)-4-(trifluoromethyl)benzamide (hereinafter also named "Cmpd. 1");
6) N-(tetrazol-5-yl)- or N-(triazol-3-yl)arylcarboxamides (WO2012/028579), e.g. 2-chloro-3-ethoxy-4-(methylsulfonyl)-N-(1-methyl-1H-tetrazol-5-yl)benzamide (hereinafter also named "Cmpd.2"); 4-(difluoromethyl)-2-methoxy-3-(methylsulfonyl)-N-(1-methyl-1H-tetrazol-5-yl)benzamide (hereinafter also named "Cmpd. 3"); 2-chloro-3-(methylsulfanyl)-N-(1-methyl-1H-tetrazol-5-yl)-4-(trifluoromethyl)benzamide (hereinafter also named "Cmpd. 4"); 2-(methoxymethyl)-3-

(methylsulfinyl)-N-(1-methyl-1H-tetrazol-5-yl)-4-(trifluoromethyl)benzamide (hereinafter also named "Cmpd. 5");

7) Pyridazinone derivatives as described in WO2013/050421 and WO2013/083774;
8) Substituted 1,2,5-oxadiazoles as described in WO2013/072300 and WO2013/072402; and
9) Oxoprazin derivatives as described in WO2013/054495.

These HPPD inhibitor herbicides can be used against grass and/or broad leaf weeds in fields of crop plants that display metabolic tolerance, such as maize (*Zea mays*), rice (*Oryza sativa*) and wheat (*Triticum aestivum*) in which they are rapidly degraded (Schulz et al. (1993), FEBS letters, 318, 162-166; Mitchell et al. (2001), Pest Management Science, Vol 57, 120-128; Garcia et al. (2000), Biochem., 39, 7501-7507; Pallett et al. (2001), Pest Management Science, Vol 57, 133-142). In order to extend the scope of use of these HPPD inhibitor herbicides, several efforts have been developed in order to confer to plants, particularly plants without or with an underperforming metabolic tolerance, a tolerance level acceptable under agronomic field conditions.

Besides the attempt of by-passing HPPD-mediated production of homogentisate (U.S. Pat. No. 6,812,010), overexpressing the sensitive enzyme so as to produce quantities of the target enzyme in the plant which are sufficient in relation to the herbicide has been performed (WO96/38567). Overexpression of HPPD resulted in better pre-emergence tolerance to the diketonitrile derivative (DKN) of isoxaflutole (IFT), but the tolerance level was not sufficient for tolerance to post-emergence treatment (Matringe et al. (2005), Pest Management Science 61: 269-276).

A third strategy was to mutate the HPPD in order to obtain a target enzyme which, while retaining its properties of catalyzing the transformation of HPP into homogentisate, was less sensitive to HPPD inhibitors than the native HPPD before mutation.

This strategy has been successfully applied for the production of plants tolerant to 2-cyano-3-cyclopropyl-1-(2-methylsulphonyl-4-trifluoromethylphenyl)-propane-1,3-dione and to 2-cyano-1-[4-(methylsulphonyl)-2-trifluoromethylphenyl]-3-(1-methylcyclopropyl)propane-1,3-dione (EP496630), two HPPD inhibitor herbicides belonging to the diketonitriles family (WO99/24585). Pro215Leu, Gly336Glu, Gly336Ile, and more particularly Gly336Trp (positions of the mutated amino acid are indicated with reference to the *Pseudomonas fluorescens* HPPD) were identified as mutations which are responsible for an increased tolerance to treatment with these diketonitrile herbicides.

More recently, introduction of a *Pseudomonas fluorescens* HPPD gene into the plastid genome of tobacco and soybean was shown to be more effective than nuclear transformation, conferring tolerance to post-emergence application of isoxaflutole (Dufourmantel et al. (2007), Plant Biotechnol J.5(1):118-33).

In WO2004/024928, the inventors sought to increase the prenylquinone biosynthesis (e.g., synthesis of plastoquinones, tocopherols) in the cells of plants by increasing the flux of the HPP precursor into the cells of these plants. This was done by connecting the synthesis of said precursor to the "shikimate" pathway by overexpression of a prephenate dehydrogenase (PDH) enzyme. They also noted that the transformation of plants with a gene encoding a PDH enzyme and a gene encoding an HPPD enzyme makes it possible to increase the tolerance of said plants to HPPD inhibitors.

In WO2009/144079, nucleic acid sequences encoding a HPPD with specific mutations at position 336 of the *Pseudomonas fluorescens* HPPD protein and their use for obtaining plants which are tolerant to HPPD inhibitor herbicides was disclosed.

In WO2002/046387, several domains of HPPD proteins originating from plants were identified that may be relevant to confer tolerance to various HPPD inhibitor herbicides, but neither in planta nor biochemical data were shown to confirm the impact of the as described domain functions.

In WO2008/150473, the combination of two distinct tolerance mechanisms—a modified *Avena sativa* gene coding for a mutant HPPD enzyme and a CYP450 Maize monooxygenase (nsf1 gene) —was exemplified in order to obtain an improved tolerance to HPPD inhibitor herbicides, but no data were disclosed demonstrating the synergistic effects based on the combination of both proteins.

Further, in US2011/0173718, a method to generate plants tolerant to HPPD inhibitors by overexpressing not only a gene coding for a tolerant HPPD, as for example from *Avena sativa*, but also in combination with several plant genes coding for an HST (homogentisate solanesyltransferase) protein was disclosed. However, the level of tolerance to selected HPPD inhibitor herbicides was rather limited.

In WO2011/094199 and US2011/0185444, the tolerance of several hundreds of soybean wild type lines to the HPPD inhibitor isoxaflutole was evaluated. Very few lines displayed reasonable levels of tolerance to the herbicides. The putative QTL (quantitative trait loci) responsible for the tolerance was identified. In this region of the genome, a gene coding for an ABC transporter was identified as being the main trait responsible for the improved tolerance to the HPPD inhibitor herbicide observed. However, transgenic plants expressing the identified genes did not display any improvement in tolerance to the tested HPPD inhibitor herbicides.

In WO2010/085705, several mutants of the *Avena sativa* HPPD were disclosed. It was shown that some of the variants displayed improved tolerance in vitro to the triketone "mesotrione", however, only very few mutants were expressed in tobacco plants. Additionally, none of the tobacco plants expressing these mutants displayed improved tolerance to mesotrione or isoxaflutole compared to tobacco plants expressing the wild type *Avena sativa* HPPD gene.

US 2012/0042413 describes polypeptides having HPPD activity but also showing a certain insensitivity to at least one HPPD inhibitor and further suggests a certain set of mutations at different positions of HPPD enzymes and finally discloses biochemical data, as well as tolerance levels, of plants containing few of such mutated HPPDs. In EP 2453012, several mutants of HPPD were described; however, the improved tolerance of the described mutants was not demonstrated in planta against several HPPD inhibitor herbicides.

WO2014/043435 describes mutant HPPD enzymes derived from the native *Pseudomonas fluorescens* HPPD nucleotide sequence (Pf-HPPD, 1077 bp, as described in WO2009/144079) having HPPD activity with broad tolerance to HPPD inhibitor herbicides as demonstrated by biochemical data and tolerance levels of plant containing several of the disclosed Pf-HPPD mutant enzymes.

SUMMARY OF THE INVENTION

Compositions and methods for conferring tolerance to HPPD inhibitor herbicides are provided.

Disclosed herein is a method of generating a plant having resistance to an HPPD inhibitor herbicide, the methods comprising expressing one or more exogenous polypeptides in the plant, the exogenous polypeptides being sufficient to catalyze the production of plastoquinone-9 (PQ9) when the plant is cultivated in the presence of an effective amount of an HPPD inhibitor herbicide. In some embodiments, the exogenous polypeptides are sufficient to catalyze the production of 2-solanesyl-1,4-benzoquinol when the plant is cultivated in the presence of an effective amount of an HPPD inhibitor herbicide, and wherein PQ9 is catalyzed from the 2-solanesyl-1,4-benzoquinol by the action of endogenous and/or exogenous polypeptides (such as one or more methyltransferase(s)). In other embodiments, the exogenous polypeptides are derived from a non-plant PQ9 catalytic pathway (such as derived from a cyanobacterial PQ9 pathway). In an embodiment, the exogenous peptide(s) are selected from the group consisting of a UbiC polypeptide, a UbiA polypeptide, a UbiX polypeptide, a UbiD polypeptide, a UbiH polypeptide, a Sll0418 polypeptide, a slr0089 polypeptide, a sll1407 polypeptide, a slr0407 polypeptide, and/or a sll0829 polypeptide.

Also disclosed herein is an isolated nucleic acid molecule comprising (a) one or more coding regions, each comprising one or more nucleic acid sequences encoding one or more polypeptides of non-plant origin selected from the group consisting of a chorismate lyase or a component thereof, a 4-hydroxybenzoate solanesyltransferase or a component thereof, a 4-hydroxy-3-prenylbenzoate decarboxylase or a component thereof, a hydroxylase or a component thereof, and a methyltransferase or a component thereof; and (b) one or more control regions sufficient to drive expression of said polypeptides when present in a plant. In an embodiment, the isolated nucleic acid comprises each of the nucleic acid sequence encoding the chorismate lyase or the component thereof, the nucleic acid sequence encoding the 4-hydroxybenzoate solanesyltransferase or the component thereof, the nucleic acid sequence encoding the 4-hydroxy-3-prenylbenzoate decarboxylase or the component thereof, and the nucleic acid sequence encoding the hydroxylase or the component thereof, and optionally further comprises the nucleic acid sequence encoding the methyltransferase or the component thereof. In another embodiment, the chorismate lyase, the 4-hydroxybenzoate solanesyltransferase, the 4-hydroxy-3-prenylbenzoate decarboxylase, the hydroxylase, and/or the methyltransferase(s) (or the components thereof) are derived from a cyanobacterial PQ9 catalytic pathway. In an embodiment, one or more polypeptides of non-plant origin is/are selected from the group consisting of a UbiC polypeptide, a UbiA polypeptide, a UbiX polypeptide, a UbiD polypeptide, a UbiH polypeptide, a Sll0418 polypeptide, a slr0089 polypeptide, a sll1407 polypeptide, a slr0407 polypeptide, and a sll0829 polypeptide.

Also disclosed herein is a chimeric gene comprising the following operably linked DNA: (a) a plant-expressible promoter; (b) a DNA region which when transcribed yields one or more mRNA molecules encoding one of more polypeptides of non-plant origin selected from the group consisting of a chorismate lyase or a component thereof, a 4-hydroxybenzoate solanesyltransferase or a component thereof, a 4-hydroxy-3-prenylbenzoate decarboxylase or a component thereof, a hydroxylase or a component thereof, and a methyltransferase or a component thereof. In another embodiment, the DNA region of (b) yields one or more mRNA molecules encoding each of the chorismate lyase or the component thereof, the 4-hydroxybenzoate solanesyltransferase or the component thereof, the 4-hydroxy-3-prenylbenzoate decarboxylase or the component thereof, and the hydroxylase or the component thereof. In another embodiment, the DNA region of (b) yields one or more mRNA molecules encoding each of the chorismate lyase or the component thereof, the 4-hydroxybenzoate solanesyltransferase or the component thereof, the 4-hydroxy-3-prenylbenzoate decarboxylase or the component thereof, the hydroxylase or the component thereof, and the methyltransferase or the component thereof. In another embodiment, the chorismate lyase, the 4-hydroxybenzoate solanesyltransferase, the 4-hydroxy-3-prenylbenzoate decarboxylase, the hydroxylase, and/or the methyltransferase(s) (or the components thereof) are derived from a cyanobacterial PQ9 catalytic pathway. In an embodiment, the one or more polypeptides of non-plant origin is/are selected from the group consisting of a UbiC polypeptide, a UbiA polypeptide, a UbiX polypeptide, a UbiD polypeptide, a UbiH polypeptide, a Sll0418 polypeptide, a slr0089 polypeptide, a sll1407 polypeptide, a slr0407 polypeptide, and a sll0829 polypeptide. In an embodiment, the one or more polypeptides of non-plant origin is/are selected from the group consisting of a UbiC polypeptide having at least 75% sequence identity to SEQ ID NO: 1, a UbiA polypeptide at least 75% sequence identity to SEQ ID NO: 2, a UbiX polypeptide having at least 75% sequence identity to SEQ ID NO: 3, a UbiD polypeptide having at least 75% sequence identity to SEQ ID NO: 4, a UbiH polypeptide having at least 75% sequence identity to SEQ ID NO: 5, a Sll0418 polypeptide having at least 75% sequence identity to SEQ ID NO: 6, a slr0089 polypeptide having at least 75% sequence identity to SEQ ID NO: 7, a sll1407 polypeptide having at least 75% sequence identity to SEQ ID NO: 8, a slr0407 polypeptide having at least 75% sequence identity to SEQ ID NO: 9, and a sll0829 polypeptide having at least 75% sequence identity to SEQ ID NO: 10. In an embodiment, the one or more polypeptides of non-plant origin is/are selected from the group consisting of a UbiC polypeptide comprising SEQ ID NO: 1, a UbiA polypeptide comprising SEQ ID NO: 2, a UbiX polypeptide comprising SEQ ID NO: 3, a UbiD polypeptide comprising SEQ ID NO: 4, a UbiH polypeptide comprising SEQ ID NO: 5, a Sll0418 polypeptide comprising SEQ ID NO: 6, a slr0089 polypeptide comprising SEQ ID NO: 7, a sll1407 polypeptide comprising SEQ ID NO: 8, a slr0407 polypeptide comprising SEQ ID NO: 9, and a sll0829 polypeptide comprising SEQ ID NO: 10. In yet another embodiment of the invention, a plant cell, plant or seed comprising the chimeric gene described above is provided. In yet another embodiment, transformed plants, plant cells, tissues, and seeds that are tolerant to HPPD inhibitor herbicides by the introduction of the nucleic acids into the plants, plant cells, tissues, and seeds are also provided herein.

DETAILED DESCRIPTION OF THE INVENTION

Figure 1:
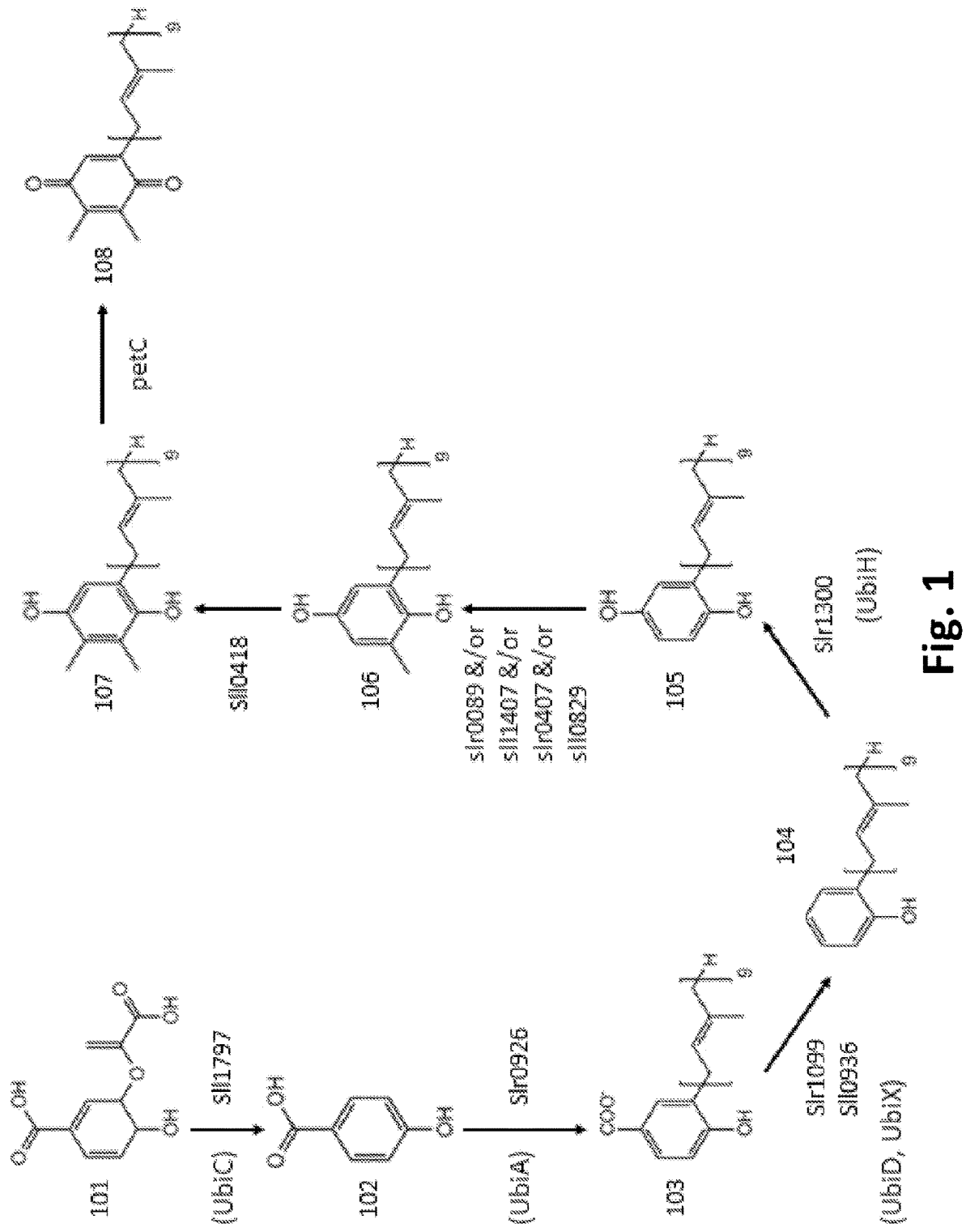
FIG. 1 is a schematic example of the plastoquinone-9 (PQ9) synthetic pathway. In this pathway, chorismate (101) (CHA) is converted to 4-hydroxybenzoate (102) (PHB) by chorismate lyase (e.g., EC 4.1.3.40); PHB is then converted to 4-hydroxy-3-solanesylbenzoate (103) (NHB) by 4-hydroxybenzoate solanesyltransferase (e.g., EC 2.5.1._); NHB is converted to 2-solanesylphenol (104) (NPP) by at least one 4-hydroxy-3-prenylbenzoate decarboxylase (e.g., EC 4.1.1.98); NPP is then converted to 2-solanesyl-1,4-benzoquinol (105) (SBQ) by solanesylphenol hydroxylase (e.g., EC 1.14.13). The enzymes performing these four conversions of CHA to SBQ are cyanobacterial, preferably of *Synechocystis* sp., transgenically expressed in a plant or plant cell. The final three steps can be performed by enzymes that are either endogenous to the plant cells or are exogenous (cyanobacterial or *Synechocystis*). In those three steps, MPBQ/MSBQ methyltransferase(s) (e.g., EC 2.1.1.295) convert SBQ to 2-methyl-6-solanesyl-1,4-benzoquinol (106) (MSBQ) and then convert MSBQ to 2,3-dimethyl-6-solanesyl-1,4-benzoquinol (107) (DMSBQ), i.e. plastoquinol-9 (PQH2). Finally, plastoquinol-plastocyanin reductase (e.g., EC 1.10.9.1) converts PQH2 to plastoquinone-9 (108) (PQ9).

The present inventions now will be described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

A. Overview

Several efforts have been developed in order to confer to plants an agronomically-acceptable level of tolerance to a broad range of HPPD inhibitor herbicides, including bypassing HPPD-mediated production of homogentisate (U.S. Pat. No. 6,812,010), overexpressing the sensitive enzyme so as to produce quantities of the target enzyme in the plant which are sufficient in relation to the herbicide (WO96/38567), and mutating the HPPD in order to obtain a target enzyme which, while retaining its properties of catalyzing the transformation of HPP into homogentisate, is less sensitive to HPPD inhibitors than is the native HPPD before mutation.

Despite these successes obtained for the development of plants showing tolerance to several HPPD inhibitors herbicides described above, it is still necessary to develop and/or improve the tolerance of plants to newer or to several different HPPD inhibitors, particularly HPPD inhibitors belonging to the classes of the triketones (e.g. sulcotrione, mesotrione, tembotrione, benzobicyclone and bicyclopyrone), the pyrazolinates (e.g., topramezone and pyrasulfotole), N-(1,2,5-Oxadiazol-3-yl)benzamides (WO 2011/035874), and N-(tetrazol-4-yl)- or N-(triazol-3-yl) arylcarboxamides (WO2012/028579).

The present disclosure provides improved compositions and methods for regulating HPPD inhibitor herbicide tolerance. The inventors of the present disclosure surprisingly found that expression of one or more polypeptide elements of an exogenous PQ synthetic pathway that bypass HPPD-mediated homogentisate production in soybean resulted in an improvement in herbicide tolerance to HPPD inhibitors.

B. Terms

As used herein, the singular form "a", "an" and "the" includes plural references unless the context clearly dictates otherwise. For example, the term "a cell" includes a plurality of cells, including mixtures thereof.

As used herein, the term "gene" refers to a DNA sequence involved in producing a RNA or polypeptide or precursor thereof. The polypeptide or RNA can be encoded by a full-length coding sequence or by intron-interrupted portions of the coding sequence, such as exon sequences.

As used herein, the term "oligonucleotide" refers to a molecule comprising a plurality of deoxyribonucleotides or ribonucleotides. Oligonucleotides may be generated in any manner, including chemical synthesis, DNA replication, reverse transcription, polymerase chain reaction, or a combination thereof. In one embodiment, the present invention embodies utilizing the oligonucleotide in the form of dsRNA as means of interfering with the expression of one or more HPPR enzymes. Inasmuch as mononucleotides are synthesized to construct oligonucleotides in a manner such that the 5' phosphate of one mononucleotide pentose ring is attached to the 3' oxygen of its neighbor in one direction via a phosphodiester linkage, an end of an oligonucleotide is referred to as the "5' end" if its 5' phosphate is not linked to the 3' oxygen of a mononucleotide pentose ring and as the "3' end" if its 3' oxygen is not linked to a 5' phosphate of a subsequent mononucleotide pentose ring. As used herein, a nucleic acid sequence, even if internal to a larger oligonucleotide, also may be said to have 5' and 3' ends.

When two different, non-overlapping oligonucleotides anneal to different regions of the same linear complementary nucleic acid sequence, and the 3' end of one oligonucleotide points towards the 5' end of the other, the former may be called the "upstream" oligonucleotide and the latter the "downstream" oligonucleotide.

As used herein, the term "primer" refers to an oligonucleotide, which is capable of acting as a point of initiation of synthesis when placed under conditions in which primer extension is initiated. An oligonucleotide "primer" may occur naturally, as in a purified restriction digest or may be produced synthetically.

A primer is selected to be "substantially complementary" to a strand of specific sequence of the template. A primer must be sufficiently complementary to hybridize with a template strand for primer elongation to occur. A primer sequence need not reflect the exact sequence of the template. For example, a non-complementary nucleotide fragment may be attached to the 5' end of the primer, with the remainder of the primer sequence being substantially complementary to the strand. Non-complementary bases or longer sequences can be interspersed into the primer, provided that the primer sequence is sufficiently complementary with the sequence of the template to hybridize and thereby form a template primer complex for synthesis of the extension product of the primer.

The term "chimeric" when referring to a gene or DNA sequence is used to refer to a gene or DNA sequence comprising at least two functionally relevant DNA fragments (such as promoter, 5'UTR, coding region, 3'UTR, intron) that are not naturally associated with each other.

For the purpose of this disclosure, the "sequence identity" of two related nucleotide or amino acid sequences, expressed as a percentage, refers to the number of positions in the two optimally aligned sequences which have identical residues (×100) divided by the number of positions compared. A gap, i.e., a position in an alignment where a residue is present in one sequence but not in the other is regarded as a position with non-identical residues. The alignment of the two sequences is performed by the Needleman and Wunsch algorithm (Needleman and Wunsch 1970). A computer-assisted sequence alignment can be conveniently performed using a standard software program such as GAP which is part of the Wisconsin Package Version 10.1 (Genetics Computer Group, Madison, Wis., USA) using the default scoring matrix with a gap creation penalty of 50 and a gap extension penalty of 3.

For the purpose of the invention, the "complement of a nucleotide sequence X" is the nucleotide sequence which would be capable of forming a double-stranded DNA molecule with the represented nucleotide sequence, and which can be derived from the represented nucleotide sequence by replacing the nucleotides by their complementary nucleotide according to Chargaff's rules (A< >T; G< >C) and reading in the 5' to 3' direction, i.e., in opposite direction of the represented nucleotide sequence.

C. Plants Tolerized to HPPD Inhibitors

HPPD inhibitor tolerance is enhanced in plants by generating transformants of the plant that express one or more polypeptide components of an exogenous PQ synthetic pathway in a plant. It is theorized that the components of the exogenous PQ synthetic pathway provide an alternate pathway for the generation of downstream catabolites produced by the endogenous pathway inhibited by the HPPD inhibitors, leading to increased tolerance to HPPD inhibitors herbicides.

HPPD inhibitor herbicides of the present disclosure like those of the class of N (1,2,5-oxadiazol-3-yl)benzamides, N-(tetrazol-4-yl)- or N-(triazol-3-yl)arylcarboxamides, such as 2-chloro-3-ethoxy-4-(methylsulfonyl)-N-(1-methyl-1H-tetrazol-5-yl)benzamide and 2-Chloro-3-(methoxymethyl)-4-(methylsulfonyl)-N-(1-methyl-1H-tetrazol-5-yl)benzamide, triketones, such as tembotrione, sulcotrione and mesotrione, the class of isoxazoles such as isoxaflutole, or of the class of pyrazolinates, such as pyrasulfotole and topramezone, particularly selected from tembotrione, sulcotrione, topramezone, bicyclopyrone, tefuryltrione, isoxaflutole, and mesotrione, have an outstanding herbicidal activity against a broad spectrum of economically important monocotyledonous and dicotyledonous annual harmful plants. The active substances also act efficiently on perennial harmful plants which produce shoots from rhizomes, wood stocks or other perennial organs and which are difficult to control. Within the meaning of the present disclosure, "herbicide" is understood as being a herbicidally active substance on its own or such a substance which is combined with an additive which alters its efficacy, such as, for example, an agent which increases its activity (a synergistic agent) or which limits its activity (a safener). The herbicide may further comprise solid or liquid adjuvants or carriers that are ordinarily employed in formulation technology (e.g. natural or regenerated mineral substances, solvents, dispersants, wetting agents, tackifiers, emulsifiers, growth promoting agents, and the like), as well as one or more additional herbicides and/or one or more pesticides (e.g., insecticides, virucides, microbicides, amoebicides, pesticides, fungicides, bacteriocides, nematocides, molluscicides, and the like).

It is contemplated that a complete exogenous PQ pathway may not be necessary to tolerize the plant to HPPD inhibitors, as endogenous enzymes may have the same or similar activities as one or more components of the exogenous PQ pathway. Transformants comprising different combinations of exogenous PQ components therefore may be tested to determine the ability of the combination to confer HPPD inhibitor tolerance on the plant. Any suitable method for measuring tolerance to HPPD inhibitor herbicides can be used to evaluate the transformants. Tolerance can be measured by monitoring the ability of a cell or organism to survive a particular HPPD inhibitor herbicide application, or the ability to carry out essential cellular functions such as photosynthesis, protein synthesis or respiration and reproduction in a manner that is not readily discernable from untreated cells or organisms, or the ability to have no significant difference in yield or even improved yield for plants treated with HPPD inhibitor herbicide compared to such plants not treated with such herbicide (but where weeds have been removed or prevented by a mechanism other than application of the HPPD inhibitor herbicide). In some embodiments, tolerance can be measured according to a visible indicator phenotype of the cell or organism transformed with the nucleic acid encoding the HPPD inhibitor herbicide tolerant polypeptide(s), or in an in vitro assay of the HPPD inhibitor herbicide tolerant polypeptide(s), in the presence of different concentrations of the various HPPD inhibitors. Dose responses and relative shifts in dose responses associated with these indicator phenotypes (formation of brown color, growth inhibition, bleaching, herbicidal effect etc.) are conveniently expressed in terms, for example, of GR50 (concentration for 50% reduction of growth) or MIC (minimum inhibitory concentration) values where increases in values correspond to increases in inherent tolerance to HPPD inhibitors, in the normal manner based upon plant damage, meristematic bleaching symptoms etc. at a range of different concentrations of herbicides. These data can be expressed in terms of, for example, GR50 values derived from dose/response curves having "dose" plotted on the x-axis and "percentage kill", "herbicidal effect", "numbers of emerging green plants" etc. plotted on the y-axis where increased GR50 values correspond to increased levels of inherent tolerance to HPPD inhibitors. Herbicides can suitably be applied pre-emergence or post emergence. In various embodiments, tolerance level of the transformants can be screened via transgenesis, regeneration, breeding and spray testing of a test plant such as tobacco, or a crop plant such as soybean, corn, or cotton. In line with the results obtained by such screening, such plants are more tolerant, desirably tolerant to at least 2 times the normal dose recommended for field applications, even more preferably tolerant up to 4 times the normal dose recommended for field applications, to HPPD inhibitor herbicides (e.g., HPPD inhibitor herbicides of the class of N (1,2,5-oxadiazol-3-yl) benzamides; N-(tetrazol-4-yl)- or N-(triazol-3-yl)arylcarboxamides, preferably such as 2-chloro-3-ethoxy-4-(methylsulfonyl)-N-(1-methyl-1H-tetrazol-5-yl)benzamide and 2-Chloro-3-(methoxymethyl)-4-(methylsulfonyl)-N-(1- methyl-1H-tetrazol-5-yl)benzamide; N-(1,3,4-oxadiazol-2-yl)benzamides, preferably such as 2-methyl-N-(5-methyl-1,3,4-oxadiazol-2-yl)-3-(methylsulfonyl)-4-(trifluoromethyl) benzamide (Cmpd. 1); N-(tetrazol-5-yl)- or N-(triazol-3-yl) arylcarboxamides, preferably such as 2-chloro-3-ethoxy-4-(methylsulfonyl)-N-(1-methyl-1H-tetrazol-5-yl)benzamide (Cmpd. 2), 4-(difluoromethyl)-2-methoxy-3-(methylsulfonyl)-N-(1-methyl-1H-tetrazol-5-yl)benzamide (Cmpd. 3), 2-chloro-3-(methylsulfanyl)-N-(1-methyl-1H-tetrazol-5-yl)-4-(trifluoromethyl)benzamide (Cmpd. 4), 2-(methoxymethyl)-3-(methylsulfinyl)-N-(1-methyl-1H-tetrazol-5-yl)-4-(trifluoromethyl)benzamide (Cmpd. 5); pyridazinone derivatives (WO2013/050421 and WO2013/083774); substituted 1,2,5-oxadiazoles (WO2013/072300 and WO2013/072402); and oxoprazin derivatives (WO2013/054495); triketones, preferably such as tembotrione, sulcotrione and mesotrione; the class of isoxazoles preferably such as isoxaflutole; or of the class of pyrazolinates, preferably such as pyrasulfotole and topramezone) than such plants that do not express any exogenous gene encoding HPPD inhibitor herbicide tolerant polypeptide(s). Accordingly, the term "capable of increasing the tolerance of a plant to at least one herbicide acting on HPPD" denotes a tolerance by the plant expressing the HPPD inhibitor herbicide tolerant polypeptide(s) to at least 1×, 2×, or 3×, or 4×, or greater, the normal field dose of the HPPD inhibitor herbicide as compared to a plant only expressing its endogenous PQ9 pathway polypeptides. In this regard, the term "herbicide acting on HPPD" is not limited to substances which are known and/or used as herbicides but to any substances which inhibit the catalytic activity of HPPD proteins. Alternatively, at the quantitative level, data like $pI_{50}$ ($pI_{50}$-value means the log value of the concentration of inhibitor necessary to inhibit 50% of the enzyme activity in molar concentration) can be obtained for the transformants of the invention and compared to a cell lacking the HPPD inhibitor herbicide tolerant polypeptide(s).

In one embodiment, the transformant comprises one or more components of an exogenous PQ pathway that catalyzes the conversion of chorismate to PQ9. An exemplary chorismate-to-PQ9 catalytic pathway of the cyanobacterium *Synechocystis* sp. (strain PCC6803) is illustrated at FIG. 1, and discussed by Pfaff et al., J. Biol. Chem., Vol. 289, No. 5, pp. 2675-2686 (2014), the content of which is incorporated herein by reference in its entirety. A chorismate lyase encoded by Sll1797 (herein referred to as UbiC) catalyzes the conversion of chorismate 101 to 4-hydroxybenzoate 102. An exemplary amino acid sequence of UbiC can be found at Uniprot Accession No. P73322 and is disclosed at SEQ ID NO: 1. 4-hydroxybenzoate 102 is prenylated by a 4-hydroxybenzoate solanesyltransferase encoded by Slr0926 (herein referred to as UbiA) to produce 4-hydroxy-3-solanesylbenzoate 103. An exemplary amino acid sequence of UbiA can be found at Uniprot Accession No. Q55500 and is disclosed herein at SEQ ID NO: 2. 4-hydroxy-3-solanesylbenzoate 103 is transformed to 2-solanesylphenol 104 by a mechanism comprising decarboxylation via a 4-hydroxy-3-prenylbenzoate decarboxylase complex comprising polypeptides encoded by Slr1099 (herein referred to as UbiX) and Sll0936 (herein referred to as UbiD). An exemplary amino acid sequence of UbiX can be found at Uniport Accession No. P72743 and is disclosed herein at SEQ ID NO: 3. An exemplary amino acid sequence of UbiD can be found at Uniprot Accession No. P72861 and is disclosed herein at SEQ ID NO: 4. 2-solanesylphenol 104 is transformed to 2-solanesyl-1,4-benzoquinol 105 (SBQ) via a solanesylphenol hydroxylase encoded by Slr1300 (referred to herein as UbiH). An exemplary amino acid sequence for UbiH can be found at Uniport Accession No. P72835 and is disclosed at SEQ ID NO: 5. In an embodiment, two methylation reactions give rise to plastoquinol-9 107 (PQH2) via a first step of methylation of SBQ to 2-methyl-6-solanesyl-1,4-benzoquinol 106 (MSBQ) followed by a second step of methylation of MSBQ to 2,3-dimethyl-6-solanesyl-1,4-benzoquinol 107 (DMSBQ), i.e. PQH2; in an alternative embodiment both methylations are performed concurrently in a single step. Exemplary cyanobacterial methyltransferases capable of catalyzing the methylation reaction(s) include uncharacterized methyltransferases encoded by Sll0418 (an exemplary amino acid sequence for which can be found at Uniprot Accession No. P74388 and is disclosed herein at SEQ ID NO: 6), Slr0089 (Uniprot Accession No. Q55809 and SEQ ID NO: 7), Sll1407 (Uniprot Accession No. P72601 and SEQ ID NO: 8), Slr0407 (Uniprot Accession No. P74439 and SEQ ID NO: 9), and Sll0829 (Uniprot Accession No. Q55423 and SEQ ID NO: 10) genes. The methyltransferase encoded by Sll0418 catalyzes the second methylation reaction. One or more of these methyltransferases catalyzes the first methylation in *Synechocystis*. In a plant cell, native plant MPBQ/MSBQ methyltransferase(s) (e.g., EC 2.1.1.295) can perform the methylation reaction(s). PQH2, which is the reduced form of plastoquinone-9 (PQ9), is oxidized by plastoquinol-plastocyanin reductase (e.g., EC 1.10.9.1) to form PQ9 108. A plastoquinol-plastocyanin reductase encoded by petC (an exemplary amino acid sequence for which can be found at GenBank CAA41421.1 and is disclosed herein at SEQ ID NO: 22) catalyzes the oxidation reaction in *Synechocystis*; in a plant cell, native plant plastoquinol-plastocyanin reductase can perform the oxidation.

It is contemplated that one or more of the components of the *Synechocystis* sp. PCC6803 PQ9 pathway may redundant of an activity of an endogenous enzyme of the plant. For example, soybeans express an enzyme having MPBQ/MSBQ methyltransferase activity, and thus may not need an exogenous polypeptide to supply this activity. Thus, various components of the PQ pathway may be tested for whether they are required in order for the transformant to be to tolerized to the HPPD inhibitor and, if the component's activity is redundant of an endogenous component, it may be deleted.

In an embodiment, a plant is engineered to express exogenous polypeptides sufficient to catalyze the conversion of chorismate to 2-solanesyl-1,4-benzoquinol in the plant cell, and endogenous plant components catalyze the conversion of 2-solanesyl-1,4-benzoquinol to PQ9. In an embodiment, the exogenous polypeptides that are sufficient to catalyze the conversion of chorismate to 2-solanesyl-1,4-benzoquinol in the plant cell comprise one or more of a chorismate lyase or a component thereof, a 4-hydroxybenzoate solanesyltransferase or a component thereof, a 4-hydroxy-3-prenylbenzoate decarboxylase or a component thereof, and a hydroxylase or a component thereof. In an embodiment, the exogenous polypeptides that are sufficient to catalyze the conversion of chorismate to 2-solanesyl-1,4-benzoquinol in the plant cell comprise each of a chorismate lyase or a component thereof, a 4-hydroxybenzoate solanesyltransferase or a component thereof, a 4-hydroxy-3-prenylbenzoate decarboxylase or a component thereof, and a solanesylphenol hydroxylase or a component thereof. In an embodiment, the one or more exogenous polypeptides comprise one or more polypeptide components of a cyanobacterial PQ9 pathway. In another embodiment, the *Synechocystis* sp. PCC6803 PQ9 pathway. In yet another embodiment, the exogenous polypeptides that are sufficient to catalyze the conversion of chorismate to 2-solanesyl-1,4-benzoquinol in the plant cell comprise one or more of UbiC, UbiA, UbiX, UbiD, and UbiH, each of which being derived from *Synechocystis* sp. PCC6803. In yet another embodiment, the exogenous polypeptides that are sufficient to catalyze the conversion of chorismate to 2-solanesyl-1,4-benzoquinol in the plant cell comprise each of UbiC, UbiA, UbiX, UbiD, and UbiH, each of which being derived from *Synechocystis* sp. PCC6803.

In another embodiment, the exogenous polypeptides are sufficient to catalyze the conversion of chorismate to PQ9 without needing the activity of an endogenous methyltransferase. In such an embodiment, the exogenous polypeptides may comprise each of a chorismate lyase or a component thereof, a 4-hydroxybenzoate solanesyltransferase or a component thereof, a 4-hydroxy-3-prenylbenzoate decarboxylase or a component thereof, a hydroxylase or a component thereof, and one or more methyltransferases. In yet another such embodiment, the exogenous polypeptides may comprise each of UbiC, UbiA, UbiX, UbiD, UbiH (or homologs thereof), and one or more polypeptides encoded by the Sll0418, Slr0089, Sll407, Slr0407, Sll0829, and/or petC genes (or homologs thereof), each of the foregoing polypeptides being derived from *Synechocystis* sp. PCC6803; exemplary coding sequences for each of these include, SEQ ID NOs: 11-15, 16-20, and 23, respectively.

As used herein, the phrase "an [enzyme] or a component thereof" shall mean that the polypeptide, which when expressed in a host cell, possesses the recited enzymatic activity either by itself or in cooperation with additional endogenous or exogenous components. As used herein, a "chorismate lyase" is an enzyme capable of catalyzing the conversion of chorismate to 4-hydroxybenzoate in a plant cell. As used herein, a "4-hydroxybenzoate solanesyltransferase" is an enzyme capable of catalyzing the conversion of 4-hydroxybenzoate to 4-hydroxy-3-solanesylbenzoate in a plant cell. As used herein, a "4-hydroxy-3-prenylbenzoate decarboxylase" is an enzyme capable of catalyzing the conversion of 4-hydroxy-3-solanesylbenzoate to 2-solanesylphenol in a plant cell. As used herein, a "hydroxylase" is an enzyme capable of catalyzing the conversion of 2-solanesylphenol to 2-solanesyl-1,4-benzoquinol in a plant cell. A "methyltransferase" as used herein is any individual enzyme or group of enzymes capable of participating in a methylation reaction or series of methylation reactions that result in conversion of 2-solanesyl-1,4-benzoquinol to PQ9.

As used herein, a "[polypeptide] derived from [organism]" shall refer to the full length recited polypeptide, as well as naturally occurring or synthetic variants or biologically active fragments thereof. "Fragments" or "biologically active portions" include polypeptide fragments comprising a portion of an amino acid sequence encoding the recited polypeptide and that retains the enzymatic activity of the full-length polypeptide. A biologically active portion of a recited polypeptide can be a polypeptide that is, for example, 10, 25, 50, 100 or more amino acids in length. Such biologically active portions can be prepared by recombinant techniques and evaluated for the relevant enzymatic activity. By "variants" is intended proteins or polypeptides having an amino acid sequence that is at least about 53%, 60%, 65%, about 70%, 75%, about 80%, 85%, 90%, 91%, 92%, 93%, 94%, 95%, 96%, 97%, 98% or 99% identical to any of SEQ ID NO: 1-10, wherein said variant has the enzyme activity of the full-length polypeptide. One of skill in the art will recognize that these values can be appropriately adjusted to determine corresponding identity of polypeptides encoded by two polynucleotides by taking into account codon degeneracy, amino acid similarity, reading frame positioning, and the like. For example, conservative amino acid substitutions may be made at one or more nonessential amino acid residues. A "nonessential" amino acid residue is a residue that can be altered from the reference sequence of a polypeptide without altering the biological activity, whereas an "essential" amino acid residue is required for biological activity. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Amino acid substitutions may be made in nonconserved regions that retain function. In general, such substitutions would not be made for conserved amino acid residues, or for amino acid residues residing within a conserved motif, where such residues are essential for polypeptide activity. However, one of skill in the art would understand that functional variants may have minor conserved or nonconserved alterations in the conserved residues. For example, the recited polypeptide may be modified to: contain one or more amino acid substitutions or deletions, for example by using mutagenesis techniques to obtain polypeptides having altered activity, stability, expression levels, etc., replace, add or delete some amino acids (e.g. 1-10) for cloning purposes, to make a transit peptide fusion, and the like, which retains the requisite enzyme activity or for cloning purposes. In an embodiment, the UbiC polypeptide derived from *Synechocystis* sp. PCC6803 is a polypeptide having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to SEQ ID NO: 1. In an embodiment, the UbiA polypeptide derived from *Synechocystis* sp. PCC6803 is a polypeptide having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to SEQ ID NO: 2. In an embodiment, the UbiX polypeptide derived from *Synechocystis* sp. PCC6803 is a polypeptide having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to SEQ ID NO: 3. In an embodiment, the UbiD polypeptide derived from *Synechocystis* sp. PCC6803 is a polypeptide having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to SEQ ID NO: 4. In an embodiment, the UbiH polypeptide derived from *Synechocystis* sp. PCC6803 is a polypeptide having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to SEQ ID NO: 5. In an embodiment, the Sll0418 polypeptide derived from *Synechocystis* sp. PCC6803 is a polypeptide having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to SEQ ID NO: 6. In an embodiment, the Slr0089 polypeptide derived from *Synechocystis* sp. PCC6803 is a polypeptide having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to SEQ ID NO: 7. In an embodiment, the Sll1407 polypeptide derived from *Synechocystis* sp. PCC6803 is a polypeptide having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to SEQ ID NO: 8. In an embodiment, the Slr0407 polypeptide derived from *Synechocystis* sp. PCC6803 is a polypeptide having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to SEQ ID NO: 9. In an embodiment, the Sll0829 polypeptide derived from *Synechocystis* sp. PCC6803 is a polypeptide having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to SEQ ID NO: 10. In an embodiment, the UbiC polypeptide derived from *Synechocystis* sp. PCC6803 is a polypeptide having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to a polypeptide encoded by SEQ ID NO: 11. In an embodiment, the UbiA polypeptide derived from *Synechocystis* sp. PCC6803 is a polypeptide having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to a polypeptide encoded by SEQ ID NO: 12. In an embodiment, the UbiX polypeptide derived from *Synechocystis* sp. PCC6803 is a polypeptide having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to a polypeptide encoded by SEQ ID NO: 13. In an embodiment, the UbiD polypeptide derived from *Synechocystis* sp. PCC6803 is a polypeptide having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to a polypeptide encoded by SEQ ID NO: 14. In an embodiment, the UbiH polypeptide derived from *Synechocystis* sp. PCC6803 is a polypeptide having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to a polypeptide encoded by SEQ ID NO: 15. In an embodiment, the Sll0418 polypeptide derived from *Synechocystis* sp. PCC6803 is a polypeptide having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to a polypeptide encoded by SEQ ID NO: 16. In an embodiment, the Slr0089 polypeptide derived from *Synechocystis* sp. PCC6803 is a polypeptide having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to a polypeptide encoded by SEQ ID NO: 17. In an embodiment, the Sll1407 polypeptide derived from *Synechocystis* sp. PCC6803 is a polypeptide having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to a polypeptide encoded by SEQ ID NO: 18. In an embodiment, the Slr0407 polypeptide derived from *Synechocystis* sp. PCC6803 is a polypeptide having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to a polypeptide encoded by SEQ ID NO: 19. In an embodiment, the Sll0829 polypeptide derived from *Synechocystis* sp. PCC6803 is a polypeptide having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to a polypeptide encoded by SEQ ID NO: 20. In an embodiment, the petC polypeptide derived from *Synechocystis* sp. PCC6803 is a polypeptide having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to SEQ ID NO: 22. In an embodiment, the petC polypeptide derived from *Synechocystis* sp. PCC6803 is a polypeptide having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to a polypeptide encoded by SEQ ID NO: 23.

In an embodiment, a transformed plant is provided, the transformed plant comprising:
  (a) chorismate lyase having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to, comprising, or consisting of SEQ ID NO: 1 or encoded by SEQ ID NO: 11;
  (b) a 4-hydroxybenzoate solanesyltransferase having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to, comprising, or consisting of SEQ ID NO: 2;
  (c) a 4-hydroxy-3-prenylbenzoate decarboxylase comprising a polypeptide having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to, comprising, or consisting of SEQ ID NO: 3, and/or a polypeptide having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to, comprising, or consisting of SEQ ID NO: 4;
  (d) a hydroxylase having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to, comprising, or consisting of SEQ ID NO: 5; and
  (e) optionally, one or more methyltransferases selected from the group consisting of:
    (e1) a methyltransferase having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to, comprising, or consisting of SEQ ID NO: 6;

(e2) a methyltransferase having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to, comprising, or consisting of SEQ ID NO: 7;

(e3) a methyltransferase having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to, comprising, or consisting of SEQ ID NO: 8;

(e4) a methyltransferase having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to, comprising, or consisting of SEQ ID NO: 9; and (e5) a methyltransferase having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to, comprising, or consisting of SEQ ID NO: 10.

In an embodiment, the transformed plant comprises each of (a), (b), (c), and (d). In an embodiment, the transformed plant comprises each of (a), (b), (c), (d), and one or more of (e). In an embodiment, the transformed plant comprises each of (a), (b), (c), (d), and (e1). In an embodiment, the transformed plant comprises each of (a), (b), (c), (d), and (e2). In an embodiment, the transformed plant comprises each of (a), (b), (c), (d), and (e3). In an embodiment, the transformed plant comprises each of (a), (b), (c), (d), and (e4). In an embodiment, the transformed plant comprises each of (a), (b), (c), (d), and (e5). In an embodiment, the transformed plant comprises each of (a), (b), (c), (d), (e1), and (e2). In an embodiment, the transformed plant comprises each of (a), (b), (c), (d), (e1), and (e3). In an embodiment, the transformed plant comprises each of (a), (b), (c), (d), (e1), and (e4). In an embodiment, the transformed plant comprises each of (a), (b), (c), (d), (e1), and (e5). In an embodiment, the transformed plant comprises each of (a), (b), (c), (d), (e2), and (e3). In an embodiment, the transformed plant comprises each of (a), (b), (c), (d), (e2), and (e4). In an embodiment, the transformed plant comprises each of (a), (b), (c), (d), (e2), and (e5). In an embodiment, the transformed plant comprises each of (a), (b), (c), (d), (e3), and (e4). In an embodiment, the transformed plant comprises each of (a), (b), (c), (d), (e3), and (e5). In an embodiment, the transformed plant comprises each of (a), (b), (c), (d), (e4), and (e5). In an embodiment, the transformed plant comprises each of (a), (b), (c), (d), (e1), (e2), and (e3). In an embodiment, the transformed plant comprises each of (a), (b), (c), (d), (e1), (e2), and (e4). In an embodiment, the transformed plant comprises each of (a), (b), (c), (d), (e1), (e2), and (e5). In an embodiment, the transformed plant comprises each of (a), (b), (c), (d), (e1), (e3), and (e4). In an embodiment, the transformed plant comprises each of (a), (b), (c), (d), (e1), (e3), and (e5). In an embodiment, the transformed plant comprises each of (a), (b), (c), (d), (e1), (e4), and (e5). In an embodiment, the transformed plant comprises each of (a), (b), (c), (d), (e2), (e3), and (e4). In an embodiment, the transformed plant comprises each of (a), (b), (c), (d), (e2), (e3), and (e5). In an embodiment, the transformed plant comprises each of (a), (b), (c), (d), (e3), (e4), and (e5). In an embodiment, the transformed plant comprises each of (a), (b), (c), (d), (e2), (e3), (e4), and (e5). In an embodiment, the transformed plant comprises each of (a), (b), (c), (d), (e1), (e2), (e3), and (e4). In an embodiment, the transformed plant comprises each of (a), (b), (c), (d), (e1), (e2), (e3), and (e5). In an embodiment, the transformed plant comprises each of (a), (b), (c), (d), (e1), (e2), (e4), and (e5). In an embodiment, the transformed plant comprises each of (a), (b), (c), (d), (e1), (e3), (e4), and (e5). In an embodiment, the transformed plant comprises each of (a), (b), (c), (d), (e2), (e3), (e4), and (e5). In an embodiment, the transformed plant comprises each of (a), (b), (c), (d), (e1), (e2), (e3), (e4), and (e5). In an embodiment, the transformed plant comprises a chorismate lyase comprising SEQ ID NO: 1, a 4-hydroxybenzoate solanesyltransferase comprising SEQ ID NO: 2, a 4-hydroxy-3-prenylbenzoate decarboxylase comprising a polypeptide comprising SEQ ID NO: 3 and a polypeptide comprising SEQ ID NO: 4, and a hydroxylase comprising SEQ ID NO: 5. In an embodiment, the transformed plant comprises a chorismate lyase comprising SEQ ID NO: 1 or encoded by SEQ ID NO: 11, a 4-hydroxybenzoate solanesyltransferase comprising SEQ ID NO: 2 or encoded by SEQ ID NO: 12, a 4-hydroxy-3-prenylbenzoate decarboxylase comprising a polypeptide comprising SEQ ID NO: 3 or encoded by SEQ ID NO: 13, and a polypeptide comprising SEQ ID NO: 4 or encoded by SEQ ID NO: 14, a hydroxylase comprising SEQ ID NO: 5 or encoded by SEQ ID NO: 15, and a methyltransferase comprising SEQ ID NO: 6 or encoded by SEQ ID NO: 16. In an embodiment, the transformed plant comprises a chorismate lyase comprising SEQ ID NO: 1 or encoded by SEQ ID NO: 11, a 4-hydroxybenzoate solanesyltransferase comprising SEQ ID NO: 2 or encoded by SEQ ID NO: 12, a 4-hydroxy-3-prenylbenzoate decarboxylase comprising a polypeptide comprising SEQ ID NO: 3 or encoded by SEQ ID NO: 13 and a polypeptide comprising SEQ ID NO: 4 or encoded by SEQ ID NO: 14, a hydroxylase comprising SEQ ID NO: 5 or encoded by SEQ ID NO: 15, a first methyltransferase comprising SEQ ID NO: 7 or encoded by SEQ ID NO: 17, a second methyltransferase comprising SEQ ID NO: 8 or encoded by SEQ ID NO: 18, a third methyltransferase comprising SEQ ID NO: 9 or encoded by SEQ ID NO: 19, and a fourth methyltransferase comprising SEQ ID NO: 10 or encoded by SEQ ID NO: 20.

In an embodiment, a transformed plant is provided, the transformed plant comprising:

(a) polypeptide having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to, comprising, or consisting of SEQ ID NO: 1 or a polypeptide encoded by SEQ ID NO: 11;

(b) a polypeptide having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to, comprising, or consisting of SEQ ID NO: 2 or a polypeptide encoded by SEQ ID NO: 12;

(c1) a polypeptide having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to, comprising, or consisting of SEQ ID NO: 3 or a polypeptide encoded by SEQ ID NO: 13;

(c2) a polypeptide having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to, comprising, or consisting of SEQ ID NO: 4 or a polypeptide encoded by SEQ ID NO: 14;

(d) a polypeptide having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to, comprising, or consisting of SEQ ID NO: 5 or a polypeptide encoded by SEQ ID NO: 15; and (e) optionally, one or more polypeptide selected from the group consisting of:

(e1) a polypeptide having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to, comprising, or consisting of SEQ ID NO: 6 or a polypeptide encoded by SEQ ID NO: 16;

(e2) a polypeptide having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to, comprising, or consisting of SEQ ID NO: 7 or a polypeptide encoded by SEQ ID NO: 17;

(e3) a polypeptide having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to, comprising, or consisting of SEQ ID NO: 8 or a polypeptide encoded by SEQ ID NO: 18;

(e4) a polypeptide having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to, comprising, or consisting of SEQ ID NO: 9 or a polypeptide encoded by SEQ ID NO: 19; and (e5) a polypeptide having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to, comprising, or consisting of SEQ ID NO: 10 or a polypeptide encoded by SEQ ID NO: 20.

In an embodiment, the transformed plant comprises each of (a), (b), (c1), (c2), and (d). In an embodiment, the transformed plant comprises each of (a), (b), (c1), (c2), (d), and one or more of (e). In an embodiment, the transformed plant comprises each of (a), (b), (c1), (c2), (d), and (e1). In an embodiment, the transformed plant comprises each of (a), (b), (c1), (c2), (d), and (e2). In an embodiment, the transformed plant comprises each of (a), (b), (c1), (c2), (d), and (e3). In an embodiment, the transformed plant comprises each of (a), (b), (c1), (c2), (d), and (e4). In an embodiment, the transformed plant comprises each of (a), (b), (c1), (c2), (d), and (e5). In an embodiment, the transformed plant comprises each of (a), (b), (c1), (c2), (d), (e1), and (e2). In an embodiment, the transformed plant comprises each of (a), (b), (c1), (c2), (d), (e1), and (e3). In an embodiment, the transformed plant comprises each of (a), (b), (c1), (c2), (d), (e1), and (e4). In an embodiment, the transformed plant comprises each of (a), (b), (c1), (c2), (d), (e1), and (e5). In an embodiment, the transformed plant comprises each of (a), (b), (c1), (c2), (d), (e2), and (e3). In an embodiment, the transformed plant comprises each of (a), (b), (c1), (c2), (d), (e2), and (e4). In an embodiment, the transformed plant comprises each of (a), (b), (c1), (c2), (d), (e2), and (e5). In an embodiment, the transformed plant comprises each of (a), (b), (c1), (c2), (d), (e3), and (e4). In an embodiment, the transformed plant comprises each of (a), (b), (c1), (c2), (d), (e3), and (e5). In an embodiment, the transformed plant comprises each of (a), (b), (c1), (c2), (d), (e4), and (e5). In an embodiment, the transformed plant comprises each of (a), (b), (c1), (c2), (d), (e1), (e2), and (e3). In an embodiment, the transformed plant comprises each of (a), (b), (c1), (c2), (d), (e1), (e2), and (e4). In an embodiment, the transformed plant comprises each of (a), (b), (c1), (c2), (d), (e1), (e2), and (e5). In an embodiment, the transformed plant comprises each of (a), (b), (c1), (c2), (d), (e1), (e3), and (e4). In an embodiment, the transformed plant comprises each of (a), (b), (c1), (c2), (d), (e1), (e3), and (e5). In an embodiment, the transformed plant comprises each of (a), (b), (c1), (c2), (d), (e1), (e4), and (e5). In an embodiment, the transformed plant comprises each of (a), (b), (c1), (c2), (d), (e2), (e3), and (e4). In an embodiment, the transformed plant comprises each of (a), (b), (c1), (c2), (d), (e2), (e3), and (e5). In an embodiment, the transformed plant comprises each of (a), (b), (c1), (c2), (d), (e3), (e4), and (e5). In an embodiment, the transformed plant comprises each of (a), (b), (c1), (c2), (d), (e1), (e2), (e3), and (e4). In an embodiment, the transformed plant comprises each of (a), (b), (c1), (c2), (d), (e1), (e2), (e3), and (e5). In an embodiment, the transformed plant comprises each of (a), (b), (c1), (c2), (d), (e1), (e2), (e4), and (e5). In an embodiment, the transformed plant comprises each of (a), (b), (c1), (c2), (d), (e1), (e3), (e4), and (e5). In an embodiment, the transformed plant comprises each of (a), (b), (c1), (c2), (d), (e2), (e3), (e4), and (e5). In an embodiment, the transformed plant comprises each of (a), (b), (c1), (c2), (d), (e1), (e2), (e3), (e4), and (e5). In an embodiment, the transformed plant comprises a polypeptide comprising SEQ ID NO: 1, a polypeptide comprising SEQ ID NO: 2, a polypeptide comprising SEQ ID NO: 3, a polypeptide comprising SEQ ID NO: 4, and a polypeptide comprising SEQ ID NO: 5. In an embodiment, the transformed plant comprises a polypeptide comprising SEQ ID NO: 1, a polypeptide comprising SEQ ID NO: 2, a polypeptide comprising SEQ ID NO: 3, a polypeptide comprising SEQ ID NO: 4, a polypeptide comprising SEQ ID NO: 5, and a polypeptide comprising SEQ ID NO: 6. In an embodiment, the transformed plant comprises a polypeptide comprising SEQ ID NO: 1, a polypeptide comprising SEQ ID NO: 2, a polypeptide comprising SEQ ID NO: 3, a polypeptide comprising SEQ ID NO: 4, a polypeptide comprising SEQ ID NO: 5, a polypeptide comprising SEQ ID NO: 7, a polypeptide comprising SEQ ID NO: 8, a polypeptide comprising SEQ ID NO: 9, and a polypeptide comprising SEQ ID NO: 10. In an embodiment, the transformed plant comprises a polypeptide encoded by SEQ ID NO: 11, a polypeptide encoded by SEQ ID NO: 12, a polypeptide encoded by SEQ ID NO: 13, a polypeptide encoded by SEQ ID NO: 14, a polypeptide encoded by SEQ ID NO: 15, and a polypeptide encoded by SEQ ID NO: 16. In an embodiment, the transformed plant comprises a polypeptide encoded by SEQ ID NO: 11, a polypeptide encoded by SEQ ID NO: 12, a polypeptide encoded by SEQ ID NO: 13, a polypeptide encoded by SEQ ID NO: 14, a polypeptide encoded by SEQ ID NO: 15, a polypeptide encoded by SEQ ID NO: 17, a polypeptide encoded by SEQ ID NO: 18, a polypeptide encoded by SEQ ID NO: 19, and a polypeptide encoded by SEQ ID NO: 20.

D. Nucleic Acids Useful in Generating Tolerized Plants

The transformants as disclosed herein are generally obtained by transforming a host plant with an HPPD inhibitor herbicide tolerance gene. By "HPPD inhibitor herbicide tolerance gene" is intended a gene encoding one or more HPPD inhibitor tolerance polypeptide(s). As used herein "HPPD inhibitor tolerance polypeptide(s)" is an exogenous polypeptide or group of polypeptides that confer(s) upon a plant cell or organism the ability to tolerate a higher concentration of HPPD inhibitor herbicide than such cell or organism that does not express the exogenous polypeptide or group of polypeptides, or to tolerate a certain concentration of HPPD inhibitor herbicide for a longer period of time than such cell or organism that does not express the exogenous polypeptide or group of polypeptides, or that confers upon a cell or organism the ability to perform photosynthesis, grow, and/or reproduce with less damage or growth inhibition observed than such cell or organism not expressing such exogenous polypeptide or group of polypeptides. By "tolerate" or "tolerance" is intended either to survive a particular HPPD inhibitor herbicide application, or the ability to carry out essential cellular functions such as photosynthesis, protein synthesis or respiration and reproduction in a manner that is not readily discernable from untreated cells or organisms, or the ability to have no significant difference in yield or even improved yield for plants treated with HPPD inhibitor herbicide compared to such plants not treated with such herbicide (but where weeds have been removed or prevented by a mechanism other than application of the HPPD inhibitor herbicide, such as the methods described in WO2011/100302, which is herein incorporated by reference in its entirety). As used herein, an "exogenous polypeptide" is any polypeptide that is not naturally encoded in the genome of and/or expressed by the host cell or organism. As used herein, an "endogenous [component]" is any molecule (including but not limited to polypeptides and enzymes) that is naturally encoded in the genome of and/or produced by the host cell or organism. In an embodiment, the HPPD inhibitor tolerance polypeptide(s) of the HPPD inhibitor tolerance gene comprise one or more polypeptide components of an exogenous PQ pathway, such as those described herein.

The HPPD inhibitor tolerance gene(s) disclosed herein may be used to transform plants to tolerize the organism to HPPD inhibitors (e.g., by mating, cell fusion, or by crossing organisms containing an introduced nucleic acid encoding the exogenous peptide(s) with organisms not containing it and obtaining progeny containing such nucleic acid). The HPPD inhibitor tolerance genes are useful for preparing plants that show increased tolerance to HPPD inhibitor herbicides, particularly increased tolerance to HPPD inhibitor herbicides of the class of N (1,2,5-oxadiazol-3-yl)benzamides; N-(tetrazol-4-yl)- or N-(triazol-3-yl)arylcarboxamides, preferably such as 2-chloro-3-ethoxy-4-(methylsulfonyl)-N-(1-methyl-1H-tetrazol-5-yl)benzamide and 2-Chloro-3-(methoxymethyl)-4-(methylsulfonyl)-N-(1-methyl-1H-tetrazol-5-yl)benzamide; N-(1,3,4-oxadiazol-2-yl)benzamides, preferably such as 2-methyl-N-(5-methyl-1,3,4-oxadiazol-2-yl)-3-(methylsulfonyl)-4-(trifluoromethyl) benzamide (Cmpd. 1); N-(tetrazol-5-yl)- or N-(triazol-3-yl) arylcarboxamides, preferably such as 2-chloro-3-ethoxy-4-(methylsulfonyl)-N-(1-methyl-1H-tetrazol-5-yl)benzamide (Cmpd.2), 4-(difluoromethyl)-2-methoxy-3-(methylsulfonyl)-N-(1-methyl-1H-tetrazol-5-yl)benzamide (Cmpd. 3), 2-chloro-3-(methylsulfanyl)-N-(1-methyl-1H-tetrazol-5-yl)-4-(trifluoromethyl)benzamide (Cmpd. 4), and 2-(methoxymethyl)-3-(methylsulfinyl)-N-(1-methyl-1H-tetrazol-5-yl)-4-(trifluoromethyl)benzamide (Cmpd. 5); pyridazinone derivatives (WO2013/050421 and WO2013/083774); substituted 1,2,5-oxadiazoles (WO2013/072300 and WO2013/072402); and oxoprazin derivatives (WO2013/054495); triketones, preferably such as tembotrione, sulcotrione and mesotrione; the class of isoxazoles preferably such as isoxaflutole; or of the class of pyrazolinates, preferably such as pyrasulfotole and topramezone. The HPPD inhibitor herbicide tolerance gene of the invention may also show tolerance towards the "coumarone-derivative herbicides" (described in WO2009/090401, WO2009/090402, WO2008/071918, WO2008/009908). In this regard, any one of the HPPD inhibitor herbicide tolerance genes of the invention can also be expressed in a plant also expressing a chimeric homogentisate solanesyltransferase (HST) gene or a mutated HST gene as described in WO2011/145015, WO2013/064987, WO2013/064964, or WO2010/029311, to obtain plants tolerant to HST inhibitor herbicides. As used herein, a "coumarone-derivative herbicide" or "HST inhibitor herbicide" encompasses compounds which fall under the IUPAC nomenclature of 5H-thiopyrano[4,3-b]pyridin-8-ol, 5H-thiopyrano[3,4-b]pyrazin-8-ol, oxathiino[5,6-b]pyridin-4-ol, and oxathiino[5, 6-b]pyrazin-4-ol.

The HPPD inhibitor tolerance gene may be provided in expression cassettes for expression in the plant of interest. A "plant expression cassette" includes a DNA construct, including a recombinant DNA construct, that is capable of resulting in the expression of a polynucleotide in a plant cell. The cassette can include in the 5'-3' direction of transcription, a transcriptional initiation region (i.e., promoter, particularly a heterologous promoter) operably-linked to one or more polynucleotides of interest, and/or a translation and transcriptional termination region (i.e., termination region) functional in plants. The cassette may additionally contain at least one additional polynucleotide to be introduced into the organism, such as a selectable marker gene. Alternatively, the additional polynucleotide(s) can be provided on multiple expression cassettes. Such an expression cassette is provided with a plurality of restriction sites for insertion of the polynucleotide(s) to be under the transcriptional regulation of the regulatory regions.

In a further embodiment, the HPPD inhibitor tolerance gene is a chimeric gene comprising a coding sequence comprising heterologous nucleic acids encoding the HPPD inhibitor tolerance polypeptide(s) operably linked to a plant-expressible promoter and optionally a transcription termination and polyadenylation region. "Heterologous" generally refers to the polynucleotide or polypeptide that is not endogenous to the cell or is not endogenous to the location in the native genome in which it is present, and has been added to the cell by infection, transfection, microinjection, electroporation, microprojection, or the like. By "operably linked" is intended a functional linkage between two polynucleotides. For example, when a promoter is operably linked to a DNA sequence, the promoter sequence initiates and mediates transcription of the DNA sequence. It is recognized that operably linked polynucleotides may or may not be contiguous and, where used to reference the joining of two polypeptide coding regions, the polypeptides are expressed in the same reading frame.

The promoter may be any polynucleotide sequence which shows transcriptional activity in the chosen plant cells, plant parts, or plants. The promoter may be native or analogous, or foreign or heterologous, to the plant host and/or to the nucleic acids encoding the HPPD inhibitor tolerance polypeptide(s). Where the promoter is "native" or "analogous" to the plant host, it is intended that the promoter is found in the native plant into which the promoter is introduced. Where the promoter is "foreign" or "heterologous" to the DNA sequence, it is intended that the promoter is not the native or naturally occurring promoter for the operably linked DNA sequence of the invention. The promoter may be inducible or constitutive. It may be naturally-occurring, may be composed of portions of various naturally-occurring promoters, or may be partially or totally synthetic. Guidance for the design of promoters is provided by studies of promoter structure, such as that of Harley and Reynolds (1987) *Nucleic Acids Res.* 15:2343-2361. Also, the location of the promoter relative to the transcription start may be optimized. See, e.g., Roberts et al. (1979) *Proc. Natl. Acad. Sci. USA*, 76:760-764. Many suitable promoters for use in plants are well known in the art.

For instance, suitable constitutive promoters for use in plants include: the promoters from plant viruses, such as the peanut chlorotic streak caulimovirus (PClSV) promoter (U.S. Pat. No. 5,850,019); the 35S promoter from cauliflower mosaic virus (CaMV) (Odell et al. (1985) *Nature* 313:810-812); promoters of *Chlorella* virus methyltransferase genes (U.S. Pat. No. 5,563,328) and the full-length transcript promoter from figwort mosaic virus (FMV) (U.S. Pat. No. 5,378,619); the promoters from such genes as rice actin (McElroy et al. (1990) *Plant Cell* 2:163-171 and U.S. Pat. No. 5,641,876); ubiquitin (Christensen et al. (1989) *Plant Mol. Biol.* 12:619-632 and Christensen et al. (1992) *Plant Mol. Biol.* 18:675-689); pEMU (Last et al. (1991) *Theor. Appl. Genet.* 81:581-588); MAS (Velten et al. (1984) *EMBO J.* 3:2723-2730 and U.S. Pat. No. 5,510,474); maize H3 histone (Lepetit et al. (1992)*Mol. Gen. Genet.* 231:276-285 and Atanassova et al. (1992) *Plant J.* 2(3):291-300); *Brassica napus* ALS3 (PCT application WO97/41228); a plant ribulose-biscarboxylase/oxygenase (RuBisCO) small subunit gene; the circovirus (AU 689 311) or the Cassava vein mosaic virus (CsVMV, U.S. Pat. No. 7,053,205); and promoters of various *Agrobacterium* genes (see U.S. Pat. Nos. 4,771,002; 5,102,796; 5,182,200; and 5,428,147).

Suitable inducible promoters for use in plants include: the promoter from the ACE1 system which responds to copper (Mett et al. (1993) *PNAS* 90:4567-4571); the promoter of the maize In2 gene which responds to benzenesulfonamide herbicide safeners (Hershey et al. (1991) *Mol. Gen. Genetics* 227:229-237 and Gatz et al. (1994) *Mol. Gen. Genetics* 243:32-38); and the promoter of the Tet repressor from Tn10 (Gatz et al. (1991) *Mol. Gen. Genet.* 227:229-237). Another inducible promoter for use in plants is one that responds to an inducing agent to which plants do not normally respond. An exemplary inducible promoter of this type is the inducible promoter from a steroid hormone gene, the transcriptional activity of which is induced by a glucocorticosteroid hormone (Schena et al. (1991) *Proc. Natl. Acad. Sci. USA* 88:10421) or the recent application of a chimeric transcription activator, XVE, for use in an estrogen receptor-based inducible plant expression system activated by estradiol (Zuo et al. (2000) *Plant J.,* 24:265-273). Other inducible promoters for use in plants are described in EP 332104, PCT WO 93/21334 and PCT WO 97/06269 which are herein incorporated by reference in their entirety. Promoters composed of portions of other promoters and partially or totally synthetic promoters can also be used. See, e.g., Ni et al. (1995) *Plant J.* 7:661-676 and PCT WO 95/14098 describing such promoters for use in plants.

In one embodiment of this invention, a promoter sequence specific for particular regions or tissues of plants can be used to express the HPPD inhibitor tolerance polypeptide(s), such as promoters specific for seeds (Datla, R. et al., 1997, Biotechnology Ann. Rev. 3, 269-296), especially the napin promoter (EP 255 378 A1), the phaseolin promoter, the glutenin promoter, the helianthinin promoter (WO92/17580), the albumin promoter (WO98/45460), the oleosin promoter (WO98/45461), the SAT1 promoter or the SAT3 promoter (PCT/US98/06978).

Use may also be made of an inducible promoter advantageously chosen from the phenylalanine ammonia lyase (PAL), HMG-CoA reductase (HMG), chitinase, glucanase, proteinase inhibitor (PI), PR1 family gene, nopaline synthase (nos) and vspB promoters (U.S. Pat. No. 5,670,349, Table 3), the HMG2 promoter (U.S. Pat. No. 5,670,349), the apple beta-galactosidase (ABG1) promoter and the apple aminocyclopropane carboxylate synthase (ACC synthase) promoter (WO98/45445). Multiple promoters can be used in the constructs of the invention, including in succession.

The promoter may include, or be modified to include, one or more enhancer elements. In some embodiments, the promoter may include a plurality of enhancer elements. Promoters containing enhancer elements provide for higher levels of transcription as compared to promoters that do not include them. Suitable enhancer elements for use in plants include the PClSV enhancer element (U.S. Pat. No. 5,850,019), the CaMV 35S enhancer element (U.S. Pat. Nos. 5,106,739 and 5,164,316) and the FMV enhancer element (Maiti et al. (1997) *Transgenic Res.* 6:143-156); the translation activator of the tobacco mosaic virus (TMV) described in Application WO87/07644, or of the tobacco etch virus (TEV) described by Carrington & Freed 1990, J. Virol. 64: 1590-1597, for example, or introns such as the adh1 intron of maize or intron 1 of rice actin. See also PCT WO96/23898, WO2012/021794, WO2012/021797, WO2011/084370, and WO2011/028914.

Often, such constructs can contain 5' and 3' untranslated regions. Such constructs may contain a "signal sequence" or "leader sequence" to facilitate co-translational or post-translational transport of the peptide of interest to certain intracellular structures such as the chloroplast (or other plastid), endoplasmic reticulum, or Golgi apparatus, or to be secreted. For example, the construct can be engineered to contain a signal peptide to facilitate transfer of the peptide to the endoplasmic reticulum. By "signal sequence" is intended a sequence that is known or suspected to result in co-translational or post-translational peptide transport across the cell membrane. In eukaryotes, this typically involves secretion into the Golgi apparatus, with some resulting glycosylation. By "leader sequence" is intended any sequence that, when translated, results in an amino acid sequence sufficient to trigger co-translational transport of the peptide chain to a sub-cellular organelle. Thus, this includes leader sequences targeting transport and/or glycosylation by passage into the endoplasmic reticulum, passage to vacuoles, plastids including chloroplasts, mitochondria, and the like. It may also be preferable to engineer the plant expression cassette to contain an intron, such that mRNA processing of the intron is required for expression.

By "3' untranslated region" is intended a polynucleotide located downstream of a coding sequence. Polyadenylation signal sequences and other sequences encoding regulatory signals capable of affecting the addition of polyadenylic acid tracts to the 3' end of the mRNA precursor are 3' untranslated regions. By "5' untranslated region" is intended a polynucleotide located upstream of a coding sequence.

Other upstream or downstream untranslated elements include enhancers. Enhancers are polynucleotides that act to increase the expression of a promoter region. Enhancers are well known in the art and include, but are not limited to, the SV40 enhancer region and the 35S enhancer element.

The termination region may be native with the transcriptional initiation region, may be native with the sequence of the present invention, or may be derived from another source. Convenient termination regions are available from the Ti-plasmid of *A. tumefaciens*, such as the octopine synthase and nopaline synthase termination regions. See also Guerineau et al. (1991)*Mol. Gen. Genet.* 262:141-144; Proudfoot (1991) *Cell* 64:671-674; Sanfacon et al. (1991) *Genes Dev.* 5:141-149; Mogen et al. (1990) *Plant Cell* 2:1261-1272; Munroe et al. (1990) *Gene* 91:151-158; Ballas et al. (1989) *Nucleic Acids Res.* 17:7891-7903; Joshi et al. (1987) *Nucleic Acid Res.* 15:9627-9639; and European Patent Application EP 0 633 317 A1.

In one aspect of the invention, synthetic DNA sequences are designed for a given polypeptide, such as the polypeptides of the invention. Expression of the open reading frame of the synthetic DNA sequence in a cell results in production of the HPPD inhibitor tolerance polypeptide(s). Synthetic DNA sequences can be useful to simply remove unwanted restriction endonuclease sites, to facilitate DNA cloning strategies, to alter or remove any potential codon bias, to alter or improve GC content, to remove or alter alternate reading frames, and/or to alter or remove intron/exon splice recognition sites, polyadenylation sites, Shine-Delgarno sequences, unwanted promoter elements and the like that may be present in a native DNA sequence. It is also possible that synthetic DNA sequences may be utilized to introduce other improvements to a DNA sequence, such as introduction of an intron sequence, creation of a DNA sequence that is expressed as a protein fusion to organelle targeting sequences, such as chloroplast transit peptides, apoplast/vacuolar targeting peptides, or peptide sequences that result in retention of the resulting peptide in the endoplasmic reticulum. Synthetic genes can also be synthesized using host cell-preferred codons for improved expression, or may be synthesized using codons at a host-preferred codon usage frequency. See, for example, Campbell and Gowri (1990) *Plant Physiol.* 92:1-11; U.S. Pat. Nos. 6,320,100; 6,075,185; 5,380,831; and 5,436,391, U.S. Published Application Nos. 20040005600 and 20010003849, and Murray et al. (1989) *Nucleic Acids Res.* 17:477-498, herein incorporated by reference.

In one embodiment, the polynucleotides of interest are targeted to the chloroplast for expression. In this manner, where the polynucleotide of interest is not directly inserted into the chloroplast, the expression cassette will additionally contain a polynucleotide encoding a transit peptide to direct the nucleotide of interest to the chloroplasts. Such transit peptides are known in the art. See, for example, Von Heijne et al. (1991) *Plant Mol. Biol. Rep.* 9:104-126; Clark et al. (1989) *J. Biol. Chem.* 264:17544-17550; Della-Cioppa et al. (1987) *Plant Physiol.* 84:965-968; Romer et al. (1993) *Biochem. Biophys. Res. Commun.* 196:1414-1421; and Shah et al. (1986) *Science* 233:478-481.

The polynucleotides of interest to be targeted to the chloroplast may be optimized for expression in the chloroplast to account for differences in codon usage between the plant nucleus and this organelle. In this manner, the polynucleotides of interest may be synthesized using chloroplast-preferred codons. See, for example, U.S. Pat. No. 5,380,831, herein incorporated by reference.

This plant expression cassette can be inserted into a plant transformation vector. By "transformation vector" is intended a DNA molecule that allows for the transformation of a cell. Such a molecule may consist of one or more expression cassettes, and may be organized into more than one vector DNA molecule. For example, binary vectors are plant transformation vectors that utilize two non-contiguous DNA vectors to encode all requisite cis- and trans-acting functions for transformation of plant cells (Hellens and Mullineaux (2000) *Trends in Plant Science* 5:446-451). "Vector" refers to a polynucleotide construct designed for transfer between different host cells. "Expression vector" refers to a vector that has the ability to incorporate, integrate and express heterologous DNA sequences or fragments in a foreign cell.

The plant transformation vector comprises one or more DNA vectors for achieving plant transformation. For example, it is a common practice in the art to utilize plant transformation vectors that comprise more than one contiguous DNA segment. These vectors are often referred to in the art as binary vectors. Binary vectors as well as vectors with helper plasmids are most often used for *Agrobacterium*-mediated transformation, where the size and complexity of DNA segments needed to achieve efficient transformation is quite large, and it is advantageous to separate functions onto separate DNA molecules. Binary vectors typically contain a plasmid vector that contains the cis-acting sequences required for T-DNA transfer (such as left border and right border), a selectable marker that is engineered to be capable of expression in a plant cell, and a "polynucleotide of interest" (a polynucleotide engineered to be capable of expression in a plant cell for which generation of transgenic plants is desired). Also present on this plasmid vector are sequences required for bacterial replication. The cis-acting sequences are arranged in a fashion to allow efficient transfer into plant cells and expression therein. For example, the selectable marker sequence and the sequence of interest are located between the left and right borders. Often a second plasmid vector contains the trans-acting factors that mediate T-DNA transfer from *Agrobacterium* to plant cells. This plasmid often contains the virulence functions (Vir genes) that allow infection of plant cells by *Agrobacterium*, and transfer of DNA by cleavage at border sequences and vir-mediated DNA transfer, as is understood in the art (Hellens and Mullineaux (2000) *Trends in Plant Science*, 5:446-451). Several types of *Agrobacterium* strains (e.g., LBA4404, GV3101, EHA101, EHA105, etc.) can be used for plant transformation. The second plasmid vector is not necessary for introduction of polynucleotides into plants by other methods such as microprojection, microinjection, electroporation, polyethylene glycol, etc.

E. Plant Transformation

Methods disclosed herein may involve introducing a nucleotide construct into a plant. By "introducing" is intended to present to the plant the nucleotide construct in such a manner that the construct gains access to the interior of a cell of the plant. The methods of the invention do not require that a particular method for introducing a nucleotide construct to a plant is used, only that the nucleotide construct gains access to the interior of at least one cell of the plant. Methods for introducing nucleotide constructs into plants are known in the art including, but not limited to, stable transformation methods, transient transformation methods, and virus-mediated methods. See, for example, the methods for transforming plant cells and regenerating plants described in: U.S. Pat. Nos. 4,459,355, 4,536,475, 5,464, 763, 5,177,010, 5,187,073, EP 267,159 A1, EP 604 662 A1, EP 672 752 A1, U.S. Pat. Nos. 4,945,050, 5,036,006, 5,100,792, 5,371,014, 5,478,744, 5,179,022, 5,565,346, 5,484,956, 5,508,468, 5,538,877, 5,554,798, 5,489,520, 5,510,318, 5,204,253, 5,405,765, EP 442 174 A1, EP 486 233 A1, EP 486 234 A1, EP 539 563 A1, EP 674 725 A1, WO91/02071, WO95/06128, and WO2011/095460, each of which is herein incorporated by reference, particularly with respect to the transformation methods described therein.

In general, plant transformation methods involve transferring heterologous DNA into target plant cells (e.g. immature or mature embryos, suspension cultures, undifferentiated callus, protoplasts, etc.), followed by applying a maximum threshold level of appropriate selection (depending on the selectable marker gene) to recover the transformed plant cells from a group of untransformed cell mass. Explants are typically transferred to a fresh supply of the same medium and cultured routinely. Subsequently, the transformed cells are differentiated into shoots after placing on regeneration medium supplemented with a maximum threshold level of selecting agent. The shoots are then transferred to a selective rooting medium for recovering rooted shoot or plantlet. The transgenic plantlet then grows into mature plants and produce fertile seeds (e.g. Hiei et al. (1994) *The Plant Journal* 6:271-282; Ishida et al. (1996) *Nature Biotechnology* 14:745-750). Explants are typically transferred to a fresh supply of the same medium and cultured routinely. A general description of the techniques and methods for generating transgenic plants are found in Ayres and Park (1994) *Critical Reviews in Plant Science* 13:219-239 and Bommineni and Jauhar (1997) *Maydica* 42:107-120. Since the transformed material contains many cells; both transformed and non-transformed cells are present in any piece of subjected target callus or tissue or group of cells. The ability to kill non-transformed cells and allow transformed cells to proliferate results in transformed plant cultures. Often, the ability to remove non-transformed cells is a limitation to rapid recovery of transformed plant cells and successful generation of transgenic plants. Molecular and biochemical methods can be used to confirm the presence of the integrated heterologous gene of interest in the genome of transgenic plant.

Generation of transgenic plants may be performed by one of several methods, including, but not limited to, introduction of heterologous DNA by *Agrobacterium* into plant cells (*Agrobacterium*-mediated transformation), bombardment of plant cells with heterologous foreign DNA adhered to particles, and various other non-particle direct-mediated methods (e.g. Hiei et al. (1994) *The Plant Journal* 6:271-282; Ishida et al. (1996) *Nature Biotechnology* 14:745-750; Ayres and Park (1994) *Critical Reviews in Plant Science* 13:219-239; Bommineni and Jauhar (1997) *Maydica* 42:107-120) to transfer DNA.

Methods for transformation of chloroplasts are known in the art. See, for example, Svab et al. (1990) *Proc. Natl. Acad. Sci. USA* 87:8526-8530; Svab and Maliga (1993) *Proc. Natl. Acad. Sci. USA* 90:913-917; Svab and Maliga (1993) *EMBO J.* 12:601-606. The method relies on particle gun delivery of DNA containing a selectable marker and targeting of the DNA to the plastid genome through homologous recombination. Additionally, plastid transformation can be accomplished by transactivation of a silent plastid-borne transgene by tissue-preferred expression of a nuclear-encoded and plastid-directed RNA polymerase. Such a system has been reported in McBride et al. (1994) *Proc. Natl. Acad. Sci. USA* 91:7301-7305.

The plant cells that have been transformed may be grown into plants in accordance with conventional ways. See, for example, McCormick et al. (1986) *Plant Cell Reports* 5:81-84. These plants may then be grown, and either pollinated with the same transformed strain or different strains, and the resulting hybrid having constitutive expression of the desired phenotypic characteristic identified. Two or more generations may be grown to ensure that expression of the desired phenotypic characteristic is stably maintained and inherited and then seeds harvested to ensure expression of the desired phenotypic characteristic has been achieved. In this manner, the present invention provides transformed seed (also referred to as "transgenic seed") having a nucleotide construct of the invention, for example, an expression cassette of the invention, stably incorporated into their genome. In various embodiments, the seed can be coated with at least one fungicide and/or at least one insecticide, at least one herbicide, and/or at least one safener, or any combination thereof.

F. Evaluation of Plant Transformation

Following introduction of heterologous foreign DNA into plant cells, the transformation or integration of the heterologous gene in the plant genome is confirmed by various methods such as analysis of nucleic acids, proteins and metabolites associated with the integrated gene.

PCR analysis is a rapid method to screen transformed cells, tissue or shoots for the presence of incorporated gene at the earlier stage before transplanting into the soil (Sambrook and Russell (2001) *Molecular Cloning: A Laboratory Manual* (Cold Spring Harbor Laboratory Press, Cold Spring Harbor, NY)). PCR is carried out using oligonucleotide primers specific to the gene of interest or *Agrobacterium* vector background, etc.

Plant transformation may be confirmed by Southern blot analysis of genomic DNA (Sambrook and Russell (2001) supra). In general, total DNA is extracted from the transformant, digested with appropriate restriction enzymes, fractionated in an agarose gel and transferred to a nitrocellulose or nylon membrane. The membrane or "blot" can then be probed with, for example, radiolabeled $^{32}$P target DNA fragment to confirm the integration of the introduced gene in the plant genome according to standard techniques (Sambrook and Russell, 2001, supra).

In Northern analysis, RNA is isolated from specific tissues of transformant, fractionated in a formaldehyde agarose gel, and blotted onto a nylon filter according to standard procedures that are routinely used in the art (Sambrook and Russell (2001) supra). Expression of RNA encoded by nucleotide sequences of the invention is then tested by hybridizing the filter to a radioactive probe derived from a GDC by methods known in the art (Sambrook and Russell (2001) supra). RNA can also be detected and/or quantified using reverse transcriptase PCR as known in the art (e.g., Green and Sambrook (2012) Molecular Cloning: A Laboratory Manual, $4^{th}$ Edition, Cold Spring Harbor Laboratory Press, Woodbury, NY).

Western blot, ELISA, lateral flow testing, and biochemical assays and the like may be carried out on the transgenic plants to determine the presence of polypeptide encoded by the HPPD herbicide tolerance gene by standard procedures (Sambrook and Russell (2001) supra) using antibodies that bind to one or more epitopes present on the herbicide tolerance protein.

G. Gene Stacking

In the commercial production of crops, it is desirable to eliminate under reliable pesticidal management unwanted plants (i.e., "weeds") from a field of crop plants. An ideal treatment would be one which could be applied to an entire field but which would eliminate only the unwanted plants while leaving the crop plants unaffected. One such treatment system would involve the use of crop plants which are tolerant to an herbicide so that when the herbicide is sprayed on a field of herbicide-tolerant crop plants, the crop plants would continue to thrive while non-herbicide-tolerant weeds are killed or severely damaged. Ideally, such treatment systems would take advantage of varying herbicide properties so that weed control could provide the best possible combination of flexibility and economy. For example, individual herbicides have different longevities in the field, and some herbicides persist and are effective for a relatively long time after they are applied to a field while other herbicides are quickly broken down into other and/or non-active compounds. An ideal treatment system would allow the use of different herbicides so that growers could tailor the choice of herbicides for a particular situation.

While a number of herbicide-tolerant crop plants are presently commercially available, an issue that has arisen for many commercial herbicides and herbicide/crop combinations is that individual herbicides typically have incomplete spectrum of activity against common weed species. For most individual herbicides which have been in use for some time, populations of herbicide resistant weed species and biotypes have become more prevalent (see, e.g., Tranel and Wright (2002) *Weed Science* 50: 700-712; Owen and Zelaya (2005) *Pest Manag. Sci.* 61: 301-311). Transgenic plants which are tolerant to more than one herbicide have been described (see, e.g., WO2005/012515). However, improvements in every aspect of crop production, weed control options, extension of residual weed control, and improvement in crop yield are continuously in demand.

Expression of exogenous PQ pathway components may advantageously be combined in plants with other genes which encode proteins or RNAs that confer useful agronomic properties to such plants. Among the genes which encode proteins or RNAs that confer useful agronomic properties on the transformed plants, mention can be made of the DNA sequences encoding proteins which confer tolerance to one or more herbicides that, according to their chemical structure, differ from HPPD inhibitor herbicides, and others which confer tolerance to certain insects, those which confer tolerance to certain diseases, DNAs that encodes RNAs that provide nematode or insect control, and the like. Such genes are in particular described in published PCT Patent Applications WO91/02071 and WO95/06128 and in U.S. Pat. No. 7,923,602 and US Patent Application Publication No. 20100166723, each of which is herein incorporated by reference in its entirety.

Among the DNA sequences encoding proteins which confer tolerance to certain herbicides on the transformed plant cells and plants, mention can be made of a bar or PAT gene or the *Streptomyces coelicolor* gene described in WO2009/152359 which confers tolerance to glufosinate herbicides, a gene encoding a suitable EPSPS which confers tolerance to herbicides having EPSPS as a target, such as glyphosate and its salts (U.S. Pat. Nos. 4,535,060, 4,769, 061, 5,094,945, 4,940,835, 5,188,642, 4,971,908, 5,145,783, 5,310,667, 5,312,910, 5,627,061, 5,633,435), a gene encoding glyphosate-n-acetyltransferase (for example, U.S. Pat. Nos. 8,222,489, 8,088,972, 8,044,261, 8,021,857, 8,008, 547, 7,999,152, 7,998,703, 7,863,503, 7,714,188, 7,709,702, 7,666,644, 7,666,643, 7,531,339, 7,527,955, and 7,405, 074), or a gene encoding glyphosate oxidoreductase (for example, U.S. Pat. No. 5,463,175).

Among the DNA sequences encoding a suitable EPSPS which confer tolerance to the herbicides which have EPSPS as a target, mention will more particularly be made of the gene which encodes a plant EPSPS, in particular maize EPSPS, particularly a maize EPSPS which comprises two mutations, particularly a mutation at amino acid position 102 and a mutation at amino acid position 106 (WO2004/074443), and which is described in U.S. Pat. No. 6,566,587, hereinafter named double mutant maize EPSPS or 2mEPSPS, or the gene which encodes an EPSPS isolated from *Agrobacterium* and which is described by sequence ID No. 2 and sequence ID No. 3 of U.S. Pat. No. 5,633,435, also named CP4.

Among the DNA sequences encoding a suitable EPSPS which confer tolerance to the herbicides which have EPSPS as a target, mention will more particularly be made of the gene which encodes an EPSPS GRG23 from *Arthrobacter globiformis*, but also the mutants GRG23 ACE1, GRG23 ACE2, or GRG23 ACE3, particularly the mutants or variants of GRG23 as described in WO2008/100353, such as GRG23 (ace3)R173K of SEQ ID No. 29 in WO2008/100353.

In the case of the DNA sequences encoding EPSPS, and more particularly encoding the above genes, the sequence encoding these enzymes is advantageously preceded by a sequence encoding a transit peptide, in particular the "optimized transit peptide" described in U.S. Pat. No. 5,510,471 or 5,633,448.

Exemplary herbicide tolerance traits that can be combined with the nucleic acid sequence of the invention further include at least one ALS (acetolactate synthase) inhibitor (WO2007/024782); a mutated *Arabidopsis* ALS/AHAS gene (U.S. Pat. No. 6,855,533); genes encoding 2,4-D-monooxygenases conferring tolerance to 2,4-D (2,4-dichlorophenoxyacetic acid) by metabolization (U.S. Pat. No. 6,153,401); and genes encoding Dicamba monooxygenases conferring tolerance to dicamba (3,6-dichloro-2-methoxybenzoic acid) by metabolization (US 2008/0119361 and US 2008/0120739).

In various embodiments, the HPPD inhibitor herbicide tolerance gene disclosed herein is stacked with one or more herbicide tolerant genes, including one or more additional HPPD inhibitor herbicide tolerant genes, and/or one or more genes tolerant to glyphosate and/or glufosinate. In one embodiment, an HPPD inhibitor herbicide tolerance gene disclosed herein is combined with 2mEPSPS and bar.

Among the DNA sequences encoding proteins concerning properties of tolerance to insects, mention will more particularly be made of the Bt proteins widely described in the literature and well known to those skilled in the art. Mention will also be made of proteins extracted from bacteria such as *Photorhabdus* (WO97/17432 & WO98/08932).

Among such DNA sequences encoding proteins of interest which confer novel properties of tolerance to insects, mention will more particularly be made of the Bt Cry or VIP proteins widely described in the literature and well known to those skilled in the art. These include the Cry1F protein or hybrids derived from a Cry1F protein (e.g., the hybrid Cry1A-Cry1F proteins described in U.S. Pat. Nos. 6,326, 169; 6,281,016; 6,218,188, or toxic fragments thereof), the Cry1A-type proteins or toxic fragments thereof, preferably the Cry1Ac protein or hybrids derived from the Cry1Ac protein (e.g., the hybrid Cry1Ab-Cry1Ac protein described in U.S. Pat. No. 5,880,275) or the Cry1Ab or Bt2 protein or insecticidal fragments thereof as described in EP451878, the Cry2Ae, Cry2Af or Cry2Ag proteins as described in WO2002/057664 or toxic fragments thereof, the Cry1A.105 protein described in WO 2007/140256 (SEQ ID No. 7) or a toxic fragment thereof, the VIP3Aa19 protein of NCBI accession ABG20428, the VIP3Aa20 protein of NCBI accession ABG20429 (SEQ ID No. 2 in WO 2007/142840), the VIP3A proteins produced in the COT202 or COT203 cotton events (WO2005/054479 and WO2005/054480, respectively), the Cry proteins as described in WO2001/47952, the VIP3Aa protein or a toxic fragment thereof as described in Estruch et al. (1996), Proc Natl Acad Sci USA. 28; 93(11):5389-94 and U.S. Pat. No. 6,291,156, the insecticidal proteins from Xenorhabdus (as described in WO98/50427), Serratia (particularly from S. entomophila) or Photorhabdus species strains, such as Tc-proteins from Photorhabdus as described in WO98/08932 (e.g., Waterfield et al., 2001, Appl Environ Microbiol. 67(11):5017-24; Ffrench-Constant and Bowen, 2000, Cell Mol Life Sci.; 57(5):828-33). Also any variants or mutants of any one of these proteins differing in some (1-10, preferably 1-5) amino acids from any of the above sequences, particularly the sequence of their toxic fragment, or which are fused to a transit peptide, such as a plastid transit peptide, or another protein or peptide, is included herein.

In various embodiments, an HPPD inhibitor herbicide tolerance gene disclosed herein can be combined in plants with one or more genes conferring a desirable trait, such as herbicide tolerance, insect tolerance, drought tolerance, nematode control, water use efficiency, nitrogen use efficiency, improved nutritional value, disease resistance, improved photosynthesis, improved fiber quality, stress tolerance, improved reproduction, and the like.

Particularly useful transgenic events which may be combined with the genes of the current invention in plants of the same species (e.g., by crossing or by re-transforming a plant containing another transgenic event with a chimeric gene of the invention), include Event 531/PV-GHBK04 (cotton, insect control, described in WO2002/040677), Event 1143-14A (cotton, insect control, not deposited, described in WO2006/128569); Event 1143-51B (cotton, insect control, not deposited, described in WO2006/128570); Event 1445 (cotton, herbicide tolerance, not deposited, described in US-A 2002-120964 or WO2002/034946); Event 17053 (rice, herbicide tolerance, deposited as PTA-9843, described in WO2010/117737); Event 17314 (rice, herbicide tolerance, deposited as PTA-9844, described in WO2010/117735); Event 281-24-236 (cotton, insect control-herbicide tolerance, deposited as PTA-6233, described in WO2005/103266 or US-A 2005-216969); Event 3006-210-23 (cotton, insect control-herbicide tolerance, deposited as PTA-6233, described in US-A 2007-143876 or WO2005/103266); Event 3272 (corn, quality trait, deposited as PTA-9972, described in WO2006/098952 or US-A 2006-230473); Event 33391 (wheat, herbicide tolerance, deposited as PTA-2347, described in WO2002/027004), Event 40416 (corn, insect control-herbicide tolerance, deposited as ATCC PTA-11508, described in WO 11/075593); Event 43A47 (corn, insect control-herbicide tolerance, deposited as ATCC PTA-11509, described in WO2011/075595); Event 5307 (corn, insect control, deposited as ATCC PTA-9561, described in WO2010/077816); Event ASR-368 (bent grass, herbicide tolerance, deposited as ATCC PTA-4816, described in US-A 2006-162007 or WO2004/053062); Event B16 (corn, herbicide tolerance, not deposited, described in US-A 2003-126634); Event BPS-CV127-9 (soybean, herbicide tolerance, deposited as NCIMB No. 41603, described in WO2010/080829); Event BLR1 (oilseed rape, restoration of male sterility, deposited as NCIB 41193, described in WO2005/074671), Event CE43-67B (cotton, insect control, deposited as DSM ACC2724, described in US-A 2009-217423 or WO2006/128573); Event CE44-69D (cotton, insect control, not deposited, described in US-A 2010-0024077); Event CE44-69D (cotton, insect control, not deposited, described in WO2006/128571); Event CE46-02A (cotton, insect control, not deposited, described in WO2006/128572); Event COT102 (cotton, insect control, not deposited, described in US-A 2006-130175 or WO2004/039986); Event COT202 (cotton, insect control, not deposited, described in US-A 2007-067868 or WO2005/054479); Event COT203 (cotton, insect control, not deposited, described in WO2005/054480); Event DAS21606-3/1606 (soybean, herbicide tolerance, deposited as PTA-11028, described in WO2012/033794), Event DAS40278 (corn, herbicide tolerance, deposited as ATCC PTA-10244, described in WO2011/022469); Event DAS-44406-6/pDAB8264.44.06.1 (soybean, herbicide tolerance, deposited as PTA-11336, described in WO2012/075426), Event DAS-14536-7/pDAB8291.45.36.2 (soybean, herbicide tolerance, deposited as PTA-11335, described in WO2012/075429), Event DAS-59122-7 (corn, insect control-herbicide tolerance, deposited as ATCC PTA 11384, described in US-A 2006-070139); Event DAS-59132 (corn, insect control-herbicide tolerance, not deposited, described in WO2009/100188); Event DAS68416 (soybean, herbicide tolerance, deposited as ATCC PTA-10442, described in WO2011/066384 or WO2011/066360); Event DP-098140-6 (corn, herbicide tolerance, deposited as ATCC PTA-8296, described in US-A 2009-137395 or WO 08/112019); Event DP-305423-1 (soybean, quality trait, not deposited, described in US-A 2008-312082 or WO2008/054747); Event DP-32138-1 (corn, hybridization system, deposited as ATCC PTA-9158, described in US-A 2009-0210970 or WO2009/103049); Event DP-356043-5 (soybean, herbicide tolerance, deposited as ATCC PTA-8287, described in US-A 2010-0184079 or WO2008/002872); Event EE-1 (brinjal, insect control, not deposited, described in WO 07/091277); Event FI117 (corn, herbicide tolerance, deposited as ATCC 209031, described in US-A 2006-059581 or WO 98/044140); Event FG72 (soybean, herbicide tolerance, deposited as PTA-11041, described in WO2011/063413), Event GA21 (corn, herbicide tolerance, deposited as ATCC 209033, described in US-A 2005-086719 or WO 98/044140); Event GG25 (corn, herbicide tolerance, deposited as ATCC 209032, described in US-A 2005-188434 or WO 98/044140); Event GHB119 (cotton, insect control-herbicide tolerance, deposited as ATCC PTA-8398, described in WO2008/151780); Event GHB614 (cotton, herbicide tolerance, deposited as ATCC PTA-6878, described in US-A 2010-050282 or WO2007/017186); Event GJ11 (corn, herbicide tolerance, deposited as ATCC 209030, described in US-A 2005-188434 or WO98/044140); Event GM RZ13 (sugar beet, virus resistance, deposited as NCIMB-41601, described in WO2010/076212); Event H7-1 (sugar beet, herbicide tolerance, deposited as NCIMB 41158 or NCIMB 41159, described in US-A 2004-172669 or WO 2004/074492); Event JOPLIN1 (wheat, disease tolerance, not deposited, described in US-A 2008-064032); Event LL27 (soybean, herbicide tolerance, deposited as NCIMB41658, described in WO2006/108674 or US-A 2008-320616); Event LL55 (soybean, herbicide tolerance, deposited as NCIMB 41660, described in WO 2006/108675 or US-A 2008-196127); Event LLcotton25 (cotton, herbicide tolerance, deposited as ATCC PTA-3343, described in WO2003/013224 or US-A 2003-097687); Event LLRICE06 (rice, herbicide tolerance, deposited as ATCC 203353, described in U.S. Pat. No. 6,468,747 or WO2000/026345); Event LLRice62 (rice, herbicide tolerance, deposited as ATCC 203352, described in WO2000/026345), Event LLRICE601 (rice, herbicide tolerance, deposited as ATCC PTA-2600, described in US-A 2008-2289060 or WO2000/026356); Event LY038 (corn, quality trait, deposited as ATCC PTA-5623, described in US-A 2007-028322 or WO2005/061720); Event MIR162 (corn, insect control, deposited as PTA-8166, described in US-A 2009-300784 or WO2007/142840); Event MIR604 (corn, insect control, not deposited, described in US-A 2008-167456 or WO2005/103301); Event MON15985 (cotton, insect control, deposited as ATCC PTA-2516, described in US-A 2004-250317 or WO2002/100163); Event MON810 (corn, insect control, not deposited, described in US-A 2002-102582); Event MON863 (corn, insect control, deposited as ATCC PTA-2605, described in WO2004/011601 or US-A 2006-095986); Event MON87427 (corn, pollination control, deposited as ATCC PTA-7899, described in WO2011/062904); Event MON87460 (corn, stress tolerance, deposited as ATCC PTA-8910, described in WO2009/111263 or US-A 2011-0138504); Event MON87701 (soybean, insect control, deposited as ATCC PTA-8194, described in US-A 2009-130071 or WO2009/064652); Event MON87705 (soybean, quality trait-herbicide tolerance, deposited as ATCC PTA-9241, described in US-A 2010-0080887 or WO2010/037016); Event MON87708 (soybean, herbicide tolerance, deposited as ATCC PTA-9670, described in WO2011/034704); Event MON87712 (soybean, yield, deposited as PTA-10296, described in WO2012/051199), Event MON87754 (soybean, quality trait, deposited as ATCC PTA-9385, described in WO2010/024976); Event MON87769 (soybean, quality trait, deposited as ATCC PTA-8911, described in US-A 2011-0067141 or WO2009/102873); Event MON88017 (corn, insect control-herbicide tolerance, deposited as ATCC PTA-5582, described in US-A 2008-028482 or WO2005/059103); Event MON88913 (cotton, herbicide tolerance, deposited as ATCC PTA-4854, described in WO2004/072235 or US-A 2006-059590); Event MON88302 (oilseed rape, herbicide tolerance, deposited as PTA-10955, described in WO2011/153186), Event MON88701 (cotton, herbicide tolerance, deposited as PTA-11754, described in WO2012/134808), Event MON89034 (corn, insect control, deposited as ATCC PTA-7455, described in WO 07/140256 or US-A 2008-260932); Event MON89788 (soybean, herbicide tolerance, deposited as ATCC PTA-6708, described in US-A 2006-282915 or WO2006/130436); Event MS11 (oilseed rape, pollination control-herbicide tolerance, deposited as ATCC PTA-850 or PTA-2485, described in WO2001/031042); Event MS8 (oilseed rape, pollination control-herbicide tolerance, deposited as ATCC PTA-730, described in WO2001/041558 or US-A 2003-188347); Event NK603 (corn, herbicide tolerance, deposited as ATCC PTA-2478, described in US-A 2007-292854); Event PE-7 (rice, insect control, not deposited, described in WO2008/114282); Event RF3 (oilseed rape, pollination control-herbicide tolerance, deposited as ATCC PTA-730, described in WO2001/041558 or US-A 2003-188347); Event RT73 (oilseed rape, herbicide tolerance, not deposited, described in WO2002/036831 or US-A 2008-070260); Event SYHT0H2/SYN-000H2-5 (soybean, herbicide tolerance, deposited as PTA-11226, described in WO2012/082548), Event T227-1 (sugar beet, herbicide tolerance, not deposited, described in WO2002/44407 or US-A 2009-265817); Event T25 (corn, herbicide tolerance, not deposited, described in US-A 2001-029014 or WO2001/051654); Event T304-40 (cotton, insect control-herbicide tolerance, deposited as ATCC PTA-8171, described in US-A 2010-077501 or WO2008/122406); Event T342-142 (cotton, insect control, not deposited, described in WO2006/128568); Event TC1507 (corn, insect control-herbicide tolerance, not deposited, described in US-A 2005-039226 or WO2004/099447); Event VIP1034 (corn, insect control-herbicide tolerance, deposited as ATCC PTA-3925., described in WO2003/052073), Event 32316 (corn, insect control-herbicide tolerance, deposited as PTA-11507, described in WO2011/084632), Event 4114 (corn, insect control-herbicide tolerance, deposited as PTA-11506, described in WO2011/084621), event EE-GM3/FG72 (soybean, herbicide tolerance, ATCC Accession No PTA-11041) optionally stacked with event EE-GM1/LL27 or event EE-GM2/LL55 (WO2011/063413A2), event DAS-68416-4 (soybean, herbicide tolerance, ATCC Accession No PTA-10442, WO2011/066360A1), event DAS-68416-4 (soybean, herbicide tolerance, ATCC Accession No PTA-10442, WO2011/066384A1), event DP-040416-8 (corn, insect control, ATCC Accession No PTA-11508, WO2011/075593A1), event DP-043A47-3 (corn, insect control, ATCC Accession No PTA-11509, WO2011/075595A1), event DP-004114-3 (corn, insect control, ATCC Accession No PTA-11506, WO2011/084621A1), event DP-032316-8 (corn, insect control, ATCC Accession No PTA-11507, WO2011/084632A1), event MON-88302-9 (oilseed rape, herbicide tolerance, ATCC Accession No PTA-10955, WO2011/153186A1), event DAS-21606-3 (soybean, herbicide tolerance, ATCC Accession No. PTA-11028, WO2012/033794A2), event MON-87712-4 (soybean, quality trait, ATCC Accession No. PTA-10296, WO2012/051199A2), event DAS-44406-6 (soybean, stacked herbicide tolerance, ATCC Accession No. PTA-11336, WO2012/075426A1), event DAS-14536-7 (soybean, stacked herbicide tolerance, ATCC Accession No. PTA-11335, WO2012/075429A1), event SYN-000H2-5 (soybean, herbicide tolerance, ATCC Accession No. PTA-11226, WO2012/082548A2), event DP-061061-7 (oilseed rape, herbicide tolerance, no deposit No available, WO2012071039A1), event DP-073496-4 (oilseed rape, herbicide tolerance, no deposit No available, US2012131692), event 8264.44.06.1 (soybean, stacked herbicide tolerance, Accession No PTA-11336, WO2012075426A2), event 8291.45.36.2 (soybean, stacked herbicide tolerance, Accession No. PTA-11335, WO2012075429A2), event SYHT0H2 (soybean, ATCC Accession No. PTA-11226, WO2012/082548A2), event MON88701 (cotton, ATCC Accession No PTA-11754, WO2012/134808A1), event KK179-2 (alfalfa, ATCC Accession No PTA-11833, WO2013/003558A1), event pDAB8264.42.32.1 (soybean, stacked herbicide tolerance, ATCC Accession No PTA-11993, WO2013/010094A1), event MZDT09Y (corn, ATCC Accession No PTA-13025, WO2013/012775A1).

H. Use as a Marker for Transformation

The invention also relates to the use, in a method for transforming plants, of a HPPD inhibitor herbicide tolerance gene as a marker gene or as a coding sequence which makes it possible to confer to the plant tolerance to herbicides which are HPPD inhibitors, and the use of one or more HPPD inhibitor(s) on plants comprising a HPPD inhibitor herbicide tolerance gene according to the invention. See, for example, U.S. Pat. No. 6,791,014, which is herein incorporated by reference in its entirety.

In this embodiment, an HPPD inhibitor can be introduced into the culture medium of the competent plant cells so as to bleach said cells before the transformation step. The bleached competent cells are then transformed with the HPPD inhibitor herbicide tolerance gene, as a selection marker, and the transformed cells which have integrated said selection marker into their genome become green, enabling them to be selected. Such a process makes it possible to decrease the time required for selecting the transformed cells.

Thus, one embodiment of the present invention consists of a method for transforming plant cells by introducing of a HPPD inhibitor herbicide tolerance gene as selection markers, wherein the method comprises preparing and culturing competent plant cells capable of receiving the heterologous gene in a suitable medium and introducing a suitable amount of HPPD inhibitor into the suitable culture medium of the competent plant cells. The competent cells are then transformed with the heterologous gene and the selection marker, and the transformed cells comprising the heterologous gene are grown in a suitable medium and transformants selected therefrom. The transformed cells can then be regenerated into a fertile transformed plant.

I. Plants and Plant Parts

By "plant" is intended whole plants, plant organs (e.g., leaves, stems, roots, etc.), seeds, plant cells, propagules, embryos and progeny of the same. Plant cells can be differentiated or undifferentiated (e.g., callus, suspension culture cells, protoplasts, leaf cells, root cells, phloem cells, pollen). The present invention may be used for introduction of polynucleotides into any plant species, including, but not limited to, monocots and dicots. Examples of plants of interest include, but are not limited to, corn (maize), sorghum, wheat, sunflower, tomato, crucifers, peppers, potato, cotton, rice, soybean, sugarbeet, sugarcane, tobacco, barley, and oilseed rape, *Brassica* sp., alfalfa, rye, millet, safflower, peanuts, sweet potato, cassava, coffee, coconut, pineapple, citrus trees, cocoa, tea, banana, avocado, fig, guava, mango, olive, *papaya*, cashew, macadamia, almond, oats, vegetables, ornamentals, and conifers.

Vegetables include, but are not limited to, tomatoes, lettuce, green beans, lima beans, peas, and members of the genus *Curcumis* such as cucumber, cantaloupe, and musk melon. Ornamentals include, but are not limited to, azalea, *hydrangea*, hibiscus, roses, tulips, daffodils, petunias, carnation, poinsettia, and *chrysanthemum*. Crop plants are also of interest, including, for example, maize, sorghum, wheat, sunflower, tomato, crucifers, peppers, potato, cotton, rice, soybean, sugarbeet, sugarcane, tobacco, barley, oilseed rape, etc.

This invention is suitable for any member of the monocot plant family including, but not limited to, maize, rice, barley, oats, wheat, sorghum, rye, sugarcane, pineapple, yams, onion, banana, coconut, and dates.

J. Methods for Increasing Plant Yield

Methods for increasing plant yield are provided. The methods comprise providing a plant comprising, or introducing into a plant or plant cell, a HPPD inhibitor herbicide tolerance gene as disclosed herein, growing the plant or a seed thereof in a field, and producing a harvest from said plants or seeds. As defined herein, the "yield" of the plant refers to the quality and/or quantity of biomass produced by the plant. By "biomass" is intended any measured plant product. An increase in biomass production is any improvement in the yield of the measured plant product. Increasing plant yield has several commercial applications. For example, increasing plant leaf biomass may increase the yield of leafy vegetables for human or animal consumption. Additionally, increasing leaf biomass can be used to increase production of plant-derived pharmaceutical or industrial products. An increase in yield can comprise any statistically significant increase including, but not limited to, at least a 1% increase, at least a 3% increase, at least a 5% increase, at least a 10% increase, at least a 20% increase, at least a 30%, at least a 50%, at least a 70%, at least a 100% or a greater increase.

In specific methods, the plant comprising a HPPD inhibitor herbicide tolerance gene as disclosed herein is treated with an effective concentration of an HPPD inhibitor herbicide, such as one or more HPPD inhibitor herbicide(s) selected from the group consisting of HPPD inhibitor herbicides of the class of N (1,2,5-oxadiazol-3-yl)benzamides; N-(tetrazol-4-yl)- or N-(triazol-3-yl)arylcarboxamides, preferably such as 2-chloro-3-ethoxy-4-(methylsulfonyl)-N-(1-methyl-1H-tetrazol-5-yl)benzamide and 2-Chloro-3-(methoxymethyl)-4-(methylsulfonyl)-N-(1-methyl-1H-tetrazol-5-yl)benzamide; N-(1,3,4-oxadiazol-2-yl) benzamides, preferably such as 2-methyl-N-(5-methyl-1,3,4-oxadiazol-2-yl)-3-(methylsulfonyl)-4-(trifluoromethyl) benzamide (Cmpd. 1); N-(tetrazol-5-yl)- or N-(triazol-3-yl) arylcarboxamides, preferably such as 2-chloro-3-ethoxy-4-(methylsulfonyl)-N-(1-methyl-1H-tetrazol-5-yl)benzamide (Cmpd. 2), 4-(difluoromethyl)-2-methoxy-3-(methylsulfonyl)-N-(1-methyl-1H-tetrazol-5-yl)benzamide (Cmpd. 3), 2-chloro-3-(methylsulfanyl)-N-(1-methyl-1H-tetrazol-5-yl)-4-(trifluoromethyl)benzamide (Cmpd. 4), and 2-(methoxymethyl)-3-(methylsulfinyl)-N-(1-methyl-1H-tetrazol-5-yl)-4-(trifluoromethyl)benzamide (Cmpd. 5); pyridazinone derivatives (WO2013/050421 and WO2013/083774); substituted 1,2,5-oxadiazoles (WO2013/072300 and WO2013/072402); and oxoprazin derivatives (WO2013/054495); triketones, preferably such as tembotrione, sulcotrione and mesotrione; the class of isoxazoles preferably such as isoxaflutole; or of the class of pyrazolinates, preferably such as pyrasulfotole and topramezone, where the herbicide application results in enhanced plant yield.

Methods for conferring herbicide tolerance in a plant or plant part are also provided. In such methods, a HPPD inhibitor herbicide tolerance gene as disclosed herein is introduced into the plant, wherein expression of the gene results in HPPD inhibitor herbicide tolerance. Plants produced via this method can be treated with an effective concentration of an herbicide (such as one or more HPPD inhibitor herbicide(s) selected from the group consisting of HPPD inhibitor herbicides of the class of N (1,2,5-oxadiazol-3-yl)benzamides; N-(tetrazol-4-yl)- or N-(triazol-3-yl) arylcarboxamides, preferably such as 2-chloro-3-ethoxy-4-(methylsulfonyl)-N-(1-methyl-1H-tetrazol-5-yl)benzamide and 2-Chloro-3-(methoxymethyl)-4-(methylsulfonyl)-N-(1-methyl-1H-tetrazol-5-yl)benzamide; N-(1,3,4-oxadiazol-2-yl)benzamides, preferably such as 2-methyl-N-(5-methyl-1,3,4-oxadiazol-2-yl)-3-(methylsulfonyl)-4-(trifluoromethyl) benzamide (Cmpd. 1); N-(tetrazol-5-yl)- or N-(triazol-3-yl) arylcarboxamides, preferably such as 2-chloro-3-ethoxy-4-(methylsulfonyl)-N-(1-methyl-1H-tetrazol-5-yl)benzamide (Cmpd. 2), 4-(difluoromethyl)-2-methoxy-3-(methylsulfonyl)-N-(1-methyl-1H-tetrazol-5-yl)benzamide (Cmpd. 3), 2-chloro-3-(methylsulfanyl)-N-(1-methyl-1H-tetrazol-5-yl)-4-(trifluoromethyl)benzamide (Cmpd. 4), 2-(methoxymethyl)-3-(methylsulfinyl)-N-(1-methyl-1H-tetrazol-5-yl)-4-(trifluoromethyl)benzamide (Cmpd. 5); pyridazinone derivatives (WO2013/050421 and WO2013/083774); substituted 1,2,5-oxadiazoles (WO2013/072300 and WO2013/072402); and oxoprazin derivatives (WO2013/054495);

triketones, preferably such as tembotrione, sulcotrione and mesotrione; the class of isoxazoles preferably such as isoxaflutole; or of the class of pyrazolinates, preferably such as pyrasulfotole and topramezone) and display an increased tolerance to the herbicide. An "effective concentration" of an herbicide in this application is an amount sufficient to slow or stop the growth of plants or plant parts that are not naturally tolerant or rendered tolerant to the herbicide.

K. Methods of Controlling Weeds in Afield

The present invention therefore also relates to a method of controlling undesired plants or for regulating the growth of plants in crops of plants comprising a HPPD inhibitor herbicide tolerance gene as disclosed herein, where one or more HPPD inhibitor herbicides, for example, one or more HPPD inhibitor herbicides selected from the class of N (1,2,5-oxadiazol-3-yl)benzamides; N-(tetrazol-4-yl)- or N-(triazol-3-yl)arylcarboxamides, preferably such as 2-chloro-3-ethoxy-4-(methylsulfonyl)-N-(1-methyl-1H-tetrazol-5-yl)benzamide and 2-Chloro-3-(methoxymethyl)-4-(methylsulfonyl)-N-(1-methyl-1H-tetrazol-5-yl)benzamide; N-(1,3,4-oxadiazol-2-yl)benzamides, preferably such as 2-methyl-N-(5-methyl-1,3,4-oxadiazol-2-yl)-3-(methylsulfonyl)-4-(trifluoromethyl)benzamide (Cmpd. 1); N-(tetrazol-5-yl)- or N-(triazol-3-yl)arylcarboxamides, preferably such as 2-chloro-3-ethoxy-4-(methylsulfonyl)-N-(1-methyl-1H-tetrazol-5-yl)benzamide (Cmpd. 2), 4-(difluoromethyl)-2-methoxy-3-(methylsulfonyl)-N-(1-methyl-1H-tetrazol-5-yl)benzamide (Cmpd. 3), 2-chloro-3-(methylsulfanyl)-N-(1-methyl-1H-tetrazol-5-yl)-4-(trifluoromethyl)benzamide (Cmpd. 4), and 2-(methoxymethyl)-3-(methylsulfinyl)-N-(1-methyl-1H-tetrazol-5-yl)-4-(trifluoromethyl)benzamide (Cmpd. 5); pyridazinone derivatives (WO2013/050421 and WO2013/083774); substituted 1,2,5-oxadiazoles (WO2013/072300 and WO2013/072402); and oxoprazin derivatives (WO2013/054495); triketones, preferably such as tembotrione, sulcotrione and mesotrione; the class of isoxazoles preferably such as isoxaflutole; or of the class of pyrazolinates, preferably such as pyrasulfotole and topramezone, are applied to the plants (for example harmful plants such as monocotyledonous or dicotyledonous weeds or undesired crop plants), to the seeds (for example grains, seeds or vegetative propagules such as tubers or shoot parts with buds) or to the area on which the plants grow (for example the area under cultivation). In this context, an effective concentration of one or more HPPD inhibitor herbicide(s), for example, one or more HPPD inhibitor herbicides selected from the group consisting of HPPD inhibitor herbicides of the class of N (1,2,5-oxadiazol-3-yl)benzamides; N-(tetrazol-4-yl)- or N-(triazol-3-yl)arylcarboxamides, preferably such as 2-chloro-3-ethoxy-4-(methylsulfonyl)-N-(1-methyl-1H-tetrazol-5-yl)benzamide and 2-Chloro-3-(methoxymethyl)-4-(methylsulfonyl)-N-(1-methyl-1H-tetrazol-5-yl)benzamide; N-(1,3,4-oxadiazol-2-yl) benzamides, preferably such as 2-methyl-N-(5-methyl-1,3,4-oxadiazol-2-yl)-3-(methylsulfonyl)-4-(trifluoromethyl) benzamide (Cmpd. 1); N-(tetrazol-5-yl)- or N-(triazol-3-yl) arylcarboxamides, preferably such as 2-chloro-3-ethoxy-4-(methylsulfonyl)-N-(1-methyl-1H-tetrazol-5-yl)benzamide (Cmpd. 2), 4-(difluoromethyl)-2-methoxy-3-(methylsulfonyl)-N-(1-methyl-1H-tetrazol-5-yl)benzamide (Cmpd. 3), 2-chloro-3-(methylsulfanyl)-N-(1-methyl-1H-tetrazol-5-yl)-4-(trifluoromethyl)benzamide (Cmpd. 4), and 2-(methoxymethyl)-3-(methylsulfinyl)-N-(1-methyl-1H-tetrazol-5-yl)-4-(trifluoromethyl)benzamide (Cmpd. 5); pyridazinone derivatives (WO2013/050421 and WO2013/083774); substituted 1,2,5-oxadiazoles (WO2013/072300 and WO2013/072402); and oxoprazin derivatives (WO2013/054495); triketones, preferably such as tembotrione, sulcotrione and mesotrione; the class of isoxazoles preferably such as isoxaflutole; or of the class of pyrazolinates, preferably such as pyrasulfotole and topramezone, the class of isoxazoles preferably such as isoxaflutole, or of the class of pyrazolinates, preferably such as pyrasulfotole and topramezone, particularly selected from tembotrione, sulcotrione, topramezone, bicyclopyrone, tefuryltrione, isoxaflutole, and mesotrione, can be applied for example pre-planting (if appropriate also by incorporation into the soil), pre-emergence or post-emergence, and may be combined with the application of other herbicides to which the crop is naturally tolerant, or to which it is resistant via expression of one or more other herbicide resistance transgenes. See, e.g., U.S. App. Pub. No. 2004/0058427 and PCT App. Pub. No. WO98/20144. By "effective concentration" is intended the concentration which controls the growth or spread of weeds or other untransformed plants without significantly affecting the HPPD inhibitor-tolerant plant or plant seed. Those of skill in the art understand that application of herbicides can take many different forms and can take place at many different times prior to and/or throughout the seed planting and growth process. "Pre-emergent" application refers to an herbicide which is applied to an area of interest (e.g., a field or area of cultivation) before a plant emerges visibly from the soil. "Post-emergent" application refers to an herbicide which is applied to an area after a plant emerges visibly from the soil. In some instances, the terms "pre-emergent" and "post-emergent" are used with reference to a weed in an area of interest, and in some instances these terms are used with reference to a crop plant in an area of interest. When used with reference to a weed, these terms may apply to a particular type of weed or species of weed that is present or believed to be present in the area of interest. "Pre-plant incorporation" of an herbicide involves the incorporation of compounds into the soil prior to planting.

Thus, the present disclosure comprises a method of controlling weeds in a field comprising planting in a field a plant or a seed thereof expressing one or more polypeptide members of an exogenous PQ pathway sufficient to catalyze the synthesis of PQ in the absence of a functional dioxygenase, and applying to said plant or area surrounding said plant an effective concentration of one or more HPPD inhibitor herbicides.

In one embodiment of this invention, a field to be planted with transformants (such as soybean, cotton, corn, or wheat plants, e.g.) as disclosed herein, can be treated with an HPPD inhibitor herbicide, such as isoxaflutole (IFT), before the plants are planted or the seeds are sown, which cleans the field of weeds that are killed by the HPPD inhibitor, allowing for no-till practices, followed by planting or sowing of the plants in that same pre-treated field later on (burndown application using an HPPD inhibitor herbicide). The residual activity of IFT will also protect the emerging and growing plants from competition by weeds in the early growth stages. Once the plants have a certain size, and weeds tend to re-appear, glufosinate or glyphosate, or an HPPD inhibitor or a mixture of an HPPD inhibitor with another herbicide such as glyphosate, can be applied as post-emergent herbicide over the top of the plants, when such plants are tolerant to said herbicides.

In another embodiment of this invention, a field in which seeds containing a HPPD inhibitor herbicide tolerance gene as disclosed herein were sown, can be treated with an HPPD inhibitor herbicide, such as IFT, before the plants emerge but after the seeds are sown (the field can be made weed-free before sowing using other means, typically conventional tillage practices such as ploughing, chisel ploughing, or seed bed preparation), where residual activity will keep the field free of weeds killed by the herbicide so that the emerging and growing plants have no competition by weeds (pre-emergence application of an HPPD inhibitor herbicide). Once the plants have a certain size, and weeds tend to re-appear, glufosinate or glyphosate, or an HPPD inhibitor or a mixture of an HPPD inhibitor with another herbicide such as glyphosate, can be applied as post-emergent herbicide over the top of the plants, when such plants are tolerant to said herbicides.

In another embodiment of this invention, plants containing a HPPD inhibitor herbicide tolerance gene as disclosed herein can be treated with an HPPD inhibitor herbicide, over the top of the plants that have emerged from the seeds that were sown, which cleans the field of weeds killed by the HPPD inhibitor, which application can be together with (e.g., in a spray tank mix), followed by or preceded by a treatment with glyphosate or glufosinate as post-emergent herbicide over the top of the plants (post-emergence application of an HPPD inhibitor herbicide (with or without glyphosate)), when such plants are tolerant to such herbicides.

Examples of individual representatives of the monocotyledonous and dicotyledonous weeds which can be controlled with an HPPD inhibitor herbicide include:

Monocotyledonous harmful plants of the genera: *Aegilops, Agropyron, Agrostis, Alopecurus, Apera, Avena, Brachiaria, Bromus, Cenchrus, Commelina, Cynodon, Cyperus, Dactyloctenium, Digitaria, Echinochloa, Eleocharis, Eleusine, Eragrostis, Eriochloa, Festuca, Fimbristylis, Heteranthera, Imperata, Ischaemum, Leptochloa, Lolium, Monochoria, Panicum, Paspalum, Phalaris, Phleum, Poa, Rottboellia, Sagittaria, Scirpus, Setaria, Sorghum.*

Dicotyledonous weeds of the genera: *Abutilon, Amaranthus, Ambrosia, Anoda, Anthemis, Aphanes, Artemisia, Atriplex, Bellis, Bidens, Capsella, Carduus, Cassia, Centaurea, Chenopodium, Cirsium, Convolvulus, Datura, Desmodium, Emex, Erysimum, Euphorbia, Galeopsis, Galinsoga, Galium, Hibiscus, Ipomoea, Kochia, Lamium, Lepidium, Lindernia, Matricaria, Mentha, Mercurialis, Mullugo, Myosotis, Papaver, Pharbitis, Plantago, Polygonum, Portulaca, Ranunculus, Raphanus, Rorippa, Rotala, Rumex, Salsola, Senecio, Sesbania, Sida, Sinapis, Solanum, Sonchus, Sphenoclea, Stellaria, Taraxacum, Thlaspi, Trifolium, Urtica, Veronica, Viola, Xanthium.*

HPPD inhibitor herbicides useful in the present invention, including but not limited to HPPD inhibitor herbicides of the class of N (1,2,5-oxadiazol-3-yl)benzamides; N-(tetrazol-4-yl)- or N-(triazol-3-yl)arylcarboxamides, such as 2-chloro-3-ethoxy-4-(methylsulfonyl)-N-(1-methyl-1H-tetrazol-5-yl)benzamide and 2-Chloro-3-(methoxymethyl)-4-(methylsulfonyl)-N-(1-methyl-1H-tetrazol-5-yl)benzamide; N-(1,3,4-oxadiazol-2-yl)benzamides, preferably such as 2-methyl-N-(5-methyl-1,3,4-oxadiazol-2-yl)-3-(methylsulfonyl)-4-(trifluoromethyl)benzamide (Cmpd. 1); N-(tetrazol-5-yl)- or N-(triazol-3-yl)arylcarboxamides, preferably such as 2-chloro-3-ethoxy-4-(methylsulfonyl)-N-(1-methyl-1H-tetrazol-5-yl)benzamide (Cmpd. 2), 4-(difluoromethyl)-2-methoxy-3-(methylsulfonyl)-N-(1-methyl-1H-tetrazol-5-yl)benzamide (Cmpd. 3), 2-chloro-3-(methylsulfanyl)-N-(1-methyl-1H-tetrazol-5-yl)-4-(trifluoromethyl)benzamide (Cmpd. 4), 2-(methoxymethyl)-3-(methylsulfinyl)-N-(1-methyl-1H-tetrazol-5-yl)-4-(trifluoromethyl)benzamide (Cmpd. 5); pyridazinone derivatives (WO2013/050421 and WO2013/083774); substituted 1,2,5-oxadiazoles (WO2013/072300 and WO2013/072402); and oxoprazin derivatives (WO2013/054495); triketones, preferably such as tembotrione, sulcotrione and mesotrione; the class of isoxazoles preferably such as isoxaflutole; or of the class of pyrazolinates, preferably such as pyrasulfotole and topramezone, can be formulated in various ways, depending on the prevailing biological and/or physico-chemical parameters. Examples of possible formulations are: wettable powders (WP), water-soluble powders (SP), water-soluble concentrates, emulsifiable concentrates (EC), emulsions (EW), such as oil-in-water and water-in-oil emulsions, sprayable solutions, suspension concentrates (SC), oil- or water-based dispersions, oil-miscible solutions, capsule suspensions (CS), dusts (DP), seed-dressing products, granules for application by broadcasting and on the soil, granules (GR) in the form of microgranules, spray granules, coated granules and adsorption granules, water-dispersible granules (WG), water-soluble granules (SG), ULV formulations, microcapsules and waxes.

These individual types of formulation are known in principle and are described, for example, in: Winnacker-Küchler, "Chemische Technologie" [Chemical technology], volume 7, C. Hanser Verlag Munich, 4th Ed. 1986; Wade van Valkenburg, "Pesticide Formulations", Marcel Dekker, N.Y., 1973; K. Martens, "Spray Drying" Handbook, 3rd Ed. 1979, G. Goodwin Ltd. London.

The formulation auxiliaries required, such as inert materials, surfactants, solvents and further additives, are also known and are described, for example, in: Watkins, "Handbook of Insecticide Dust Diluents and Carriers", 2nd Ed., Darland Books, Caldwell N.J., H.v. Olphen, "Introduction to Clay Colloid Chemistry"; 2nd Ed., J. Wiley & Sons, N.Y.; C. Marsden, "Solvents Guide"; 2nd Ed., Interscience, N.Y. 1963; McCutcheon's "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schönfeldt, "Grenzflächenaktive Äthylenoxidaddukte" [Interface-active ethylene oxide adducts], Wiss. Verlagsgesell., Stuttgart 1976; Winnacker-Küchler, "Chemische Technologie" [Chemical technology], volume 7, C. Hanser Verlag Munich, 4th Ed. 1986.

Based on these formulations, it is also possible to prepare combinations with other pesticidally active substances such as, for example, insecticides, acaricides, herbicides, fungicides, and with safeners, fertilizers and/or growth regulators, for example in the form of a ready mix or a tank mix.

L. Methods of Introducing Gene of the Invention into Another Plant

Also provided herein are methods of introducing the HPPD inhibitor herbicide tolerance gene as disclosed herein into another plant. The HPPD inhibitor herbicide tolerance gene as disclosed herein, or a fragment thereof, can be introduced into second plant by recurrent selection, backcrossing, pedigree breeding, line selection, mass selection, mutation breeding and/or genetic marker enhanced selection.

Thus, in one embodiment, the methods of the invention comprise crossing a first plant comprising a HPPD inhibitor herbicide tolerance gene as disclosed herein with a second plant to produce F1 progeny plants and selecting F1 progeny plants that are tolerant to a HPPD inhibitor herbicide tolerance gene as disclosed herein. The methods may further comprise crossing the selected progeny plants with the first plant comprising a HPPD inhibitor herbicide tolerance gene as disclosed herein to produce backcross progeny plants and selecting backcross progeny plants that are tolerant to an HPPD inhibitor herbicide or that comprise a HPPD inhibitor herbicide tolerance gene as disclosed herein. Methods for evaluating HPPD inhibitor herbicide tolerance are provided elsewhere herein. The methods may further comprise repeating these steps one or more times in succession to produce selected second or higher backcross progeny plants that are tolerant to an HPPD inhibitor herbicide or that comprise a HPPD inhibitor herbicide tolerance gene as disclosed herein.

Any breeding method involving selection of plants for the desired phenotype can be used in the method of the present invention. In some embodiments, The F1 plants may be self-pollinated to produce a segregating F2 generation. Individual plants may then be selected which represent the desired phenotype (e.g., HPPD inhibitor herbicide tolerance) in each generation (F3, F4, F5, etc.) until the traits are homozygous or fixed within a breeding population.

The second plant can be a plant having a desired trait, such as herbicide tolerance, insect tolerance, drought tolerance, nematode control, water use efficiency, nitrogen use efficiency, improved nutritional value, disease resistance, improved photosynthesis, improved fiber quality, stress tolerance, improved reproduction, and the like. The second plant may be an elite event as described elsewhere herein In various embodiments, plant parts (whole plants, plant organs (e.g., leaves, stems, roots, etc.), seeds, plant cells, propagules, embryos, and the like) can be harvested from the resulting cross and either propagated or collected for downstream use (such as food, feed, biofuel, oil, flour, meal, etc.).

M Methods of Obtaining a Plant Product

The present invention also relates to a process for obtaining a commodity product, comprising harvesting and/or milling the grains from a crop comprising a HPPD inhibitor herbicide tolerance gene as disclosed herein to obtain the commodity product. Agronomically and commercially important products and/or compositions of matter including but not limited to animal feed, commodities, and plant products and by-products that are intended for use as food for human consumption or for use in compositions and commodities that are intended for human consumption, particularly devitalized seed/grain products, including a (semi-)processed products produced from such grain/seeds, wherein said product is or comprises whole or processed seeds or grain, animal feed, corn or soy meal, corn or soy flour, corn, corn starch, soybean meal, soy flour, flakes, soy protein concentrate, soy protein isolates, texturized soy protein concentrate, cosmetics, hair care products, soy nut butter, natto, tempeh, hydrolyzed soy protein, whipped topping, shortening, lecithin, edible whole soybeans (raw, roasted, or as edamame), soy yogurt, soy cheese, tofu, yuba, as well as cooked, polished, steamed, baked or parboiled grain, and the like are intended to be within the scope of the present invention if these products and compositions of matter contain detectable amounts of the nucleotide and/or amino acid sequences set forth herein as being diagnostic for any plant containing such nucleotide sequences.

The following examples are offered by way of illustration and not by way of limitation.

EXAMPLES

Example 1: Transformation Vectors

Figure 2:
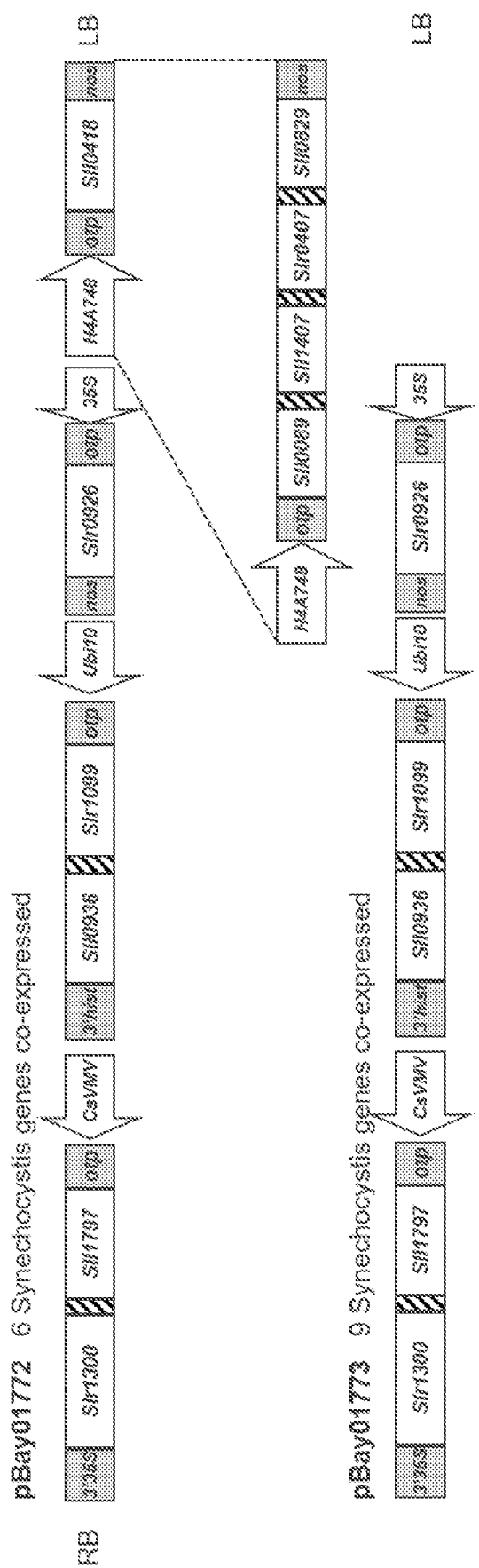
FIG. 2. illustrates two plant transformation vectors. Arrows illustrate promotor elements. Boxes with diagonal hatching indicate linker regions between two coding regions driven by the same promotor. Unfilled rectangular elements indicate coding regions. Shaded rectangles are other regions, including 3' untranslated regions (3'35S, 3' hist, and nos) and optimized transit peptides (OTP).
Figure 3:
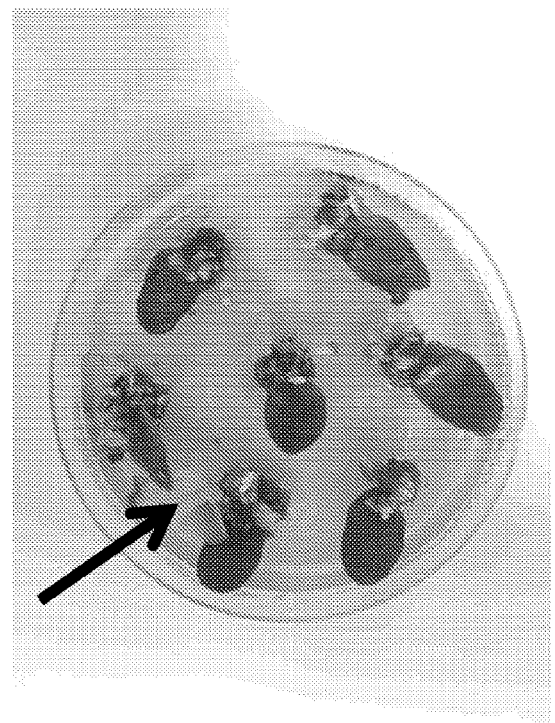
Figure 3:
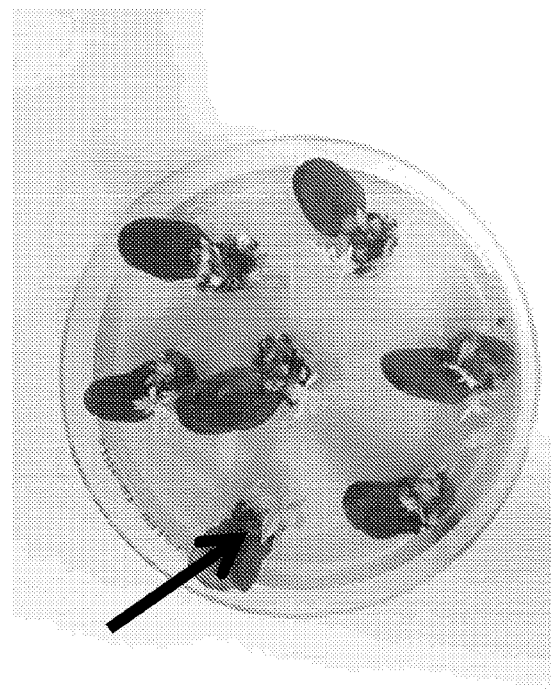
Figure 3:
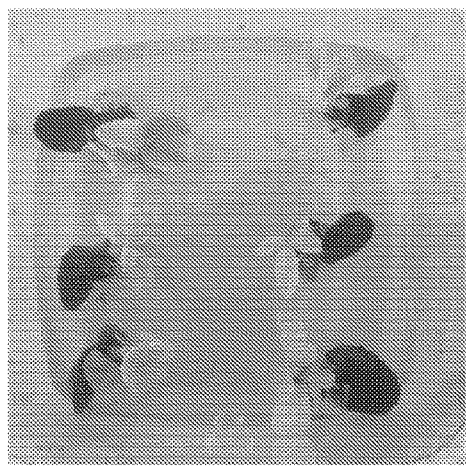
Figure 4:
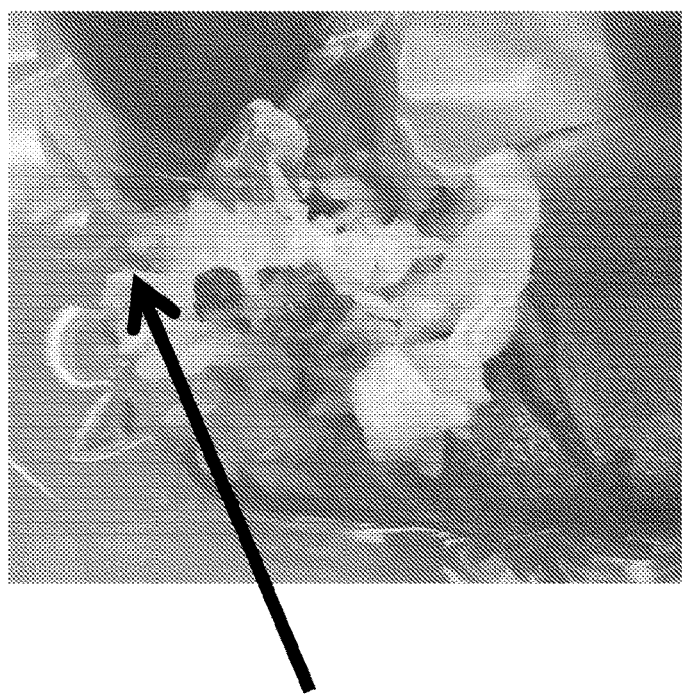
Figure 4:
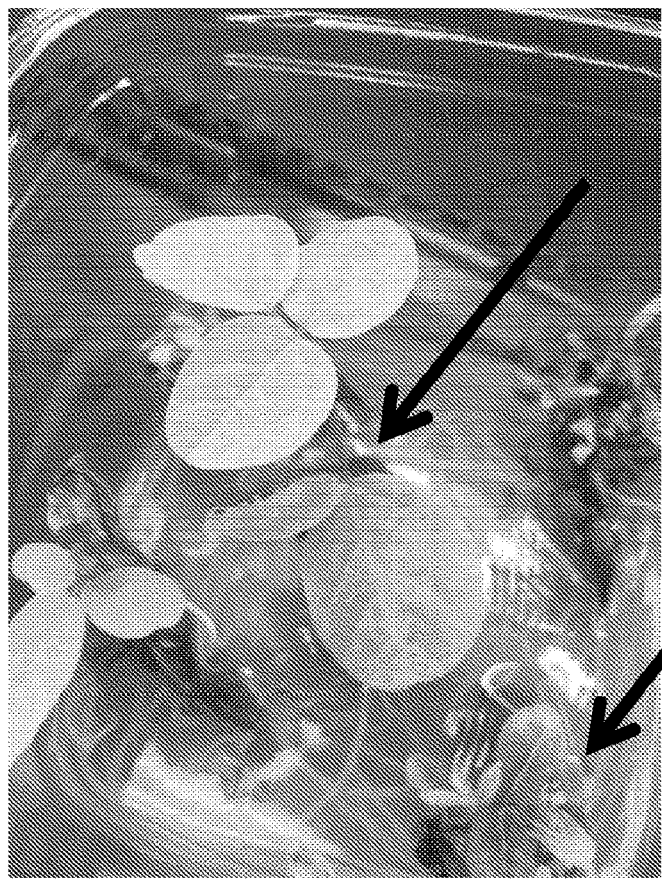

Transformation vectors as illustrated in FIG. 2 were generated, comprising various components of a PQ9-synthetic pathway derived from *Synechocystis* sp. (strain PCC6803). Sequences of the coding regions illustrated at FIG. 2 are set forth below in Table 1, along with the petC coding sequence:

TABLE 1

| Locus | Polypeptide (Enzyme activity) | Sequence |
|---|---|---|
| Sll1797 | UbiC (Chorismate lyase) | atgaagctctctcccgctgtttctcctagtcttgcttggcattctttggatttgctgtggcaagg agatcaacatgatgtgaggcatgggcttcctcattctgttcttcctcctccatggcagatcctc attcttggagatggctccccaacaaggcatttgcagcttctcactggagagaagacagaag tggatgtgattgacatggctcctgtttcaccaagagatgatggtgctcctcctcaaattaaca ctgttcctggccctcacttgagaaggcaagtttggctgaggaccaagagtggccaaaggc ttgcttatgctgtttcttggtgggatgcttctcatgttgatgaatatttgcaaaacagaagtttgc caatttgggattctctctcaaggcttcacacagagctttacagagacattcaagctatctattg tggccacaacagaactctagcaaaggcttttggccaagaaggacccttctggggaaggc attacctctttggcatgacaggaagccattgacattgatctatgagatcttctctccatatctct caagatatcttggagagcttccaaggccaaaatttgaa (SEQ ID NO: 11) |
| Slr0926 | UbiA (4-hydroxybenzoate solanesyltransferase) | atggtggctcaaactccttcttctcctcctctttggttgacaatcatctatttgctgagatggcat aaacctgctggaaggttgatcttgatgattcctgctctttgggctgtttgcttggctgctcaag ggcttcctcctcttcctcttcttggaaccattgctcttggaactttggcaacaagtggcttggg atgtgtggtgaatgatctatgggacagagacattgatcctcaagtggaaagaacaaagcaa aggcctcttgctgctagagctttgtcagttcaagttggaattggagttgctttggtggctcttct ttgtgctgctggcttggctttctatttgacaccattgagcttctggctttgtgttgctgctgttcca gtgattgttgcttatcctggagctaagagggtgttcctgttcctcaattggtgctctcaattgc ttggggatttgctgtgctgatttcttggagtgctgtcactggagatttgacagatgcaacatg ggtgctttggggagcaacagtgttctggactcttggctttgacactgtttatgcaatggctga cagagaagatgacagaaggattggggtgaactcttcagctctcttctttggccaatatgttg gagaagctgttggaatcttctttgctctcaccattggatgcttgttctatttggggatgatcttg atgcttaatcctctatattggctctctcttgccattgttggatgggtgatccaatacatt caattgagtgctccaacaccagagccaaagctctatggccaaattttggacaaaatgtgat cattggatttgttcttcttgctgggatgctgcttggatggctgtga (SEQ ID NO: 12) |
| Slr1099 | UbiX (4-hydroxy-3-prenylbenzoate decarboxylase) | atggctcaaccattgattcttggagtttctggagcttctggcttgatttatgctgtgagagcaat caagcatttgttggctgctgattacaccatagagttggtggcttcaagagcaagctatcaagt ttggcaagcagagcaaaacatccagatgcctggagaaccttctgctcaagcagaattttgg agaagccaagctggtgttgagaaggagggaagctcatttgccacagatggggagatgtt ggagcaacaattgcttctggaagctacagatgtgctggaatggtggtgcttcctgctcaat gagcactgtggcaaagctggctgttggaatgtcttcagatttgctggagagagctgctgat |

TABLE 1-continued

| Locus | Polypeptide (Enzyme activity) | Sequence |
|---|---|---|
| | | gttcaaatcaaggaaggaaagccattggtggtggttccaagagaaactcctctctctttgat<br>ccatttgaggaatctcacttcattggcagaagctggagtgagaattgttcctgcaattcctgc<br>ttggtatcatcaacctcaaagtgtggaagatttggtggattttgttgttgcaagagctttggatc<br>agctggccattgattgtgttcctcttcaaagatggcaaggaggaatggaaggagag<br>(SEQ ID NO: 13) |
| Sll0936 | UbiD<br>(Interacts with UbiX for the same activity) | atggcaagagatttgagaggcttcattcagctgttggaaacaagaggccaattgagaagg<br>atcactgctgaagttgatccagatttggaggttgctgagatttcaaacaggatgctgcaagc<br>tggtggacctggcttgctgtttgagaatgtcaagggaagccccttttcctgttgctgtgaacttg<br>atgggaactgtggaaaggatttgctgggcaatgaacatggatcatccattggagttggaag<br>atttggggaagaagctggctcttcttcagcaaccaaagccaccaaagaagatttcacaagc<br>tattggattttggaaaggttctctttgatgtgctgaaggcaaagcctggaaggaacttcttccct<br>ccttgccaagaagtggtgattgatggagagaacttggatctaaaccaaattcctctcatcag<br>gccatatcctggagatgctgggaagatcatcacccttggcttggtgatcaccaaggattgtg<br>aaactggaactccaaatgttggagtttacaggttgcagctgcaatcaaagacaacaatgac<br>agtgcattggctctctgtgagaggaggagcaaggcatttgaggaaagctgctgagcaag<br>ggaagaagctggaggtggccattgctcttggagttgatccattaatcatcatggctgctgca<br>acaccaattccagtggatctctcagaatggctgtttgctggcctctatggaggaagtggagt<br>tgctctagcaaaatgcaaaacagtggattttggaggttcctgctgattcagaatttgtgttgga<br>aggaaccatcactcctggagagatgcttcctgatggccccctttggagatcacatgggatatt<br>atggaggagtggaagattcaccattggtgaggttccaatgcttgacccacaggaagaatc<br>cagtttatttgacaactttctctggaaggccaccaaaggaagaagcaatgatggccattgct<br>ctcaacaggatctacactccaatcttgaggcagcaagtttcagagatcactgatttcttcctc<br>caatggaagctctctcctacaaggctgccatcatctcaattgacaaggctatcctggcca<br>agcaaagagagctgctttggctttctggagtgctcttcctcaattcacctacaccaagtttgtg<br>attgtggtggacaagagcatcaactcagagatccaaggcaagtggtttgggccatttcttc<br>caaggttgatccagtgagagatgtcttcattcttccagaaacaccatttgattcttttggatttg<br>cttcagagaagattggcttggggaggaaggatgggaattgatgcaacaacaaagattcctc<br>cagaaacagatcatgaatggggagaagtgttggagagtgatccagcaatggcagagcaa<br>gtttctcaaagatgggcagaatatggcttgggagatattaatttgacagaggtgaatccaaa<br>cctctttggatatgatgtgtaa (SEQ ID NO: 14) |
| Slr1300 | UbiH<br>(Hydroxylase) | atgacatttgttgctgcttcaatcactgacaaccaatttgatgttgccattgctggtggaggag<br>tggttggcttggtgcttgctgctggcttgaggcacactggcttgaagattgccatcattgaag<br>ctcttccaaaggagcaagcattgacaaagcctcaagcatatgcaatttctctcttctctctggga<br>agattcttgctggcttgggagtttggaaaatcaaggattcaattggccattttgagagga<br>ttcaaatttcagataatgattacagaggaactgttccatttgccaaggaagatgttgatgagct<br>ggctcttggccatgttgctgagcatccagtgattcttcaagcattggagaattgtgtggagca<br>atgcccaaggattgcttggttcagacagcagagttgatttcactgctggagagaacc<br>acaagcaagtgacattgcagcaaggaagagaaatcactcttcaaaccaagctgctg<br>gtggctgctgatggagcaagaagccacacaagatcattggctgaatccaaaccaaagg<br>atggaaatattggcaaagctgtgtagctttcaccattcagcaccaagctccagacaacacc<br>actgcttttgaaagattttgtgacactggaccaatgggaatcttacctcttcctggagacaga<br>gcacaaattgtttggacaatgcctcaccacaaggctcacaccttggtgaatcttccagaagc<br>tgatttcatcacagagttaaggcaaaggattggagacaggcttggagaatttcatctaattaa<br>tgcaagaaggttgtttcctgttcagttgatgcaaagtgattgctatgttcaaccaaggcttgct<br>ttggttggagatgctgctcattgctgccaccctgttggtggccaaggattgaacttgggaat<br>cagagatggagctgctttggctcaagtgattgcaactgctcattcacaaggagaagattgg<br>ggaagtttggctgtgctgaagagatgagcattggaggaagccagagaattggttgattc<br>ttggcttcactgatttgctggacagattcttctcatctcattggcttcctgcaattgctttgagaa<br>gatttggcttggaggtgctgaggttggtgccaccagcaaagaagctggctttgaggttgat<br>gactggctgcttggaaggaagcctcagcttgcaactggccaaagtttggtttctcagtag<br>(SEQ ID NO: 15) |
| Sll0418 | Uncharacterized methyltransferase (MPBQ/MSBQ methyltransferase) | atggctggcttgtatttgctgacagcaaggaggatatcaaagctcagattctgttgcaaatgct<br>tatgatcaatggacagaagatggaatcttggaatattattggggagatcacattcatcttggc<br>cattatggagatcctcctgttgccaaggatttcatccaaagcaagatagatttgttcatgcaa<br>tggctcaatggggaggattggacactcttcctcctggaacaacagtgcttgatgttggatgt<br>ggaattggaggaagctcaaggatcttggccaaggattatggcttcaatgtcactggaatca<br>ccatttctcctcaacaagtgaagagacaagaattaacaccaccagatgtcactgcaaa<br>gtttgctgttgatgatgcaatggctctctcatttcctgatggaagttttgatgtggtttggagtgt<br>ggaagctggtcctcacatgccagacaaggctgtttttgccaaggagttgctgagggtggtg<br>aagcctggaggaatcttggtggttgctgattggaatcaaagagatgacaggcaagttcctc<br>tcaacttctgggagaagccagtgatgaggcaattgctggatcaatggagccaccctgctttt<br>gcttcaattgaaggatttgctgagaacttggaagcaactggctggtggaaggccaagtga<br>caactgctgattggactgttccaactcttcctgcttggttggacacatttggcaaggaatcat<br>caggcctcaaggatggctgcaatatggaatcagaggcttcatcaaatcagtgagagaagtt<br>ccaaccatcttgctgatgaggcttgcttttggagttgggcttgcaggtttggaatgttcaagg<br>ctgtgagaaaaatgcaacacaagcctaa (SEQ ID NO: 16) |
| slr0089 | Uncharacterized methyltransferase | atggtttaccatgtgaggccaaagcatgctctcttcttggctttctattgctacttctctctgctg<br>acaatggcttcagcaaccattgcttctgctgatctctatgaaaaattaaaaactctatgatgt<br>attcttctggcttgtgggaagatgtttggggagagcacatgcaccatgatattatggcctc<br>atggaacctacaggattgacagaaggcaagctcaaattgatttgatcaaagagctattggct<br>tgggctgttcctcaaaatagcgcaaagccaaggaagatcttggatcttggatgtggaattg<br>gaggaagctctctctatttggctcagcagcatcaagcagaggtgatgggagcttctctctca<br>ccagtgcaagttgaaagagctggaaaagagcaagagctttgggcttggttctacttgcc |

TABLE 1-continued

| Locus | Polypeptide (Enzyme activity) | Sequence |
|---|---|---|
| | | aattccaagtggcaaatgctttggatcttccatttgcttcagattcctttgattgggtttggagct<br>tggagagtggagagcacatgccaaacaaggctcaatttcttcaagaagcatggagggtgc<br>tgaagcctggaggaaggttgatcttggcaacttggtgccacaggccaattgatcctggaaa<br>tggccctctcactgctgatgaaagaaggcatcttcaagcaatctatgatgtttattgcttgcca<br>tatgtggtttcattgccagattatgaagccattgcaagagaatgtggctttggagaaattaag<br>actgctgattggagtgttgctgttgctccatttttgggacagggtgattgaatcagcttttgatc<br>caagggtgctttgggctcttggtcaagctgggccaaagatcatcaatgctgctctctgcttg<br>agattaatgaaatggggatatgaaagaggcttggtgagtttggcttgctcactggaatcaa<br>gccactggtg (SEQ ID NO: 17) |
| sll1407 | Uncharacterized methyltransferase | atgaagaagaatgtttactattccaagattgctgacatctatgatcaaacaaggtggatgaca<br>gaaccaattgctgaagaagttgctgatttcatcctggctttggtgaaggcaacaagggaaa<br>caaccttcctggagcctggtgttggaactggcttgaatgtgatccctctggtgaggagagg<br>atattcagtcactggagtggacatctctcaagagatgctctctcaatttctcaaaagctgcca<br>aggattcctccaaacttgaggctgatccatgaagatgcaagccagctgagcttcccagatt<br>cttcctttgatgtggtgctcactgtgcacatgctgcattctgtttcaaacttggggatgttcctg<br>gatgagattgacagggtgctgaagccaaatggcttctacttgaatgctcaatgggtgacac<br>caccagctcacctggagtttgagaaccacttcaagaccatcttgctgaagtaccaagagcc<br>aaagccctcacagcaaagtttggaggtcaccaacaagatcaacattgatgaatatctgctg<br>aacaaaggctaccaatgcaactacttgacagccaaggaatggacagtttcaaaccaagtg<br>caagagctgctgcatttctacagaagccatgcttatggcttgtgctggctgcttcctgatgaa<br>gccttcaacttggccatcaaggagtttgaggtgttctgctatgaatattatgattccctcaagg<br>tggagctttcaagccaagctcagtttgagatttgggcctacactgtgaag (SEQ ID NO: 18) |
| slr0407 | Uncharacterized methyltransferase | atgacatattttgcttcagatttccaagatttggacaacagtggcaacattgagaacttcatca<br>gatgcttggagctgcaacaaagtttggatctctacaaatactacaagcagaagacctttgag<br>aagatgcagctgaagcctggagattcagtgctggaggttggatgtggaactggaaatgat<br>gctcttcttctggccaactatgttggagaaactgggaaggtgactgctgtggacagaagcc<br>aattcatgctggatcaagcaagagaaagagccaagaactcaacaaccaagtttgagtttgt<br>gctagctgatgctgagcagcttcccttccctggagcaaacttcactgctgcaagggtggac<br>agaaccctccagcacattgctcagcctcagaaggccattgctgagatggcaagggtggtg<br>caaagcaatggatgggtggtggcttttgagccagattgggaaaccttggtgattgattcaga<br>tcaaagaggagtgacaagagccatcaccaacttctggtgtgacaacttcccttctggatgg<br>gtgggaagatatctcttcaaatacttcagacaagctggcttgacagacattgctgttgatcca<br>atcaccatttgcttgacagagtttgagcttgctgataaaattttggatctctcaaggacagtgg<br>aaaaaattctgagcaaggaaccatctctcagaatgatttgacccttggttcaaggccattg<br>atcagaatgatcaagctggagagttcttctgtgccttcactgccttcttggtgagaggaagg<br>aagcca (SEQ ID NO: 19) |
| sll0829 | Uncharacterized methyltransferase | atggcaacaatcttcagaacttggagctaccaatatccatgggtttatgctttggtttcaaggt<br>tggcaacattgaatgttggaggagaagaaaggttccaccagcttcctttggagaacttggct<br>atctctcctggccagaaggtgcttgatctttgctgtggaggaggccaagcaacagtttactt<br>ggctcaaagtggagcaacagtggttggcttggatgcttcaccaaaggctcttggaagagc<br>aaaaattaatgttcctcaagcaacatatgttcaaggattagcagaagatcttccatttggaga<br>aggagaatttgatttggtgcacacttctgttgctcttcatgagatgacaccagctcagctgca<br>aagcatcatcagtggagttcacagggtgctgaagcctggaggaatctttgctttggtggatc<br>ttcacaggccttcaaattggctcttctggccacccttggcaatttcatgggattgtttgaaac<br>agaaactgcttggcagctaattaacacagatttgggaagtttgctggatcaagctggcttca<br>ctgtggtgagaaagcatttgtatgctggaggaagtttgcaagtgatccaagcaagagccaa<br>caagacagtgaactaa (SEQ ID NO: 20) |
| petC | PetC (Plastoquinol-plastocyanin reductase) | atgttagtaaaaatccttaaatttagacggttcattatgacacagatttctggctcccctgatgt<br>ccccgatttgggtcggcgtcagtttatgaacttattgaccttcggtacgatcactggggtggc<br>ggccggggccctctatccagcagtaaaatatttgatcccccctccagtggtggttcgggc<br>ggtggtgtaacggccaaagatgccttggtaatgatgttaaggtgacggaattttttggcttc<br>ccataacgctggcgatcgggtgttggcccaggggttgaaggggcgacccgacctatattgt<br>agtccaggggatgacacgatcgccaactatggtattaatgcggtgtgtacccatttggc<br>tgtgtagtgccctggaatgccagcgaaaacaaatttatgtgcccttgtcacggctcccagta<br>caacgctgaaggtaaagtggtccgtggcccggctcccctctctttggctttggcccacgct<br>accgttaccgacgacgacaaattagtgctcagcacctggaccgaaaccgatttccgcacc<br>gacgaagatccctggtgggcttag (SEQ ID NO: 23) |

Two transformation vectors were generated: pBlay01772, encoding 6 Synechocystis genes (Sll1797, Slr0926, Slr1099, Sll0936, Slr1300, and Sll0418); and pBay01773, encoding 9 Synechocystis genes (Sll1797, Slr0926, Slr1099, Sll0936, Slr1300, Slr0089, Sll1407, Slr0407, and Sll0829). Each vector includes the following expression cassettes: (1) a CsVMV promoter operably linked to Sll1797 and Slr1300 (separated by a linker region encoding an amino acid sequence GSAGSAAGSGEF (SEQ ID NO: 21)), an optimized transit peptide (OTP) and a 35S 3' untranslated region (UTR); (2) a plant ubiquitin promoter (Ubi10) operably linked to Slr1099 and Sll0936 (separated by the linker), an OTP and a 3' hist UTR; and (3) a 35S promotor operably linked to Slr0926, an OTP and a 3' nos UTR. pBlay01772 additionally contains the following fourth expression cassette: (4) a H4A748 promotor operably linked to Sll0418, an OTP and a 3' nos UTR. pBay01773 additionally contains the following fourth expression cassette: (4) a H4A748 promotor operably linked to Slr0089, Sll1407, Slr0407, and Sll0829 (each separated by the linker), an OTP and a 3' nos UTR, right border and left border sequences.

Example 2: Transformation of Soybean

The vectors described in FIG. 2 were transformed into soybean plants using standard methods for transformation. Both vectors were capable of generating viable plants grown in the presence of 0.2 mg/L Tembotrione The resultant transformants were evaluated for the copy number (CN) and were tested by quantitative PCR with existing methods for 3 components (3'nos UTR, 35S promoter, CsVMV promoter) present in the transforming DNA.

The CN data shows that the first 3 cassettes always are present in the selected events, suggesting that the presence of each of slr1300, sll1797, sll0936, slr1099, and slr0926 is sufficient to confer tolerance of the plants to HPPD inhibitor herbicide. It is possible that fewer than all 5 genes are needed, as some enzymatic activities may be provided by resident enzymes in higher plant chloroplasts. For example, since all 3 cassettes are maintained, one possible scenario is that tolerization may be obtained by providing: (a) at least one of Sll1797 and Slr1300; (b) at least one of Slr1099 and Sll0936, and (c) Slr0926. Other combinations may also be possible.

The CN data of 3'nos is almost always 1, which likely means that the cassette encoding methyltransferase(s) is dispensable. This may mean that plants have a functional homolog for uncharacterized/unidentified methyltransferases in the cyanobacterial pathway. The fact that transformants could be selected with both vectors (which only differ by the methyltransferase cassette) also indicates that tolerization could be achieved without obtaining transformants expressing a cyanobacterial methyltransferase.

That which is claimed:

1. A method for providing a plant having increased tolerance to a 4-hydroxyphenylpyruvate dioxygenase (HPPD) inhibitor herbicide, the method comprising:
   (i) expressing in the plant transgenes encoding exogenous polypeptides of a cyanobacterial pathway for biosynthesis of 2-solanesyl-1,4-benzoquinol (SBQ) from endogenous chorismate, said exogenous polypeptides being the polypeptides of:
   (a) at least one cyanobacterial chorismate lyase enzyme,
   (b) at least one cyanobacterial 4-hydroxybenzoate solanesyltransferase enzyme,
   (c) at least one cyanobacterial 4-hydroxy-3-prenylbenzoate decarboxylase enzyme, and
   (d) at least one cyanobacterial solanesylphenol hydroxylase enzyme;
   (ii) growing the plants having the transgene in the presence of an herbicide; and
   (iii) selecting the plants, wherein the selected plants have increased tolerance relative to a control plant not having the transgenes exogenous polypeptides of a cyanobacterial pathway for biosynthesis of 2-solanesyl-1,4-benzoquinol (SBQ);
   wherein the chorismate lyase enzyme polypeptide comprises a UbiC polypeptide having at least 75% sequence identity to SEQ ID NO: 1 or to the polypeptide encoded by SEQ ID NO: 11,
   wherein the 4-hydroxybenzoate solanesyltransferase enzyme polypeptide comprises a UbiA polypeptide having at least 75% sequence identity to SEQ ID NO: 2 or to the polypeptide encoded by SEQ ID NO: 12;
   wherein the 4-hydroxy-3-prenylbenzoate decarboxylase enzyme polypeptide comprises either a UbiX polypeptide or a UbiD polypeptide, or said plant comprises two cyanobacterial 4-hydroxy-3-prenylbenzoate decarboxylase enzyme polypeptides comprising a UbiX polypeptide and a UbiD polypeptide wherein the UbiX polypeptide has at least 75% sequence identity to SEQ ID NO: 3 or to the polypeptide encoded by SEQ ID NO: 13, and/or wherein the UbiD polypeptide has at least 75% sequence identity to SEQ ID NO: 4 or to the polypeptide encoded by SEQ ID NO: 14;
   wherein the 4-hydroxy-3-prenylbenzoate decarboxylase enzyme polypeptide comprises either a UbiX polypeptide or a UbiD polypeptide, or said plant comprises two cyanobacterial 4-hydroxy-3-prenylbenzoate decarboxylase enzyme polypeptides comprising a UbiX polypeptide and a UbiD polypeptide wherein the UbiX polypeptide has at least 75% sequence identity to SEQ ID NO: 3 or to the polypeptide encoded by SEQ ID NO: 13, and/or wherein the UbiD polypeptide has at least 75% sequence identity to SEQ ID NO: 4 or to the polypeptide encoded by SEQ ID NO: 14; and
   wherein the solanesylphenol hydroxylase enzyme polypeptide comprises a UbiH polypeptide wherein the UbiH polypeptide has at least 75% sequence identity to SEQ ID NO: 5 or to the polypeptide encoded by SEQ ID NO: 15.

2. The method of claim 1, wherein the plant comprises enzymes that convert SBQ to plastoquinone-9 (PQ9), said enzymes being:
   (e) at least one MPBQ/MSBQ methyltransferase enzyme, and
   (f) at least one plastoquinol-plastocyanin reductase enzyme, and
   wherein said MPBQ/MSBQ methyltransferase enzyme(s) comprise at least one exogenous, cyanobacterial MPBQ/MSBQ methyltransferase polypeptide expressed from a transgene in the plant;
   wherein said cyanobacterial MPBQ/MSBQ methyltransferase polypeptide(s) comprise at least one of a Sll0418 polypeptide, a slr0089 polypeptide, a sll1407 polypeptide, a slr0407 polypeptide, and/or a sll0829 polypeptide, wherein the Sll0418 polypeptide has at least 75% sequence identity to SEQ ID NO: 6 or to the polypeptide encoded by SEQ ID NO: 16, the slr0089 polypeptide has at least 75% sequence identity to SEQ ID NO: 7 or to the polypeptide encoded by SEQ ID NO: 17, the sll1407 polypeptide has at least 75% sequence identity to SEQ ID NO: 8 or to the polypeptide encoded by SEQ ID NO: 18, the slr0407 polypeptide has at least 75% sequence identity to SEQ ID NO: 9 or to the polypeptide encoded by SEQ ID NO: 19, and/or the sll0829 polypeptide has at least 75% sequence identity to SEQ ID NO: 10 or to the polypeptide encoded by SEQ ID NO: 20.

3. The method of claim 1, wherein the exogenous polypeptides further comprise at least one of a Sll0418 polypeptide, a slr0089 polypeptide, a sll1407 polypeptide, a slr0407 polypeptide, and/or a sll0829 polypeptide, wherein the Sll0418 polypeptide has at least 75% sequence identity to SEQ ID NO: 6 or to the polypeptide encoded by SEQ ID NO: 16, the slr0089 polypeptide has at least 75% sequence identity to SEQ ID NO: 7 or to the polypeptide encoded by SEQ ID NO: 17, the sll1407 polypeptide has at least 75% sequence identity to SEQ ID NO: 8 or to the polypeptide encoded by SEQ ID NO: 18, the slr0407 polypeptide has at least 75% sequence identity to SEQ ID NO: 9 or to the polypeptide encoded by SEQ ID NO: 19, and/or the sll0829 polypeptide has at least 75% sequence identity to SEQ ID NO: 10 or to the polypeptide encoded by SEQ ID NO: 20.

4. The method of claim 1, wherein the exogenous polypeptides are expressed from at least one transformation vector.

5. The method of claim 4, wherein the transformation vector further comprises a nucleic acid encoding one or more of one or more of a Sll0418 polypeptide, a slr0089 polypeptide, a sll1407 polypeptide, a slr0407 polypeptide, and/or a sll0829 polypeptide, wherein the Sll0418 polypeptide has at least 75% sequence identity to SEQ ID NO: 6 or to the polypeptide encoded by SEQ ID NO: 16, the slr0089 polypeptide has at least 75% sequence identity to SEQ ID NO: 7 or to the polypeptide encoded by SEQ ID NO: 17, the sll1407 polypeptide has at least 75% sequence identity to SEQ ID NO: 8 or to the polypeptide encoded by SEQ ID NO: 18, the slr0407 polypeptide has at least 75% sequence identity to SEQ ID NO: 9 or to the polypeptide encoded by SEQ ID NO: 19, and/or the sll0829 polypeptide has at least 75% sequence identity to SEQ ID NO: 10 or to the polypeptide encoded by SEQ ID NO: 20.

6. The method of claim 1, wherein the plant is a soybean plant.

7. A plant or plant cell comprising the exogenous polypeptides referred to in claim 1.

8. The plant or plant cell of claim 7, wherein said plant or plant cell comprises 2-solanesyl-1,4-benzoquinol (SBQ) produced in the plant or plant cell from endogenous chorismate by enzymes comprising said exogenous polypeptide(s).

9. The plant or plant cell of claim 7, wherein said plant or plant cell comprises plastoquinol-9 (PQH2) or plastoquinone-9 (PQ9) biosynthesized in the plant or plant cell from SBQ produced in the plant or plant cell from endogenous chorismate by enzymes comprising said exogenous polypeptide(s).

10. The plant or plant cell of claim 9, wherein (i) said PQH2 is biosynthesized by at least one endogenous MPBQ/MSBQ methyltransferase enzyme(s), or (ii) said PQ9 is biosynthesized by at least one endogenous plastoquinol-plastocyanin reductase, or (iii) both (i) and (ii).

11. The plant or plant cell of claim 9, wherein said PQH2 is biosynthesized by at least one MPBQ/MSBQ methyltransferase enzyme(s) comprising exogenous cyanobacterial MPBQ/MSBQ methyltransferase polypeptide(s) expressed from transgene(s) in the plant or plant cell.

12. The plant or plant cell of claim 11, wherein said exogenous MPBQ/MSBQ methyltransferase polypeptide(s) comprises at least one of a Sll0418 polypeptide, a slr0089 polypeptide, a sll1407 polypeptide, a slr0407 polypeptide, and/or a sll0829 polypeptide, wherein the Sll0418 polypeptide has at least 75% sequence identity to SEQ ID NO: 6, the slr0089 polypeptide has at least 75% sequence identity to SEQ ID NO: 7, the sll1407 polypeptide has at least 75% sequence identity to SEQ ID NO: 8, the slr0407 polypeptide has at least 75% sequence identity to SEQ ID NO: 9, and/or the sll0829 polypeptide has at least 75% sequence identity to SEQ ID NO: 10.

13. The plant or plant cell of claim 7, wherein the exogenous polypeptides:
further comprise at least one of a Sll0418 polypeptide, a slr0089 polypeptide, a sll1407 polypeptide, a slr0407 polypeptide, and/or a sll0829 polypeptide, wherein the Sll0418 polypeptide has at least 75% sequence identity to SEQ ID NO: 6 or to the polypeptide encoded by SEQ ID NO: 16, the slr0089 polypeptide has at least 75% sequence identity to SEQ ID NO: 7 or to the polypeptide encoded by SEQ ID NO: 17, the sll1407 polypeptide has at least 75% sequence identity to SEQ ID NO: 8 or to the polypeptide encoded by SEQ ID NO: 18, the slr0407 polypeptide has at least 75% sequence identity to SEQ ID NO: 9 or to the polypeptide encoded by SEQ ID NO: 19, and/or the sll0829 polypeptide has at least 75% sequence identity to SEQ ID NO: 10 or to the polypeptide encoded by SEQ ID NO: 20.

14. The plant or plant cell of claim 7, wherein the plant is a soybean plant, or the plant cell is a soybean plant cell.

15. Isolated nucleic acid comprising:
coding regions of the transgenes referred to in claim 1, the nucleic acid encoding: said chorismate lyase polypeptide(s) or an enzymatically active component thereof,
said 4-hydroxybenzoate solanesyltransferase peptide(s) or an enzymatically active component thereof,
said 4-hydroxy-3-prenylbenzoate decarboxylase peptide(s) or an enzymatically active component thereof, and
said solanesylphenol hydroxylase peptide(s) or an enzymatically active component thereof, and optionally at least one cyanobacterial MPBQ/MSBQ methyltransferase polypeptide or an enzymatically active component thereof; and
at least one plant-expressible promoters operably linked to the coding region(s).

16. The isolated nucleic acid of claim 15, wherein each of said plant-expressible promoters is able to drive expression in a soybean plant of the coding region(s) to which it is linked.

17. The isolated nucleic acid of claim 15, wherein said coding regions comprise:
a nucleotide sequence encoding a UbiC polypeptide, a nucleotide sequence encoding a UbiA polypeptide, a nucleotide sequence encoding a UbiX polypeptide,
a nucleotide sequence encoding a UbiD polypeptide, and a nucleotide sequence encoding a UbiH polypeptide, wherein isolated nucleic acid of claim 15, wherein said coding regions further comprise nucleotide sequence(s) encoding at least one of a Sll0418 polypeptide, a slr0089 polypeptide, a sll1407 polypeptide, a slr0407 polypeptide, and a sll0829 polypeptide, wherein the Sll0418 polypeptide has at least 75% sequence identity to SEQ ID NO: 6 or to the polypeptide encoded by SEQ ID NO: 16, the slr0089 polypeptide has at least 75% sequence identity to SEQ ID NO: 7 or to the polypeptide encoded by SEQ ID NO: 17, the sll1407 polypeptide has at least 75% sequence identity to SEQ ID NO: 8 or to the polypeptide encoded by SEQ ID NO: 18, the slr0407 polypeptide has at least 75% sequence identity to SEQ ID NO: 9 or to the polypeptide encoded by SEQ ID NO: 19, and/or the sll0829 polypeptide has at least 75% sequence identity to SEQ ID NO: 10 or to the polypeptide encoded by SEQ ID NO: 20.

18. A transformation vector comprising the isolated nucleic acid according to claim 15.

19. A method for growing a plant comprising:
  obtaining a transgenic plant of any of claim 7 in a field; and
  treating said field with an effective amount of a 4-hydroxyphenylpyruvate dioxygenase (HPPD) inhibitor herbicide.

20. The method of claim 19, wherein said plant is a soybean plant.

* * * * *